(12) United States Patent
Bell et al.

(10) Patent No.: US 7,470,705 B2
(45) Date of Patent: Dec. 30, 2008

(54) COMPOUNDS AND METHODS FOR TREATING DYSLIPIDEMIA

(75) Inventors: Michael Gregory Bell, Indianapolis, IN (US); Guoqing Cao, Carmel, IN (US); Ana Maria Escribano, Madrid (ES); Maria Carmen Fernandez, Madrid (ES); Peter Ambrose Lander, Indianapolis, IN (US); Nathan Bryan Mantlo, Brownsburg, IN (US); Eva Maria Martin de la Nava, Madrid (ES); Ana Isabel Mateo Herranz, Madrid (ES); Daniel Ray Mayhugh, Carmel, IN (US); Xiaodong Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 236 days.

(21) Appl. No.: 10/598,473

(22) PCT Filed: Mar. 17, 2005

(86) PCT No.: PCT/US2005/009301

§ 371 (c)(1),
(2), (4) Date: Aug. 31, 2006

(87) PCT Pub. No.: WO2005/097806

PCT Pub. Date: Oct. 20, 2005

(65) Prior Publication Data

US 2007/0173526 A1 Jul. 26, 2007

Related U.S. Application Data

(60) Provisional application No. 60/557,134, filed on Mar. 26, 2004, provisional application No. 60/621,162, filed on Oct. 22, 2004.

(51) Int. Cl.
*A01N 43/42* (2006.01)
*A61K 31/44* (2006.01)
*C07D 471/02* (2006.01)

(52) U.S. Cl. ...................... 514/300; 546/122

(58) Field of Classification Search ................. 546/122; 514/300

See application file for complete search history.

(56) References Cited

U.S. PATENT DOCUMENTS

| 5,932,587 | A | 8/1999 | Schmeck et al. |
| 6,147,090 | A | 11/2000 | DeNinno et al. |
| 2002/0049207 | A1* | 4/2002 | McCarthy ................ 514/246 |
| 2005/0059810 | A1 | 3/2005 | Maeda et al. |
| 2007/0208003 | A1 | 9/2007 | Bell et al. |
| 2007/0244095 | A1 | 10/2007 | Chen et al. |
| 2007/0254869 | A1 | 11/2007 | Cao et al. |

FOREIGN PATENT DOCUMENTS

| EP | 0992496 | 12/2000 |
| GB | 1 515 540 | 6/1978 |
| JP | 2003321472 A | 11/2003 |
| WO | WO 00/17166 A | 3/2000 |
| WO | WO 2005/095395 | 10/2005 |
| WO | WO 2006/012093 | 2/2006 |

OTHER PUBLICATIONS

Beilstein Crossfire Institut Zur Foerderung Der Chemischen Wissenschaften, DE; BRN 5584498, 1993, XP 002333708, Abstract, Maurice, et al., "Decahydroquinoline derivatives. VIII. 4-Anilino- and 4-anilidodecahydroquinolines and N-substituted derivatives" European Journal of Medicinal Chemistry, 15(3), 215-22 ODEN: EJMCA5; ISSN: 0009-4374, 1980.
Bisgaier et al. *J of Lipid Res.* 1993, 34, 1625-1634.

\* cited by examiner

*Primary Examiner*—D. Margaret Seaman
*Assistant Examiner*—Niloofar Rahmani
(74) *Attorney, Agent, or Firm*—James B. Myers; Francis O. Ginah

(57) ABSTRACT

The present invention discloses compounds of formula (I) wherein A, n, q, K, W, X, Y; Z, $R^1$, $R^2$, $R^3$, $R^4$, $R^5$, and $R^6$ are as defined herein and their pharmaceutical compositions and methods of use are disclosed as useful for treating dyslipidemia and its sequelae.

18 Claims, No Drawings

COMPOUNDS AND METHODS FOR TREATING DYSLIPIDEMIA

This application is submitted as a U.S. national phase entry, pursuant to 35 U.S.C. §371, of PCT/US2005/009301, filed on 17 Mar. 2005, which claims the benefit of U.S. provisional patent applications Ser. No. 60/557,134, filed 26 Mar. 2004 and serial number 60/621,162, filed on 22 Oct. 2004, each of which are incorporated by reference herein.

FIELD OF THE INVENTION

The current invention relates to the fields of medicinal organic chemistry, pharmacology, and medicine. Further, the current invention relates to a group of compounds that demonstrate utility for treating pathological states due to dyslipidemia.

BACKGROUND OF THE INVENTION

Coronary heart disease (CHD) is one of the major causes of morbidity and mortality worldwide. Despite attempts to modify risk factors such as obesity, smoking, lack of exercise, and treatment of dyslipidemia with dietary modification or drug therapy, CHD remains the most common cause of death in the U.S. Over 50% of all CHD deaths are due to underlying atherosclerotic coronary heart disease.

Dyslipidemia is a major risk factor for CHD. Low plasma levels of high density lipoprotein (HDL) cholesterol with either normal or elevated levels of low density (LDL) cholesterol is a significant risk factor for developing atherosclerosis and associated coronary artery disease in humans. Indeed, several studies on lipoprotein profiles of CHD patients have shown that about 50% of the CHD patients have cholesterol levels that are considered to be in the normal range (<200 mg/dl). Furthermore, these studies found low HDL cholesterol in about 40% of the normo-cholesterolemic CHD patients as compared to the general population reported in the National Health and Nutrition Examination Survey. Since low levels of HDL cholesterol increase the risk of atherosclerosis, methods for elevating plasma HDL cholesterol would be therapeutically beneficial for the treatment of cardiovascular disease including, but not limited to, atherosclerosis, CHD, stroke, and peripheral vascular disease.

Cholesterol ester transfer protein (CETP) is a 74 KD glycoprotein that facilitates the exchange of cholesterol esters in HDL for triglycerides in triglyceride-rich lipoproteins (A. R. Tall et. al., (1999) 1999 George Lyman Duss Memorial Lecture: Lipid transfer proteins, HDL metabolism and atherogenesis. *Arterio. Thromb. Vasc. Biol.* 20:1185-1188.). The net result of CETP activity is a lowering of HDL cholesterol and an increase in LDL cholesterol. This effect on lipoprotein profile is believed to be proatherogenic, especially in subjects whose lipid profile constitutes an increased risk for CHD. Niacin can significantly increase HDL, but has serious toleration issues that reduce compliance. Fibrates and the HMG CoA reductase inhibitors raise HDL cholesterol only modestly (~10-12%). As a result, there is a significant unmet medical need for a well-tolerated agent that can significantly elevate plasma HDL levels, thereby reversing or slowing the progression of atherosclerosis.

CETP is expressed in multiple tissues and secreted into plasma, where it associates with HDL (X. C. Jiang et. al., (1991) Mammalian adipose tissue and muscle are major sources of lipid transfer protein mRNA. *J. Biol. Chem.* 266: 4631-4639). Humans and monkeys, which express CETP, have relatively low HDL cholesterol, whereas mice and rats do not express CETP and carry nearly all their cholesterol in HDL. Further more, transgenic expression of CETP in mice results in significantly reduced HDL cholesterol levels and development of severe atherosclerosis compared to control mice (K. R. Marotti et. al., (1993) Severe atherosclerosis in transgenic mice expressing simian cholesteryl ester transfer protein. *Nature:*364, 73-75). Expression of human CETP in Dahl salt-sensitive hypertensive rats led to spontaneous combined hyperlipidemia, coronary heart disease and decreased survival (V. L. M. Herrera et. al., (1999) Spontaneous combined hyperlipidemia, coronary heart disease and decreased survival in Dahl salt-sensitive hypertensive rats transgenic for human cholesteryl ester transfer protein. *Nature Medicine:* 5, 1383-1389).

Antibodies either directly injected into the plasma or generated through vaccine injection can effectively inhibit CETP activity in hamsters and rabbits resulting in elevated HDL cholesterol (C. W. Rittershaus, (1999) Vaccine-induced antibodies inhibit CETP activity in vivo and reduce aortic lesions in a rabbit model of atherosclerosis. Furthermore, antibody neutralization of CETP in rabbits has been shown to be antiatherogenic (*Arterio. Thromb. Vasc. Biol.* 20, 2106-2112; G. F. Evans et. al., (1994) Inhibition of cholesteryl ester transfer protein in normocholesterolennc and hypercholesterolemic hamsters: effects on HDL subspecies, quantity, and apolipoprotein distribution. *J. Lipid Research.* 35, 1634-1645). However, antibody and/or vaccine therapy is not currently a viable option for the treatment of large populations of patients in need of treatment for dyslipidemia and resultant or associated disease state manifestations.

Cholesterol ester transfer protein (CETP) catalyzes the exchange of neutral lipid between HDL and apoB-containing lipoprotein particles. As a net result of this exchange, HDL cholesterol is reduced and LDL particles are further enriched with cholesterol, resulting in LDL cholesterol elevation and formation of small dense LDL particles, which are believed to be more atherogenic. CETP inhibition (small molecule, antibody, anti-sense oligo etc.) effectively elevates HDL cholesterol and also reduces LDL cholesterol in animal models as well as in humans (Whitlock, M. et al., J. of Clin. Invest., 1989, Vol. 84, 129-137, Hirochi, O. et al., Nature, 2000, Vol. 406, 203-207, Grooth, G. et al., Circulation, 2002;105:2159-2165, Clark, R. et al., Arterioscler Thromb Vasc Biol. 2004; 24:1-9, Brousseau M. et al., New Engl. J. Med., 2004, Vol. 350:1505-1515). Further, CETP inhibition leads to the formation of less-dense LDL particles-a benefit in addition to LDL cholesterol lowering (Brousseau M. et al., New Engl. J. Med., 2004, Vol. 350:1505-1515). Thus, administration of CETP inhibitors to humans in need thereof would significantly elevate HDL cholesterol level and reduce LDL cholesterol levels and increase LDL particle size, all of which are believed to benefit patients exposed to atherosclerotic risks.

There have been several reports of small molecule CETP inhibitors. Barrret et. al. (J. Am Chem. Soc., 188, 7863, (1996)) and Kuo et al. (J. Am. Chem. Soc., 117, 10629, (1995)) describe cyclopropan-containing CETP inhibitors. Pietzonka et al. (Biorg. Med. Chem. Lett. 6, 1951 (1996)) describe phosphanate-containing analogs as CETP inhibitors. Coval et al. (Bioorg. Med. Chem. Lett. 5, 605, (1995)) describe Wiedendiol-A and -B related sesquiterpines as CETP inhibitors. Japanese Patent Application No. 10287662-A describes polycyclic, non-amine containing, polyhydroxylic natural compounds possessing CETP inhibition properties. Lee et al. (*J. Antibiotics,* 49, 693-96 (1996)) describe CETP inhibitors derived from an insect fungus. Busch et al. (*Lipids,* 25, 216-220 (1990)) describe cholesteryl acetyl bromide as a CETP inhibitor. Morton and Zillversmit (*J. Lipid Res.,* 35, 836-47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 42-47 (1996)) describe other cysteine modification reagents as CETP inhibitors. Xia et al. Describe 1,3,5-triazines as CETP inhibitors (*Bioorg. Med. Chem. Lett.*, 6, 919-22 (1996)). Bisgaier et al. (*Lipids*, 29, 811-8 (1994) describe 4-phenyl-5-tridecyl-4H-1,2,4-triazole-thiol as a CETP inhibitor. Oomura et al., disclose non-peptidic tetracyclic and hexacyclic phenols as CETP inhibitors in Japanese Patent Application No. 10287662.

U.S. Pat. No. 6,586,448 B1 describes 4-caboxamino-2-substituted-1,2,3,4-tetrahydroquinolines of formula I

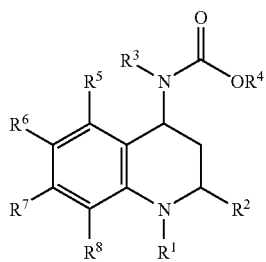

I and prodrugs thereof, and pharmaceutically acceptable salts of said compounds and said prodrugs; wherein $R^1$, $R^2$, $R^3$, $R^4$, $R^5$, $R^6$, $R^7$ and $R^8$ are as defined therein. Similarly, PCT patent applications WO 03/063868A1, WO 0017164, No.0017165, and WO 0017166, discloses variously, formulations, methods of preparation and methods of use of tetrahydroquinoline compounds generally related to that of U.S Pat. No. 6,586, 448 B1 from which it derives or is a divisional application thereof.

European Patent Application No. 818448 by Schmidt et al. describes tetrahydroquinoline derivatives as cholesteryl ester transfer protein inhibitors. European Patent Application No. 818197, Schmek et al., describe pyridines with fused heterocycles as cholesteryl ester transfer protein inhibitors. Brandes et al. in German Patent Application No. 19627430 describe bicyclic condensed pyridine derivatives as cholesteryl ester transfer protein inhibitors. In U.S. Pat. No. 6,207,671 Schmidt et al., describe substituted pyridine compounds as CETP inhibitors. In WO Patent Application No. 09839299, and WO Patent application No.03028727 by Muller-gliemann et al. and Erfinder/Anmelder respectively, describe quinoline derivatives as cholesteryl ester transfer protein inhibitors.

The above disclosures notwithstanding, a great need remains for effective compounds useful as CETP inhibitors to treat conditions caused by, associated with or exacerbated by dyslipidemia.

SUMMARY OF THE INVENTION

The present invention provides a compound of formula I

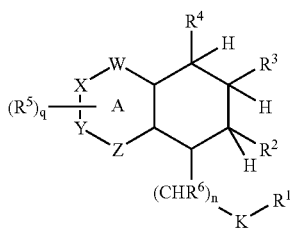

I wherein
n is 0, 1, 2, or 3;
q is 0, 1, or 2;
W, X, Y and Z are each independently CH, C, N, S, or O with appropriate single or double bonds and/or hydrogen atoms to complete valency requirements;
Ring A is a five or six member ring wherein one of W, X, Y and Z may be absent;
provided that ring A is not phenyl;
K is a bond, C=O, or $S(O)_p$;
p is 0, 1 or 2;
$R^1$ when n is 0, and k is C=O or $S(O)_p$, is selected from a group consisting of —$OC_1$-$C_6$ alkyl, —O-aryl, —$OC_2$-$C_6$ alkenyl, —$OC_1$-$C_6$ haloalkyl, —$OC_1$-$C_6$ alkylheterocyclic, —$OC_3$-$C_8$cycloalkyl, —$OC_1$-$C_6$ alkylcycloalkyl, —$NR^7R^8$, —$OC_1$-$C_6$ alkylaryl, —$OC_1$-$C_6$alkyl$CO_2R^{11}$, —$OC_2$-$C_6$alkylalcohol, —$OC_1$-$C_6$ alkyl$NR7R8$, —$OC_2$-$C_6$ alkylcyano, $CONR^{11}R^{12}$, $NR^{11}SO_2R^{12}$, $NR^{11}COR^{12}$, $C_2$-$C_3$ alkyl$NR^{11}R^{12}$, $C_1$-$C_3$ alkyl$COR^{11}$, $C_0$-$C_6$ alkyl$COOR^{11}$ and wherein each cycloalkyl, aryl and heterocyclic group is optionally substituted with 1 to 3 groups independently selected from oxo, hydroxy, halo, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —$C_1$-$C_6$ alkylalcohol, $OC_2$-$C_6$ alkylalcohol, $C_1$-$C_6$ haloalkoxy, $CONR^{11}R^{12}$, $NR^{11}SO_2R^{12}$, $NR^{11}COR^{12}$, $C_0$-$C_3$ alkyl$NR^{11}R^{12}$, $C_1$-$C_3$ alkyl$COR^{11}$, $C_0$-$C_6$ alkyl$COOR^{11}$, $C_0$-$C_6$ alkylcyano, —$OC_2$-$C_6$alkylcyano, $C_1$-$C_6$ alkylcycloalkyl, phenyl, —$OC_1$-$C_6$ alkylcycloalkyl, —$OC_1$-$C_6$ alkylaryl, —$OC_1$-$C_6$ alkylheterocyclic, and $C_1$-$C_6$ alkylaryl;
$R^1$ when n is 1 or 2 or 3, and K is a bond, is selected from a group consisting of hydroxy, $C_1$-$C_6$ alkyl, $C_2$-$C_6$ alkenyl, $C_1$-$C_6$ haloalkyl, $C_1$-$C_6$ alkylheterocyclic, $C_3$-$C_8$ cycloalkyl, $C_1$-$C_6$ alkylcycloalkyl; $C_1$-$C_6$ alkylaryl, aryl, heterocyclyl, $C_1$-$C_6$ alkylalcohol, $C_1$-$C_6$ alkyl$NR^7R^8$, wherein each cycloalkyl, aryl and heterocyclic is optionally substituted with 1 or 2 groups independently selected from the groups consisting of oxo, hydroxy, halo, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —$C_1$-$C_6$ alkylalcohol, $OC_2$-$C_6$ alkylalcohol, $C_1$-$C_6$ haloalkoxy, $CONR^{11}R^{12}$, $NR^{11}SO_2R^{12}$, $NR^{11}COR^{12}$, $C_0$-$C_3$alkyl$NR^{11}R^{12}$, $C_1$-$C_3$ alkyl$COR^{11}$, $C_0$-$C_6$ alkyl$COOR^{11}$, $C_0$-$C_6$alkylcyano, —$OC_2$-$C_6$alkylcyano, $C_1$-$C_6$ alkylcycloalkyl, phenyl, —$OC_1$-$C_6$ alkylcycloalkyl, —$OC_1$-$C_6$ alkylaryl, —$OC_1$-$C_6$ alkylheterocyclic, and $C_1$-$C_6$ alkylaryl;
$R^2$ is each independently selected from the group consisting of hydrogen, halo, $C_1$-$C_6$ alkyl, $C_2$-$C_6$ alkenyl, $C_2$-$C_6$ alkynyl, $C_1$-$C_6$ haloalkyl, $OC_1$-$C_6$ alkyl, $C_1$-$C_6$ alkylaryl, aryl, $C_0$-$C_6$ alkyl$NR^7R^8$, heteroaryl, heterocyclyl, $C_3$-$C_8$ cycloalkyl, $C_1$-$C_6$ alkylcycloalkyl and $C_1$-$C_6$ alkylheterocyclyl; wherein each cycloalkyl, aryl, or heterocyclic is optionally substituted with 1 to 3 groups independently selected from oxo, hydroxy, halo, $C_1$-$C_6$ alkyl, $C_2$-$C_6$ alkenyl, $C_2$-$C_6$ alkynyl, $C_1$-$C_6$ alcohol, $C_1$-$C_6$ alkoxy, $C_1$-$C_6$ haloalkyl, $C_1$-$C_6$haloalkoxy, $CONR^{11}R^{12}$, $NR^{11}SO_2R^{12}$, $NR^{11}COR^{12}$, $C_0$-$C_3$ alkyl$NR^{11}R^{12}$, $C_1$-$C_3$ alkyl$COR^{11}$, $C_0$-$C_6$ alkyl$COOR^{11}$, cyano, and phenyl;
$R^3$ is each independently selected from hydrogen, $C_1$-$C_6$ alkyl, aryl, $C_2$-$C_6$ alkenyl, $C_2$-$C_6$ alkynyl, $C_1$-$C_6$ alkylaryl, $C_1$-$C_6$ alkylheterocyclic, $C_3$-$C_8$ cycloalkyl, or $C_1$-$C_6$ alkylcycloalkyl;
$R^4$is a group represented by the formula —$NR^9R^{10}$;
$R^5$ is selected from the group consisting of hydrogen, halogen, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_8$ cycloalkyl, $C_1$-$C_6$ alkylcycloalkyl, $C_1$-$C_6$ alkylaryl, $C_1$-$C_6$ alkylbeterocyclic, aryl, $C_1$-$C_6$ alkylaryl, heteroaryl, aryloxy, —$OC_2$-$C_6$ alkenyl, —$OC_1$-$C_6$ haloalkyl, —$NR^7R^8$, and —$OC_1$-$C_6$ alkylaryl;

and wherein when q is 1, 2 or 3, two adjacent $R^5$ groups may combine to form a fused 5 or 6 member optionally substituted carbocyclic or heterocyclic ring with ring A;

$R^6$ is independently selected from the group consisting of hydrogen, $C_1$-$C_6$ alkyl, $C_2$-$C_6$ alkenyl, hydroxy, $C_1$-$C_6$ alkyl, $C_2$-$C_6$ alkenyl, $C_1$-$C_6$ alkoxy, aryloxy, —$OC_2$-$C_6$ alkenyl, —$OC_1$-$C_6$ haloalkyl, $C_1$-$C_6$ alkylNR$^7R^8$, $C_3$-$C_8$ cycloalkyl, and $C_1$-$C_6$ alkylcycloalkyl;

$R^7$ and $R^8$ are independently selected from the group consisting of hydrogen, $C_1$-$C_6$ alkylcycloalkyl, $C_3$-$C_8$ cycloalkyl, $C_1$-$C_6$ alkylheterocyclic, $C_1$-$C_6$ haloalkyl, NR$^{11}R^{12}$, hydroxy, oxo, COOH, C(O)OC, —$C_4$ alkyl, $C_1$-$C_6$ alkyl, $C_2$-$C_6$ alkenyl, $C_2$-$C_6$ alkynyl, $C_1$-$C_6$ alkoxy, $C_1$-$C_6$ alkylalcohol, $C_1$-$C_6$ alkylamine, $C_1$-$C_6$ alkylaryl, $C_2$-$C_6$ alkenylaryl, $C_2C_6$ alkynylaryl, $C_1$-$C_6$ alkyl-O-$C_1$-$C_6$ alkylaryl, $C_1$-$C_6$ alkyl-NR$^{11}$-$C_1$-$C_6$ alkylaryl, $C_1$-$C_6$ alkylcyano, $C_1$-$C_6$ alkylCONR$^7R^8$, $C_1$-$C_6$ alkylNR$^7R^8$, $C_1$-$C_6$alkylNR$^{11}$COR$^{12}$, and aryl, wherein each cycloalkyl or aryl group is optionally substituted with halo, hydroxy, oxo, amino, COOH, C(O)OC$_1$-$C_4$ alkyl, $C_1$-$C_6$ haloalkyl, $C_1$-$C_6$ alkyl, $C_2$-$C_6$ alkenyl, $C_2$-$C_6$ alkynyl, $C_1$-$C_6$ alkoxy, $C_1$-$C_6$ alkylalcohol, and $C_1$-$C_6$ alkylamine;

or $R^7$ and $R^8$ combine to form a nitrogen containing heterocyclic ring which may have 0, 1, or 2 additional heteroatoms selected from oxygen, nitrogen or sulfur and may be optionally substituted with oxo, or $C_1$-$C_6$ alkyl;

$R^9$ is the group $C_1$-$C_6$ alkyl, $C_2$-$C_6$ alkenyl, $C_3$-$C_8$ cycloalkyl, $C_1$-$C_6$ alkylcycloalkyl, aryl, heterocyclic, $C_1$-$C_6$ alkylheterocyclic, COR$^7$, CO$_2R^7$, $C_0$-$C_3$ alkylCONR$^7R^8$, $C_0$-$C_3$ alkylS(O)$_p$NR$^7R^8$, or $C_0$-$C_3$ alkylS(O)$_pR^7$ wherein $R^7$ is as defined above, and wherein each alkyl, cycloalkyl, aryl, and heterocyclic is optionally substituted with one to two groups independently selected from halo, hydroxy, oxo, COOH, C(O)OC$_1$-$C_4$ alkyl, $C_1$-$C_6$ haloalkyl, $C_1$-$C_6$ alkyl, $C_2$-$C_6$ alkenyl, $C_2$-$C_6$ alkynyl, $C_1$-$C_6$ alkoxy, $C_1$-$C_6$ alkylalcohol, $C_1$-$C_6$ alkylamine, $C_1$-$C_6$ alkylaryl, $C_2$-$C_6$ alkenylaryl, $C_2$-$C_6$ alkynylaryl, $C_1$-$C_6$ alkylheterocyclic, —NR$^7R^8$, $C_3$-$C_8$ cycloalkyl, $C_1$-$C_6$ alkylcycloalkyl, $C_1$-$C_6$ alkyl-O-$C_1$-$C_6$ alkylaryl, $C_1$-$C_6$ alkyl-NR$^{11}$—$C_1$-$C_6$ alkylaryl, $C_1$-$C_6$ alkylcyano, $C_1$-$C_6$ alkylCONR$^7R^8$, $C_1$-$C_6$ alkylNR$^7R^8$, $C_1$-$C_6$alkylNR$^{11}$COR$^2$, and aryl, wherein each cycloalkyl or aryl group is optionally substituted with halo, hydroxy, oxo, amino, COOH, C(O)OC$_1$-$C_4$ alkyl, $C_1$-$C_6$ haloalkyl, $C_1$-$C_6$ alkyl, $C_2$-$C_6$ alkenyl, $C_2$-$C_6$ alkynyl, $C_1$-$C_6$ alkoxy, $C_1$-$C_6$ alkylalcohol, and $C_1$-$C_6$ alkylamine;

$R^{10}$ is selected from the group consisting of aryl, $C_1$-$C_6$ alkylaryl, $C_2$-$C_6$ alkenylaryl, $C_2$-$C_6$ alkynylaryl, $C_1$-$C_6$ haloalkylaryl, $C_1$-$C_6$ alkylheterocyclic, $C_2$-$C_6$ alkenylheterocyclic, $C_1$-$C_6$ alkylcycloalkyl, $C_3$-$C_8$ cycloalkyl, $C_1$-$C_6$ alkyl-O-$C_1$-$C_6$ alkylaryl, and wherein each cycloalkyl, aryl, or heterocyclic group is optionally substituted with 1-3 groups independently selected from the group consisting of hydroxy, oxo, —$C_6$ alkyl, $C_1$-$C_6$ alkyl, $C_1$-$C_6$ alkenyl, $C_1$-$C_6$ alkynyl, $C_1$-$C_6$ haloalkyl, halogen, $C_1$-$C_6$ alkoxy, aryloxy, $C_1$-$C_6$alkenyloxy, $C_1$-$C_6$haloalkoxyalkyl, $C_0$-$C_6$ alkylNR$^{11}R^{12}$, —OC$_1$-$C_6$ alkylaryl, nitro, cyano, —OC$_1$-$C_6$ haloalkyl, $C_1$-$C_6$ haloalkylalcohol, and $C_1$-$C_6$ alkylalcohol;

$R^{11}$ and $R^{12}$ are independently selected from the group consisting of hydrogen, $C_1$-$C_6$ alkyl, $C_1$l-$C_6$ alkenyl, $C_3$-$C_8$ cycloalkyl, heterocyclic, aryl, and $C_1$-$C_6$ alkylaryl, wherein each aryl group is optionally substituted with 1-3 groups independently selected from halogen, $C_1$-$C_6$ alkylheterocyclic, and $C_1$-$C_6$ haloalkyl, or $R^{11}$ and $R^{12}$ combine to form a nitrogen containing heterocyclic ring which may have 0, 1, or 2 additional heteroatoms selected from oxygen, nitrogen or sulfur and is optionally substituted with oxo, or $C_1$-$C_6$ alkyl; or a pharmaceutically acceptable salt, solvate, enantiomer, racemate, diastereomer or mixture of diastereomers thereof.

The present invention also provides a method for modulating or regulating CETP activity comprising the use of a compound of formula I or a pharmaceutically acceptable salt, solvate, enantiomer, racemate, diastereomer or mixture of diastereomers thereof, for the treatment, prevention or amelioration of CETP mediated diseases.

The present invention provides a method for treating or preventing dyslipidemia comprising administering a compound of formula I, pharmaceutically acceptable salt, solvate, enantiomer, racemate, diastereomer, mixture of diastereomers, or prodrug thereof, to a patient in need thereof.

The present invention provides a method for treating or preventing CHD comprising administering a compound of formula I, pharmaceutically acceptable salt, solvate, enantiomer, racemate, diastereomer, mixture of diastereomers, or prodrug thereof, to a patient in need thereof.

The present invention provides a method for treating and/or preventing artherosclerosis comprising administering a compound of formula I, pharmaceutically acceptable salt, solvate, enantiomer, racemate diastereomer, mixture of diastereomers, or prodrug thereof, to a patient in need thereof.

The present invention provides a method for treating and/or preventing diseases related to abnormal CETP activity comprising administering a compound of formula I, pharmaceutically acceptable salt, solvate, enantiomer, racemate diastereomer, mixture of diastereomers, or prodrug thereof, to a patient in need thereof.

The present invention provides a method of raising the ratio of plasma HDL-cholesterol to plasma LDL-cholesterol in a mammal comprising administering a therapeutically effective dose of a compound of formula I, pharmaceutically acceptable salt, solvate, enantiomer, r acemate, diastereomer, mixture of diastereomers, or prodrug thereof, to a patient in need thereof.

The present invention provides a method of raising the level of plasma HDL-cholesterol in a mammal comprising administering a therapeutically effective dose of a compound of formula I, pharmaceutically acceptable salt, solvate, enantiomer, racemate, diastereomer, mixture of diastereomers, or prodrug thereof, to a patient in need thereof.

The present invention provides a method of lowering the level of plasma LDL-cholesterol in a mammal comprising administering a therapeutically effective dose of a compound of formula I, pharmaceutically acceptable salt, solvate, enantiomer, racemate, diastereomer, mixture of diastereomers, or prodrug thereof, to a patient in need thereof.

The present invention also provides a pharmaceutical composition comprising a compound of formula I or a pharmaceutically acceptable salt, solvate, enantiomer, racemate, diastereomer or mixture of diastereomers thereof, and a carrier.

The present invention also provides a method of treating and/or preventing the pathological sequelae due to low levels of plasma HDL and/or high levels of LDL-cholesterol in a mammal comprising administering an effective dose of a compound of formula I, pharmaceutically acceptable salt, solvate, enantiomer, racemate, diastereomer, or mixture of diastereomers, thereof, to a patient in need thereof.

The present invention also relates to the use of a compound of formula I for the manufacture of a medicament for treating and/or preventing atherosclerosis in a mammal comprising administering an effective dose of a compound of formula I, pharmaceutically acceptable salt, solvate, enantiomer, racemate, diastereomer, mixture of diastereomers, or prodrug thereof, to a patient in need thereof.

The present invention also provides a combination therapy involving a compound of formula I and one or more other effective cardio protective agents such as, for example, statins, leptin, and/or other LXR, CETP, ABC A1 or lipid regulating agents useful for the treatment and/or prevention of atherosclerosis.

DETAILED DESCRIPTION OF THE INVENTION

The current invention provides novel compounds of formula I useful in modulating CETP activity.

The terms "modulation" or "regulating" would include, but not be limited to, up-regulation, down-regulation, inhibition, agonism, antagonism of the CETP receptor as appropriate to achieve HDL raising, or LDL lowering and the resulting biological sequelae from such intervention.

The phrase "diseases" or "diseases related to abnormal activity CETP" or "diseases mediated by CETP activity" refers to pathological states where atherosclerosis and/or other cardiovascular diseases are prone because of dyslipidemia and/or other risk factors and are therefore beneficially affected by modulation, particularly down-regulation, of CETP activity. These diseases include but are not limited to hyperlipidemia and its sequelae such as atherosclerosis, CHD, elevated blood pressure, CHF, stroke, hypertension, hypertriglyceremia, diabetes, obesity, inflammatory diseases including but not limited to dermatitis, arthritis, and pain, and diseases of the central nervous system including but not limited to dementia, cognitive disorders such as, for example, Alzheimer's disease.

The term "treatment" bears its usual meaning which includes prohibiting, inhibiting, ameliorating, halting, restraining, slowing or reversing the progression, or reducing the severity of a pathological symptom related to or resultant from the modulation of CETP activity, especially as related to raising plasma levels of HDL, or lowering LDL-cholesterol levels or raising the HDL/LDL ratio or controlling atherosclerosis, hyperlipidemia and/or hypercholesterolemia.

Generally, one of skill in the art is aware that valency must be conserved (complete) for all stable molecules. Therefore, the necessary implication that hydrogen atoms are necessary and available to complete valency in all structures including formula I unless expressly indicated otherwise, is imputed to the general knowledge of one of skill in the art.

General chemical terms used in the description of compounds herein described bear their usual meanings. For example, the term "$C_{1-6}$ alkyl," or "$(C_1-C_6)$alkyl" or "$C_1-C_6$ alkyl" refers to a straight or branched aliphatic chain of 1 to 6 carbon atoms including but not limited to methyl, ethyl, propyl, iso-propyl, n-butyl, pentyl, and hexyl. Unless otherwise stated, the term "alkyl" means $C_1-C_6$ alkyl. Similarly, the term "$C_0-C_6$ alkyl" implies an alkyl group as indicated wherein when the term $C_0$ applies, the alkyl group is not present, and the remaining groups attach directly to the substrate. The invention also contemplates that the term $C_1-C_6$ alkyl or $C_2-C_6$ alkenyl or similar terms also encompass the specified alkyl or alkenyl or similar group, which may be chiral, regio or steroisomeric. Such chiral or regio or stereoisomeric groups are also objects of the present invention.

The term "alkylaryl" refers to an alkyl group substituted by an aryl group. For example, $C_1-C_6$ alkylaryl indicates that a $C_1-C_6$ alkyl group is attached to the aryl group, and that the resulting $C_1-C_6$ alkylaryl is attached to the nucleus via the alkyl group. Preferred alkylaryl group include phenyl ethyl (phenethyl)benzyl.

The term "substituted phenyl" or "optionally substituted phenyl" refers to a phenyl group having one or more substituents selected from the group consisting of $C_1-C_6$ alkyl, $C_1-C_6$ alkoxy, hydroxy, $COR^7$, $—COOR^7$, $C_0-C_6$ alkyl$NR^7R^8$, nitro, chloro, fluoro, bromo, iodo, $C_1-C_6$haloalkyl, $C_1-C_6$ haloalkoxyalkyl, and $—C_0-C_6$ alkylheterocyclic.

The term "optionally substituted carbocyclic or heterocyclic ring" refers to a saturated or unsaturated, aromatic or non-aromatic five or six member ring having optional substituents selected from the group consisting of $C_1-C_6$ alkyl, $C_1-C_6$ alkoxy, hydroxy, $COR^7$, $—COOR^7$, $C_0-C_6$ alkyl$NR^7R^8$, nitro, chloro, fluoro, bromo, iodo, $C_1-C_6$haloalkyl, $C_1-C_6$ haloalkoxyalkyl, and $C_0-C_6$ alkylheterocyclic.

The term "aryl" refers to a substituted or unsubstituted aromatic or heteroaromatic, or heterocyclic radical. Illustrative aryl groups include but is not limited to napthyl, quinolyl, tetrahydroquinolyl, indazolyl, pyrimidinyl, triazinyl, pyrazine, pyridazinyl, piperidyl, pyrrolidinyl, piperazinyl, moipholinyl, tetrahydrofuranyl, pyranyl, tetrazolyl, imidazolyl, 1,2,3-trazolyl, 1,2,4-triazolyl, oxadiazolyl, thiadiazolyl, thiazolyl, oxazolyl, isoxazolyl, isothiazolyl, pyrazolyl, imidazopyridine, benzimidazolyl, triazolone-yl, imidazolone-yl, imidazolidinone-yl, 2-furyl, 3-furyl, 2-thienyl 3-thienyl, 1-pyrrolyl, 2-pyrrolyl, 3-pyrrolyl, phenyl, 2-pyridyl, 3-pyridyl, 4-pyridyl, 1-naphthyl, 2-naphthyl, 2-benzofuryl, 3-benzofuryl, 4-benzofuryl, 5-benzofuryl, 6-benzofuryl, 7-benzofuryl, 2-benzothieny, 3-benzothienyl, 4-benzothienyl, 5-benzothienyl, 6-benzothienyl, 7-benzothienyl, 1-indolyl, 2-indolyl, 3-indolyl, 4-indolyl, 5-indolyl, 6-indolyl, tetrazole, imidazole, isoxazole, pyrazole, 7-indolyl, and isomers thereof. As used herein the term aryl also encompasses the benzyl group.

The term "$C_3-C_8$ cycloalkyl" or similar terms refer to a saturated carbocyclic ring having from 3 to 8 carbon atoms where the term "cycloalkyl" is used a carbocyclic ring having 3 to 8 carbon atoms is implied.

The term "carbocycle" as used herein refers to a cyclic group having only carbon and appropriate number of hydrogen atoms. The term encompasses groups such as cycloalkyl, cycloalkene, cycloalkylene, naphthyl, phenyl and the like.

The term "heterocycle", "heterocyclyl", or "heterocyclic" refers to a 5, 6, 7, 8, 9 or 10 member saturated, partially unsaturated, or aromatic, mono-cyclic or a bicyclic ring containing 1-5 heteroatoms selected from N, S or O, wherein said heterocycle is optionally substituted at carbon or nitrogen atom(s) unless otherwise specified. Most preferred heterocyclic groups include pyridinyl, pyrolidinyl, piperidinyl, hexamethyleneimmino, morpholino, thiophene, indolyl, quinolyl, isoquinolyl, and tetrazolyl.

As a corollary, the term "alkylheterocyclic" or "alkylheterocycle" is understood to mean that the alkyl group is attached to the heterocycle and the point of attachment to the molecular backbone or nucleus is the alkyl group. The term "alkyl" without a qualifier implies a $C_1-C_6$ alkyl group.

The term "haloalkoxyalkyl" as used herein include for example trifluoromethoxy, pentafluoroethoxy, trifluoroethoxy ($OCH_2CF_3$) and the like.

The term "Prodrugs" describes derivatives of the compounds of the invention that have chemically or metabolically cleavable groups and become by solvolysis or under physiological conditions the compounds of the invention, which are pharmaceutically active, in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy. In some cases it is desirable to prepare double ester type prodrugs such as (acyloxy) alkyl esters or ((alkoxycarbonyl)oxy)alkyl esters.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, 3$^{rd}$ edition, Greene, T. W.; Wuts, P.G.M. Eds., John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base or acid addition salts of compounds of the present invention. Base addition salts include for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laureate, maleate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate. Preferred salts for the purpose of the invention include the hydrochloride salt, the hydrobromide salt, the bisulfate salt, the methane sulfonic acid salt, the p-toluenesulfonic acid salt, bitartrate, the acetate and the citrate salt.

A compound of the invention as illustrated by formula I may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereo-specific reactions with starting materials that contain the asymmetric centers and are already resolved. Alternatively desired stereoisomers may be prepared by methods that lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

PREFRERRED EMBODIMENTS OF THE INVENTION

Preferred n, p, and q
Preferably n is 0, or 1. More preferably, n is 0.
Preferably p is 1, or 2.
Preferably, q is 0, 1 or 2. More preferably q is 0 or 1.

Preferred A Ring
A preferred a ring is selected from the group consisting of pyridine, pyrimidine, pyrazine, pyridazine, 1,2,5-triazine, thiophene, furan, pyrrole, pyrazole, isoxazole, isothiazole, imidazole, oxazole, thiazole, and 1,2,3-triazole. More preferred is an A ring selected from the group consisting of pyridine, pyrazine, thiophene, pyrazole, isoxazole, oxazole, and thiazole. Most preferred A ring is pyridine.

Preferred $R^1$
A preferred $R^1$ group when n is 0, and k is C=O is selected from the group consisting of —$OC_1$-$C_6$ alkyl, —$OC_3$-$C_8$ cycloalkyl, —$OC_1$-$C_6$ alkylcycloalkyl, —$OC_1$-$C_6$ alkylcycloalkylNR$^7$R$^8$, —$OC_0$-$C_6$ alkylaryl, , —$OC_1$-$C_6$ haloalkyl , —$OC_1$-$C_6$alkylcyano, —$OC_1$-$C_6$alkylCO$_2$R$^{11}$, —$OC_1$-$C_6$alkylhydroxy, —$OC_3$-$C_8$ cycloalkylCO$_2$R$^{11}$, —$OC_1$-$C_6$ alkylNR$^7$R$^8$ and —$OC_1$-$C_6$ alkylheterocyclic. More preferred group for when $R^1$ when n is 0, and k is C=O, is selected —$OC_1$-$C_6$ alkylaryl, $OC_1$-$C_6$ alkyl, —$OC_0$-$C_6$ alkylaryl, —$OC_1$-$C_3$ alkylcycloalkyl, —$OC_0$-$C_3$ alkylheterocyclic, —$OC_1$-$C_6$alkylcyano, —$OC_1$-$C_6$alkylCO$_2$R$^{11}$, —$OC_1$-$C_6$alkylhydroxy, —$OC_1$-$C_6$ alkylNR$^7$R$^8$ and —$OC_0$-$C_6$ alkylcycloalkylNR$^7$R$^8$ A preferred R1 group when n is 1, 2 or 3 and K is a bond, is selected from the group consisting of cycloalkyl, aryl, heterocyclic, wherein each cycloalkyl, aryl, or heterocyclic is optionally substituted with 1 or 2 groups selected from $C_1$-$C_3$ alkylalcohol, $C_1$-$C_3$ alkylamine, COOH, CONH$_2$, and C(O)OC$_1$-$C_3$ alkyl.

Preferred $R^2$

A preferred $R^2$ groups is selected from the group consisting of hydrogen, $C_1$-$C_6$ alkyl, hydroxy, $C_1$-$C_6$ haloalkyl, halo, $C_1$-$C_6$ alkylhalide, —$C_1$-$C_6$ alkylcycloaryl, —$C_3$-$C_8$ cycloalkyl, $C_1$-$C_6$ alkylaryl, —$OC_1$-$C_6$ alkyl, —$OC_1$-$C_6$ haloalkyl, —$OC_1$-$C_5$ alkylcycloalkyl, $C_0$-$C_6$ alkyl$NR^7R^8$, —$OC_1$-$C_6$ alkylaryl, —$C_1$-$C_6$ alkylheterocyclic, and —$OC_1$-$C_6$ alkylheterocyclic. More preferred is an R group selected from hydroxy, $C_1$-$C_6$ alkyl, halo, —$C_3$-$C_8$ cycloalkyl, $C_1$-$C_6$ alkylaryl and $C_1$-$C_6$ alkoxyalkyl. Most preferred is an $R^2$ group represented by hydrogen, —$C_3$-$C_8$ cycloalkyl, or $C_1$-$C_6$ alkyl.

Preferred $R^3$ Groups

Preferably $R^3$ is hydrogen.

Preferred $R^4$ Groups

A preferred is $R^4$ is represented by the group —$NR^9R^{10}$ that is further represented by a group selected from the group consisting of:

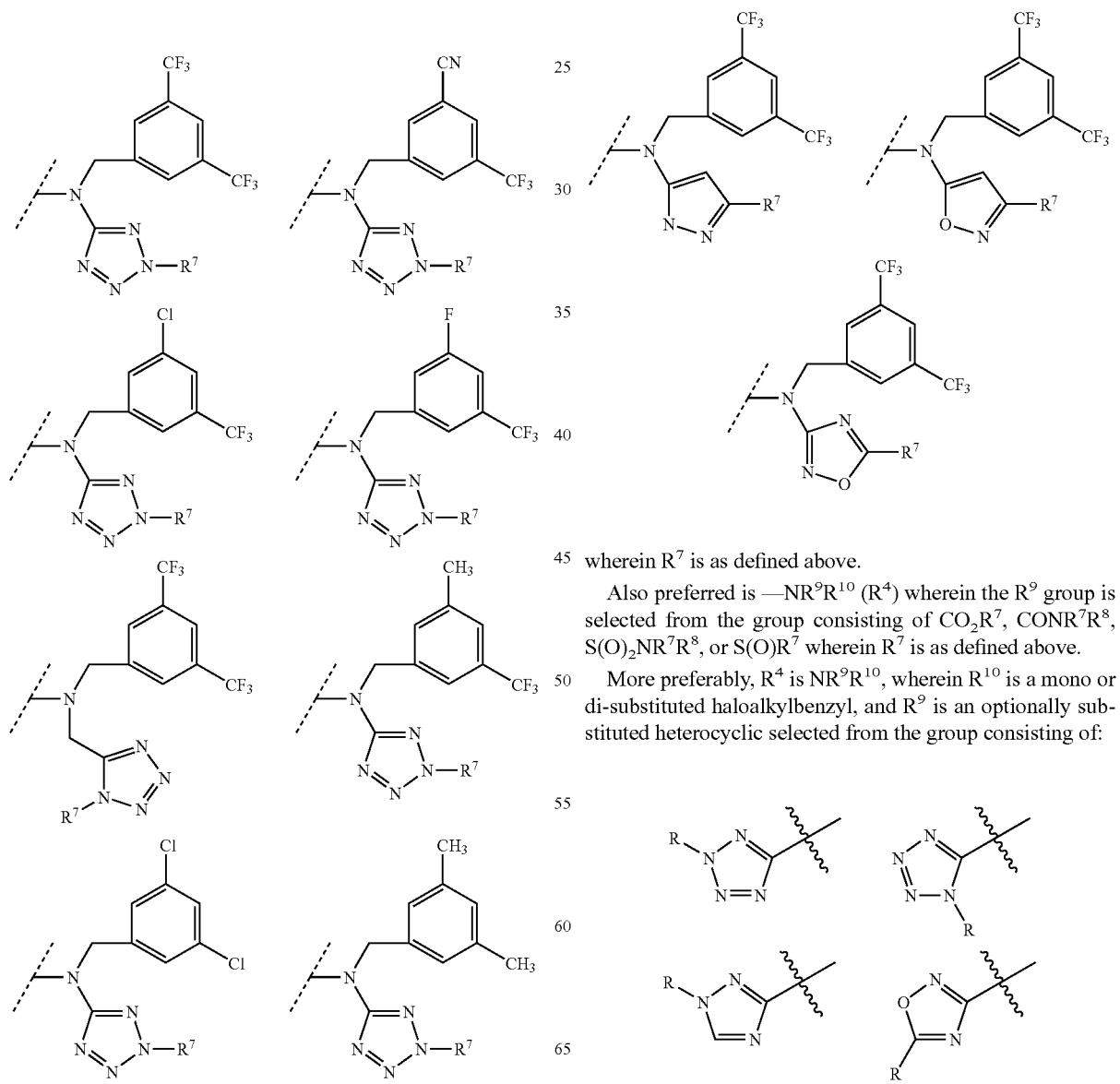

wherein $R^7$ is as defined above.

Also preferred is —$NR^9R^{10}$ ($R^4$) wherein the $R^9$ group is selected from the group consisting of $CO_2R^7$, $CONR^7R^8$, $S(O)_2NR^7R^8$, or $S(O)R^7$ wherein $R^7$ is as defined above.

More preferably, $R^4$ is $NR^9R^{10}$, wherein $R^{10}$ is a mono or di-substituted haloalkylbenzyl, and $R^9$ is an optionally substituted heterocyclic selected from the group consisting of:

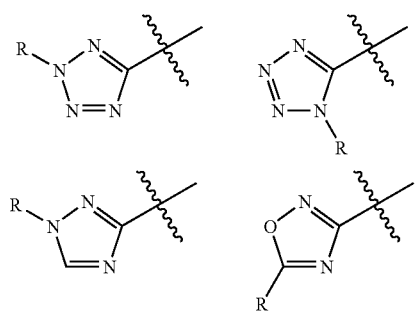

-continued

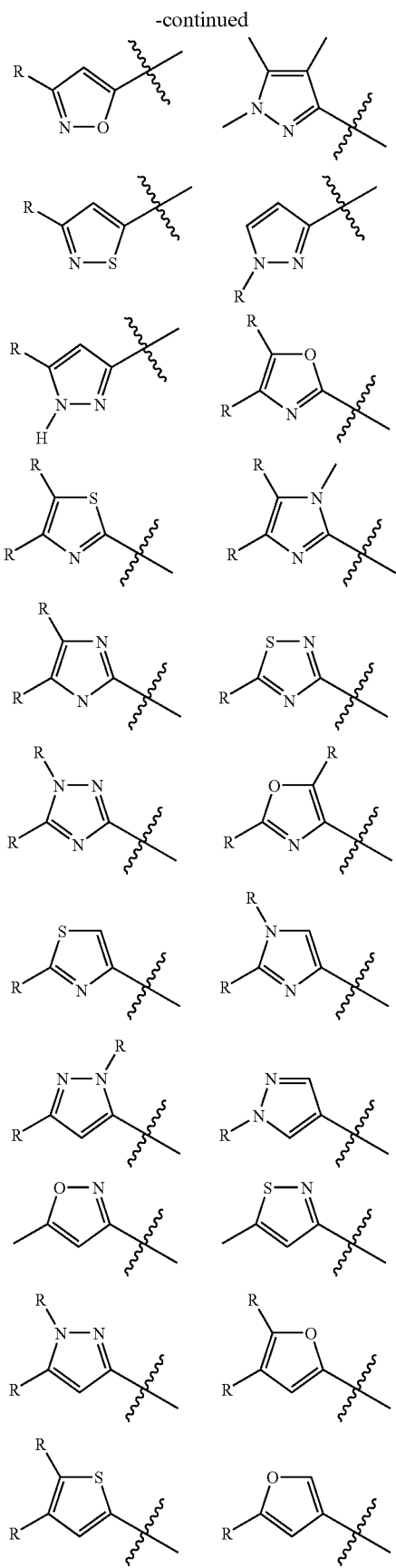

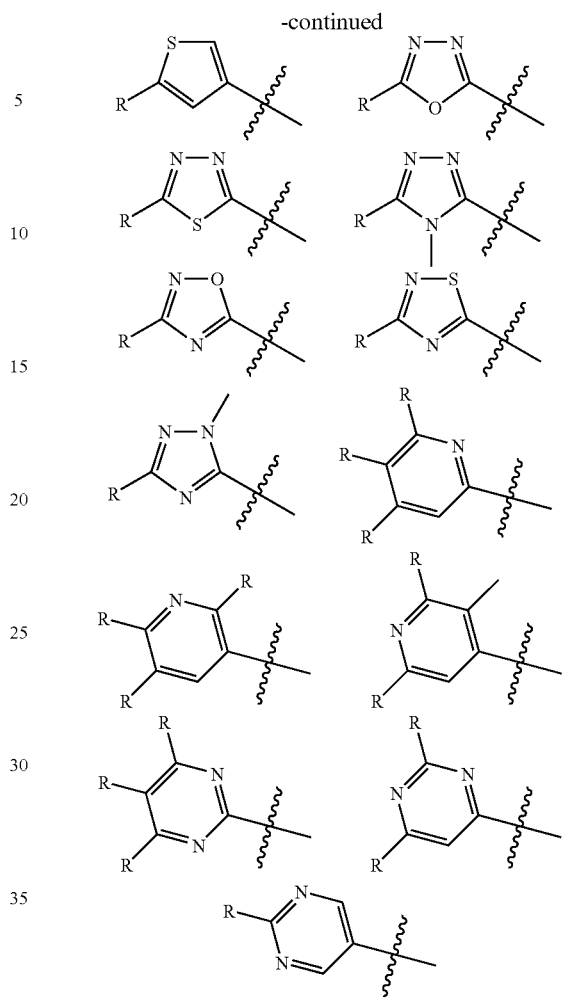

wherein R is independently H, OH, NR⁷R⁸ or $C_1$-$C_3$ alkyl wherein $C_1$-$C_3$ alkyl group is optionally substituted with OH, halo, cyano, CONR⁷R⁸, CO₂R¹¹, or NR⁷R⁸.

Preferred R⁵ Groups

R⁵ is preferably selected from a group consisting of hydrogen, halogen, hydroxy, $C_1$-$C_6$ haloalkyl, $C_1$-$C_6$ alkyl, $C_1$-$C_6$ alkenyl, $C_1$-$C_6$ alkylheterocyclcic, $C_1$-$C_6$ alkylaryl, aryl, $C_1$-$C_6$ alkoxy, aryloxy, —OC₂-$C_6$ alkenyl, —OC₁-$C_6$ haloalkyl, —NR⁷R⁸, —CH₂NR⁷R⁸, CN, —COOH, and NO₂;

More preferably, R⁵ is at each occurrence independently selected from the group consisting of hydrogen, halogen, $C_1$-$C_6$ alkyl, $C_1$-$C_6$ haloalkyl, -NR⁷R⁸ and $C_1$-$C_6$ alkoxy.

Preferred R⁶

R⁶ is preferably selected from a group consisting of hydrogen, $C_2$-$C_6$ haloalkyl, $C_1$-$C_6$ alkyl, and $C_1$-$C_6$ alkenyl.

Preferred R⁷ and R⁸

Preferred R⁷ and R⁸ are independently selected from the group consisting of hydrogen, $C_1$-$C_6$ alkyl, $C_2$-$C_6$ alkenyl, $C_1$-$C_6$ alkylaryl, and $C_1$-$C_6$alkylheterocyclic, wherein each aryl group is optionally substituted with 1-3 groups independently selected from $C_1$-$C_6$ alkyl, halo, and $C_1$-$C_6$ haloalkyl.

Preferred R¹¹ and R¹²

Preferred R¹¹ and R¹² are independently selected from a group consisting of hydrogen, $C_1$-$C_6$ alkyl, $C_2$-$C_6$ alkenyl, $C_1$-$C_6$ alkylaryl, and $C_1$-$C_6$alkylheterocyclic, wherein each aryl group is optionally substituted with 1-3 groups independently selected from $C_1$-$C_6$ alkyl, halo, and $C_1$-$C_6$ haloalkyl.

A most preferred compound of the invention is a compound selected from the group consisting of:

4-[Acetyl-(3,5-bis-tifluoromethyl-benzyl)-amino]-2-ethyl-7-methyl-3,4-dihydro-2H-[1,8]naphthyridine-1-carboxylic acid isopropyl ester, Cis-4-[acetyl-(3,5-bis-trifluoromethyl-benzyl)-amino]-2-ethyl-6-methoxy-3,4-dihydro-2H-[1,5]naphthyridine-1-carboxylic acid isopropyl ester, Cis-4-[(3,5-bis-trifluoromethyl-benzyl)-(2H-tetrazol-5-yl)-amino]-2-ethyl-6-methoxy-3,4-dihydro-2H-[1,5]naphthyridine-1-carboxylic acid isopropyl ester, Cis-4-[(3,5-bis-tifluoromethyl-benzyl)-(2-methyl-2H-tetrazol-5-yl)-amino]-2-ethyl-6-methoxy-3,4-dihydro-2H-[1,5]naphthyridine-1-carboxylic acid isopropyl ester, 7-[Acetyl-(3,5-bis-trifluoromethyl-benzyl)-amino]-5-ethyl-6,7-dihydro-5H-thieno[3,2-b]pyridine-4-carboxylic acid isopropyl ester, (+/−)-cis-4-[Acetyl-(3,5-bis-trifluoromethyl-benzyl)-amino]-2-ethyl-6-trifluoromethyl-3,4-dihydro-2H-[1,5]naphthyridine-1-carboxylic acid isopropyl ester, (+/−)-cis-4-[Acetyl-(3,5-bis-trifluoromethyl-benzyl)-amino]-2-ethyl-6-bromo-3,4-dihydro-2H-[1,5]naphthyridine-1-carboxylic acid isopropyl ester, (+/−)-cis-4-[Acetyl-(3,5-bis-trifluoromethyl-benzyl)-amino]-2-ethyl-6-dimethylamino-3,4-dihydro-2H-[1,5]naphthyridine-1-carboxylic acid isopropyl ester, (+/−)-cis-4-[Acetyl-(3,5-bis-trifluoromethyl-benzyl)-amino]-2-ethyl-6-methyl-3,4-dihydro-2H-[1,5]naphthyridine-1-carboxylic acid isopropyl ester, (+/−)-cis-4-[(3,5-Bis-trifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester, (2S,4R)-4-[(3,5-Bis-trifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester, (2R,4S)-4-[(3,5-Bis-tifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester, (+/−)-cis-4-[(3,5-Bis-trifluoromethyl-benzyl)-[2-(2-tert-butoxycarbonylamino-ethyl)-2H-tetrazol-5-yl)-amino]-2-ethyl-6-trifluoromethyl-3,4-dihydro-2H-[1,5]naphthyridine-1-carboxylic acid isopropyl ester, (+/−)-cis-4-[[2-(2-Amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester, (2S,4R)-cis-4-[[2-(2-Amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester, (2R,4S)-cis-4-[[2-(2-Amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester, (+/−)-cis and trans-4-[(3,5-Bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester, (2R,4S)-4-[(3,5-Bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester, (2S,4R)-4-[(3,5-Bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester, (+/−)-4-[(3,5-Bis-trifluoromethyl-benzyl)-[2-methyl-2H-tetrazol-5-yl)-amino]-2-ethyl-6-trifluoromethyl-3,4-dihydro-2H-[1,5]naphthyridine-1-carboxylic acid isopropyl ester, (2R,4S)-4-[(3,5-Bis-trifluoromethyl-benzyl)-[2-methyl-2H-tetrazol-5-yl)-amino]-2-ethyl-6-trifluoromethyl-3,4-dihydro-2H-[1,5]naphthyridine-]-carboxylic acid isopropyl ester trifluoroacetate, (2S,4R)-4-[(3,5-Bis-trifluoromethyl-benzyl)-[2-methyl-2H-tetrazol-5-yl)-amino]-2-ethyl-6-trifluoromethyl-3,4-dihydro-2H-[1,5]naphthyridine-1-carboxylic acid isopropyl ester trifluoroacetate, (+/−)-cis-4-[[2-(2-Amino-ethyl)-2H-tetrazol-5-yl]-(3,5-bis-trifluoromethyl-benzyl)-amino]-2-ethyl-6-methyl-3,4-dihydro-2H-[1,5]naphthyridine-1-carboxylic acid isopropyl ester, (+/−)-cis-4-[(3,5-Bis-trifluoromethyl-benzyl)-[2-(2-hydroxy-ethyl)-2H-tetrazol-5-yl)-amino]-2-ethyl-6-methyl-3,4-dihydro-2H-[1,5]naphthyridine-1-carboxylic acid isopropyl ester, (+/−)-cis-6-Amino-4-[(3,5-bis-trifluoromethyl-benzyl)-[2-methyl-2H-tetrazol-5-yl)-amino]-2-ethyl-7-methyl-3,4-dihydro-2H-[1,5]naphthyridine-1-carboxylic acid isopropyl ester, (+/−)-trans-6-Amino-4-[(3,5-bis-trifluoromethyl-benzyl)-(2-methyl-2H-tetrazol-5-yl)-amino]-2-ethyl-7-methyl-3,4-dihydro-2H-[1,5]naphthyridine-1-carboxylic acid isopropyl ester, (+/−)-cis-4-[(3,5-Bis-trifluoromethyl-benzyl)-(2-methyl-2H-tetrazol-5-yl)-amino]-2-ethyl-6-methoxy-7-methyl-3,4-dihydro-2H-[1,5]naphthyridine-1-carboxylic acid isopropyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid ethyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-dimethylamino-ethyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid tetrahydro-pyran-4-yl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 1-methyl-piperidin-4-yl ester, (2R,3'R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid tetrahydro-furan-3-yl ester, (2R,3'S,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid tetrahydro-furan-3-yl ester, (2R,4S)-4-[(3,5-Bis-trifluoromethyl-benzyl)-(2-menthyl-2H-tetrazol-5-yl)-amino]-2-ethyl-6-trifluoromethyl-3,4-dihydro-2H-[1,5]naphthyridine-1-carboxylic acid 2-morpholin-4-yl-ethyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-(4-methyl-piperazin-1-yl)-ethyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-methoxycarbonyl-2-methyl-propyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-carboxy-2-methyl-propyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-cyano-ethyl ester, (2R,4S)-4-[(3,5-Bis-trifluoromethyl-benzyl)-(2-methyl-2H-tetrazol-S-yl)-amino]-2-ethyl-6-trifluoromethyl-3,4-dihydro-2H-[1,5]naphthyridine-1-carboxylic acid 2-(2H-tetrazol-5-yl)-ethyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-benzyloxy-ethyl ester, (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-hydroxy-ethyl ester, (+/−)-cis-4-[(3,5-Bistrifluoromethylbenzyl)-(5-methyl-1H-pyrazol-3-yl)amino]-2-ethyl-6-trifluoromethyl-3,4-dihydro-2H-[1,5]naphthyridine-1-carboxylic acid isopropyl ester, (+/−)-cis-4-[(3,5-Bis-trifluoromethylbenzyl)-(3-methyl-isoxazol-5-yl)-amino]-2-ethyl-6-trifluoromethyl-3,4-dihydro-2H-[1,5]naphthyridine-1-carboxylic acid isopropyl ester, (+/−)-cis-4-[(3,5-Bis-trifluoromethyl-benzyl)-(5-methyl-[1,2,4]oxadiazol-3-yl)-amino]-2-ethyl-6-trifluoromethyl-3,4-dihydro-2H-[1,5]naphthyridine-1-carboxylic acid isopropyl ester, (+/−)-cis-4-[(3,5-Bis-trifluoromethyl-benzyl)-(2,5-dimethyl-2H-pyrazole-3-carbonyl)-amino]-2-ethyl-6-trifluoromethyl-3,4-dihydro-2H-quinoline-1-carboxylic acid isopropyl ester, (+/−)-cis-4-(3,5-Bis-trifluoromethyl-benzyl)-1-(cyclopentylmethyl-2-ethyl-6-methoxy-1,2,3,4-tetrahydro-[1,5]naphthyridine-4-yl)-acetamide, (+/−)-cis-4-[Acetyl-(3,5-bis-trifluoromethyl-benzyl)-amino]-6-methoxy-2-methyl-3,4-dihydro-2H-[1,5]naphthyridine-1-carboxylic acid isopropyl ester, (+/−)-cis-4-[(3,5-Bis-trifluoromethyl-benzyl)-ethoxycarbonyl-amino]-6-methoxy-2-methyl-3,4-dihydro-2H-[1,5]naphthyridine-1-carboxylic acid isopropyl ester, (+/−)-cis-4-[(3,5-Bis-trifluoromethyl-benzyl)-(3-fluoro-5-trifluoromethyl-benzoyl)-amino]-6-methoxy-2-methyl-3,4-dihydro-2H-[1,5]naphthyridine-1-carboxylic acid isopropyl ester, (+/−)-cis-N-(3,5-Bis-trifluoromethyl-benzyl)-N-(1-cyclopentyl-6-methoxy-2-methyl-1,2,3,4-tetrahydro-[1,5]napthyridin-4-yl)-acetamide, (+/−)-cis-4-[Acetyl-(3,5-bis-trifluoromethyl-benzyl)-amino]-2-methyl-6-trifluoromethyl-3,4-dihydro-2H-[1,5]naphthyridine-1-carboxylic acid isopropyl ester, (+/−)-cis-4-[Acetyl-(3,5-bis-trifluoromethyl-benzyl)-amino]-2-cyclopropyl-6-trifluoromethyl-3,4-dihydro-2H-[1,5]naphthyridine-1-carboxylic acid isopropyl ester, (+/−)-cis-4-[(3,5-Bis-trifluoromethyl-benzyl)-(2methyl-2H-tetrazole-5-yl)-amino]-2-cyclopropyl-6-trifluoromethyl-3,4-dihydro-2H-[1,5]naphthyridine-1-carboxylic acid isopropyl ester, 4-[(3,5-Bis-trifluoromethyl-benzyl)-(5,6,7,8-tetrahydro-quinolin-3-yl)-amino]-2,3-dimethyl-3,4,6,7,8,9-hexahydro-2H-benzo[b][1,5]napthyridine-1-carboxylic acid isopropyl ester, (2R,4S)-4-[(3,5-Bis-trifluoromethyl-benzyl)-(2-methyl-2H-tetrazol-5-yl)-amino]-2-ethyl-6-methyl-3,4-dihydro-2H-[1,5]naphthyridine-1-carboxylic acid methyl ester, (2R,4S)-4-[(3,5-Bis-tifluoromethyl-benzyl)-(2-methyl-2H-tetrazol-5-yl)-aniino]-2-ethyl-6-methyl-3,4-dihydro-2H-[1,5]naphthyridine-1-carboxylic acid ethyl ester, (2R,4S)-4-[(3,5-Bis-trifluoromethyl-benzyl)-(2-methyl-2H-tetrazol-5-yl)-amino]-2,6-dimethyl-3,4-dihydro-2H-[1,5]naphthyridine-1-carboxylic acid methyl ester, (2R,4S)-4-[(3,5-Bis-trifluoromethyl-benzyl)-(2-methyl-2H-tetrazol-5-yl)-amino]-2,6-dimethyl-3,4-dihydro-2H-[1,5]naphthyridine-1-carboxylic acid ethyl ester, (2R,4S)-4-[(3,5-Bis-trifluoromethyl-benzyl)-(2-methyl-2H-tetrazol-5-yl)-amino]-2,6-dimethyl-3,4-dihydro-2H-[1,5]naphthyridine-1-carboxylic acid isopropyl ester, (2R,4S)-4-[(3-Cyano-5-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid isopropyl ester, (2R,4S)-4-[(3,5-Dichloro-benzyl)-(2-methyl-2H-tetrazol-5-yl)-amino]-2-ethyl-6-trifluoromethyl-3,4-dihydro-2H-[1,5]naphthyridine-1-carboxylic acid isopropyl ester, (2R,4S)-4-[(3-Chloro-5-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid isopropyl ester, (2R,4S)-2-Ethyl-4-[(3-fluoro-5-trifluoromethyl-benzyl)-(2-methyl-2H-tetrazol-5-yl)-amino]-6-trifluoromethyl-3,4-dihydro-2H-[1,5]naphthyridine-1-carboxylic acid isopropyl ester, (2R,4S)-4-[(3,5-Dimethyl-benzyl)-(2-methyl-2H-tetrazol-5-yl)-amino]-2-ethyl-6-trifluoromethyl-3,4-dihydro-2H-[1,5]naphthyridine-1-carboxylic acid isopropyl ester, (2R,4S)-4-[(3,5-Difluoro-benzyl)-(2-methyl-2H-tetrazol-5-yl)-amino]-2-ethyl-6-trifluoromethyl-3,4-dihydro-2H-[1,5]naphthyridine-1-carboxylic acid isopropyl ester, (2R,4S)-4-[[2-(2-Amino-ethyl)-2H-tetrazol-5-yl]-(3,5-bis-trifluoromethyl-benzyl)-amino]-2-ethyl-6-methyl-3,4-dihydro-2H-[1,5]naphthyridine-1-carboxylic acid methyl ester, (2R,4S)-4-{(3,5-Bis-trifluoromethyl-benzyl)-[2-(2-hydroxy-ethyl)-2H-tetrazol-5-yl]-amino }-2-ethyl-6-methyl-3,4-dihydro-2H-[1,5]naphthyridine-1-carboxylic acid methyl ester, (2R,4S)-4-[[2-(2-Amino-ethyl)-2H-tetrazol-5-yl]-(3,5-bis-trifluoromethyl-benzyl)-amino]-2-ethyl-6-methyl-3,4-dihydro-2H-[1,5]naphthyridine-1-carboxylic acid ethyl ester, (2R,4S)-4-{(3,5-Bis-trifluoromethyl-benzyl)-[2-(2-hydroxy-ethyl)-2H-tetrazol-5-yl]-amino}-2-ethyl-6-methyl-3,4-dihydro-2H-[1,5]naphthyridine-1-carboxylic acid ethyl ester, (2R,4S)-4-[[2-(2-Amino-ethyl)-2H-tetrazol-5-yl]-(3-cyano-5-trifluoromethyl-benzyl)-amino]-2-ethyl-6-trifluoromethyl-3,4-dihydro-2H-[1,5]naphthyridine-1-carboxylic acid isopropyl ester, (2R,4S)-4-{(3-Cyano-5-trifluoromethyl-benzyl)-[2-(2-hydroxy-ethyl)-2H-tetrazol-5-yl]-amino}-2-ethyl-6-trifluoromethyl-3,4-dihydro-2H-[1,5]naphthyridine-1-carboxylic acid isopropyl ester, or a pharmaceutically acceptable salt, solvate enantiomer or diastereomer or mixture thereof.

The positional isomers issues, and geometric isomers associated with the asymmetric carbon atoms of compounds of formula I are also contemplated to be within the scope of the current invention as useful for the treatment of diseases related to CETP modulation.

Synthesis of Compounds of the Invention

The compounds of the instant invention can be synthesized as exemplified in the schemes below. Aryl amino ester intermediates of Formula 1 can be chemically prepared, for example, by following the synthetic routes set forth in the Schemes below. However, the following discussion is not intended to be limiting to the scope of the present invention in any way. The reagents and starting materials are readily available to one of ordinary skill in the art. Other necessary reagents and starting materials may be made by procedures which are selected from standard techniques of organic and heterocyclic chemistry, techniques which are analogous to the syntheses of known structurally similar intermediates or starting materials and the procedures described in the preparations and examples below, including any novel procedures. Such known procedures include, but are not limited to, esterification of a carboxylic acid, hydrolysis of a nitrile to a carboxylic acid, and subsequent esterification. In addition, one of ordinary skill will appreciate that many of the necessary reagents or starting materials can be readily obtained from commercial suppliers or custom synthesis groups. The R, $R^1$, $R^2$, $R^3$, $R^4$, $R^5$, $R^6$, W, X, Y, Z, etc, used within this section for the purpose of illustrating the various methods of synthesizing compounds of the invention are not necessarily synonymous in scope or meaning with similar groups used in the generic structure for compounds of formula I, assuming W, X, Y, Z do not all equal carbon. However, groups in similar positions are co-extensive in scope and meaning compared to groups occupying similar positions as defined for the generic structure of compounds of formula I.

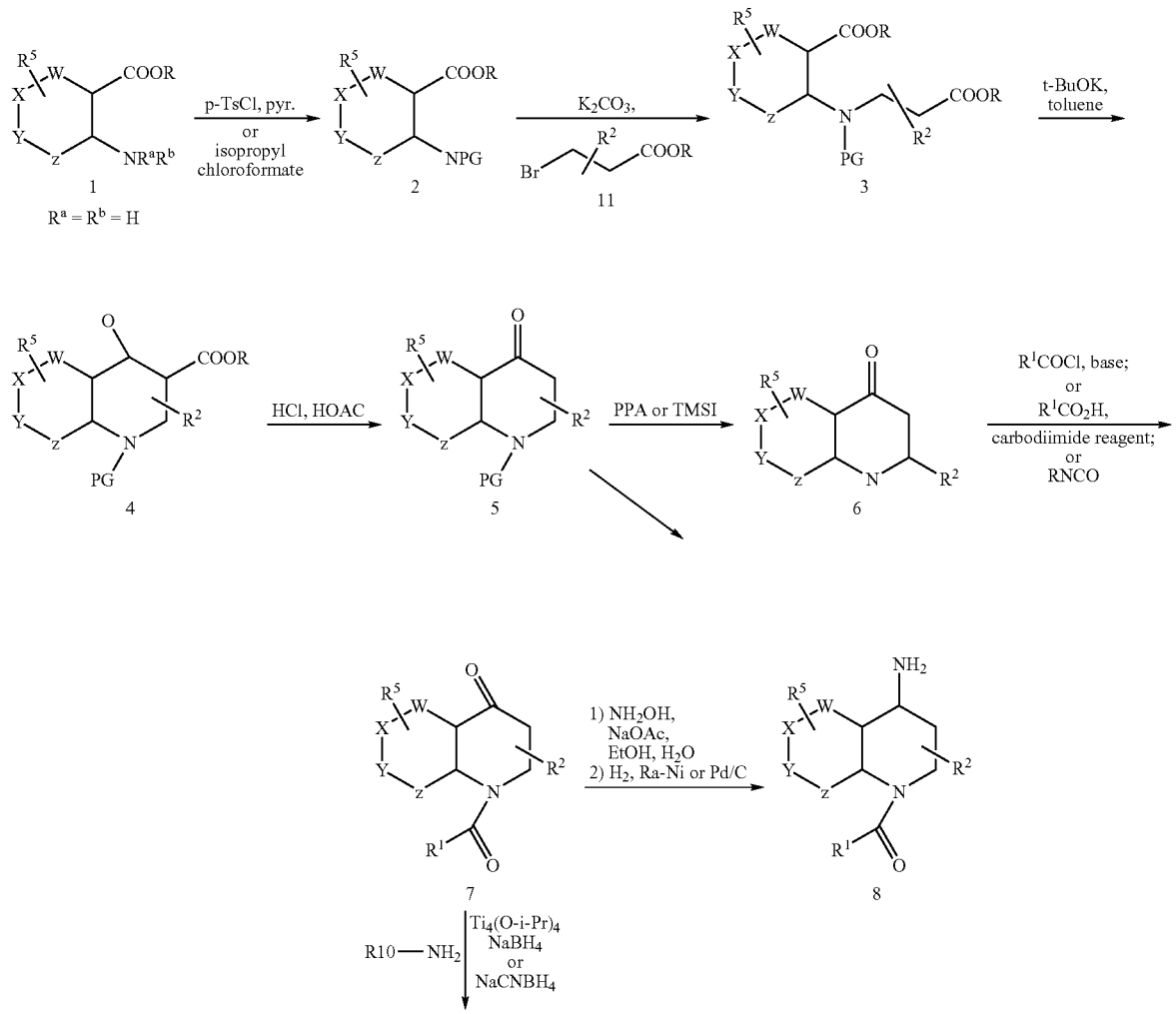

Scheme 1

-continued

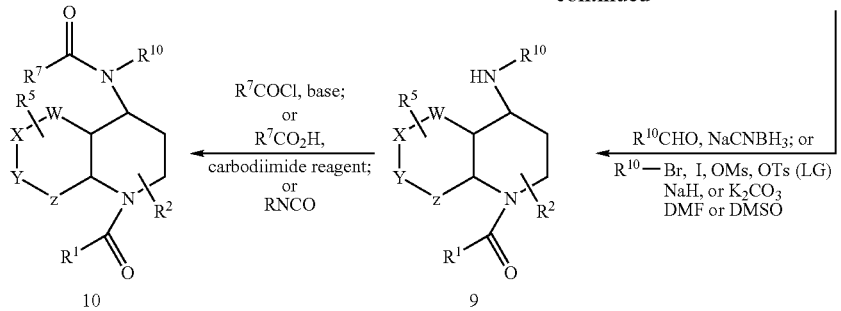

Synthetic scheme 1 shows preparation of compounds of formula I wherein and n is 0. For example, substituted heteroarylamino esters 1 that are either commercially available or prepared as set forth in the literature or in Schemes 1a to 1d can be protected with tosyl chloride, isopropyl chloroformate, or other suitable protecting group to provide 2. The compound 2 may in turn be alkylated with appropriately substituted; or unsubstituted 3-bromoethylesters 11 thus affording 3. Dieckmann condensation-cyclization of intermediate 3 yields N-protected naphthyridine 4, which is subjected to acid hydrolysis and decarboxylation to afford ketone derivatives 5. Removal of the protecting group, if necessary, with acid (e.g. PPA (polyphosphoric acid)), TMSI (trimethylsilyliodide), or HCl provides the intermediate 6. Alternatively, utilizing the same conditions to effect 7 to 8, one can proceed directly to 8 without deprotection.

N-acylation of 6 by treatment with an appropriately substituted aryl or alkyl chloroformate in the presence of an organic base such as pyridine affords carbamates of structure 7. Alternatively, treatment of 6 with an acid chloride or an appropriate activated ester, such as those generated in-situ from the reaction of an appropriately substituted aryl or alkyl carboxylic acid affords compounds of formula 7.

Generation of urea derivatives from 6 is accomplished by treatment with a carbamoyl chloride in the presence of base such as pyridine and DMAP (dimethylamino pyridine) or an alternative base such as NaH in DMF. Alternatively, treatment with phosgene, or carbodiimide (CDI) reagent such as cyclohexylcarbodiimide or analog thereof, followed by the addition of an appropriately di-substituted amine will afford ureas of structure 7. Formation of sulfonamide derivatives from 6 can be accomplished by reaction with appropriately substituted sulfonyl chlorides in the presence of a base. Conversion of ketone 7 to 10 may be performed through direct reductive amination with an appropriately substituted alkylamine or aryl amine to afford compound 9. Alternatively, compound 9 may be prepared through formation of the amine derivate 8 by reduction of an intermediate oxime, followed by alkylation with an appropriately substituted benzylic halide, mesylate or tosylate, or by reductive alkylation with the appropriate aldehyde or ketone in the presence of a reducing reagent such as NaCNBH$_3$. Compound 9 is converted to 10 (a compound of the invention) by acylation with an appropriately substituted symmetrical anhydride or acid halides to afford amides. Reaction of compound 9 with chloroformates affords the corresponding carbamates, Reaction of 9 with isocyanates, carbamoyl chlorides, or appropriately substituted sulfonyl chlorides affords the corresponding urea or sulfonamides respectively.

Intermediates useful for the practice of the invention may be prepared following the procedures of schemes 1a to 1e described below and/or minor variations thereof known to one of skill in the art.

Scheme 1a

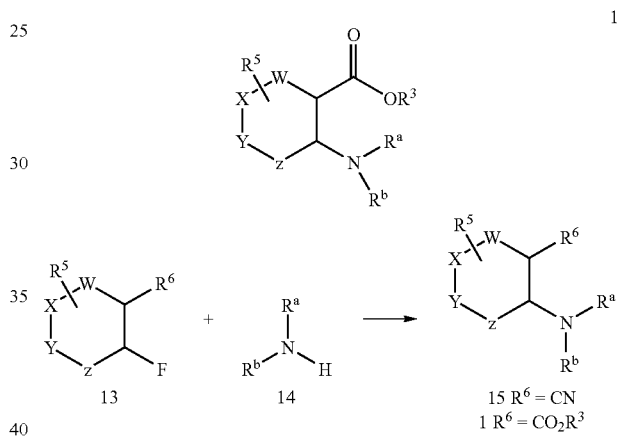

In scheme 1 a, the nucleophilic aromatic substitution occurs by methods known in the art, (Wells, K. M. et al. Tetrahedron Letters, 1996, 37(36), 6439-6442). The appropriately substituted amine 14, such as benzylamine, is dissolved in a suitable solvent, such as DMF or DMSO. A base such as cesium carbonate is added. The appropriately substituted fluoro heterobenzoate or heterobenzonitrile 13 (R$^6$=CN or CO$_2$R$^3$), such as methyl fluoronicotinate ester is also added. The reaction proceeds at 0° C. to elevated (up to about 150° C.) temperatures in anywhere from ten minutes to several days depending on the stability of the starting materials. The product of structure 15 (R$^6$=CN) or 1 (R$^6$=CO$_2$R$_3$) can then be isolated by a standard aqueous workup, followed by normal phase chromatographic methods or recrystallization techniques commonly employed in the art.

Scheme 1b

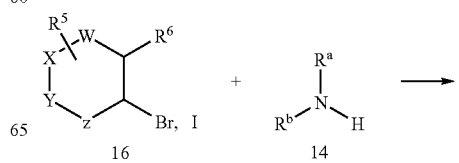

-continued

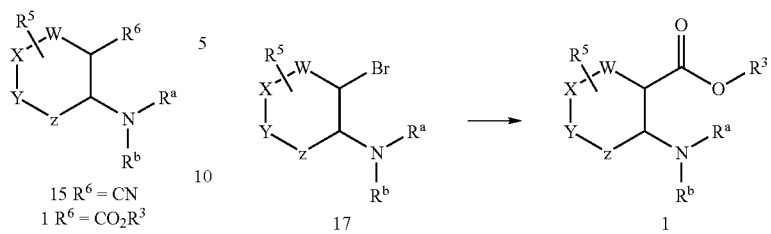

15 R⁶ = CN
1 R⁶ = CO₂R³

Scheme 1d

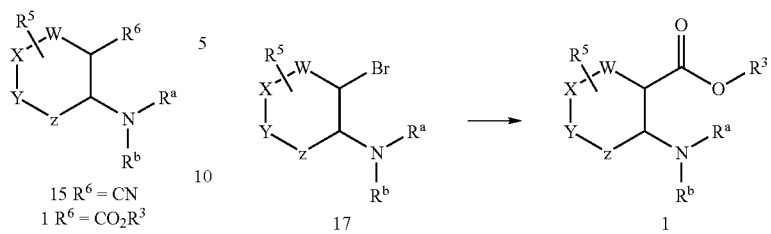

In scheme 1b, the N-heteroaryl coupling occurs by methods known in the art, (Hartwig, J. F. et al. Angew. Chem., Int. Ed. Engl. 1998, 37, 2046-2067). The appropriately substituted amine 14 is dissolved in a suitable solvent, such as DMF. A base, such as cesium carbonate or sodium tert-butoxide, the appropriately substituted halogenated heterobenzoate or heterobenzonitrile 16 ($R^6$=CN or $CO_2R^3$), and a suitable catalyst complex, such as palladium acetate and diphenyl phospino ferrocene ligand are added. The reaction proceeds at 0° C. to elevated temperatures (up to 150° C.) in anywhere from ten minutes to several days depending on the stability of the starting materials. The product of structure 15 ($R^6$=CN) or 1 ($R^6$=$CO_2R^3$) can then be isolated by a standard aqueous workup, followed by normal phase chromatographic methods or recrystallization techniques commonly employed in the art.

In scheme 1d, the aromatic carboxylation occurs by methods known in the art, (Boger, D. L. et al, Journal of Organic Chemistry, 1994, 59(17), 4943-4949, Volpin et al, *Organomet. Reactions,* 1975, 5, 313-386). The appropriately substituted heteroaryl bromide 17 is dissolved in a suitable solvent, such as diethyl ether or tetrahydrofuran. An alkyl lithium, such as n-butyl lithium or tert-butyl lithium or magnesium turnings is added. The resulting anion is quenched with a suitable carbon dioxide source, such as dry ice, or dimethyl carbonate. The reaction proceeds at −78° C. to room temperature in anywhere from about five minutes to several hours depending on the stability of the starting materials. The product of structure 1 can then be isolated by a standard aqueous workup, followed by normal phase chromatographic methods or recrystallization techniques commonly employed in the art.

Scheme 1c

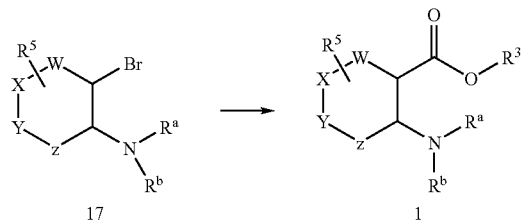

Scheme 1e

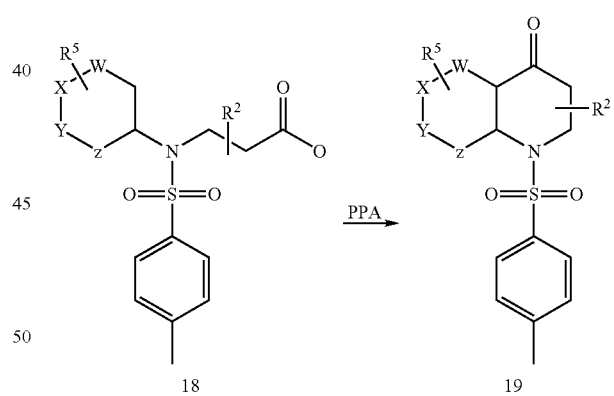

In scheme 1c, the carbonylation occurs by methods known in the art, (Heck, *Palliadium Reagents in Organic Synthlesis;* Academic Press: New York, 1985, p. 348-358). The appropriately substituted heteroaryl bromide 17 is dissolved in a suitable solvent, such as DMF, followed by addition of a base, such as cesium carbonate or sodium tert-butoxide/ A suitable catalyst complex, such as palladium acetate and diphenyl phospino ferrocene, an appropriate alcohol ($R^3$—OH) are added. The reaction mixture is then saturated with carbon monoxide. The reaction proceeds at 0° C. to elevated temperatures (up to about 150° C.) in anywhere from ten minutes to several days depending on the stability of the starting materials. The reaction may also be preformed under pressure using procedures known to one of skill in the art. The product of structure 1 may then be isolated by a standard aqueous workup, optionally followed by normal phase chromatographic methods or recrystallization techniques commonly employed in the art.

The ketone intermediate 19 may be prepared following the procedure of Scheme 1e. (see also Booker-Milburn, K. I., et al.; *J. Chem. Soc., Perkin Trans.* 1, 3261-3273 (1997)). N-(p-tolylsulfonyl)-3-aminopropanoic acids can be made by alkylation of the appropriate heterocyclic amine via a procedure similar to that shown in Scheme 1 and then saponification of the resulting ester to yield compound 18. Compound 18 may then undergo an intermolecular acylation to form the 4-keto quinolin-4-one 19, using a variety of procedures known in the art.

Compounds of formula I may be prepared according to scheme 2 below.

Scheme 2
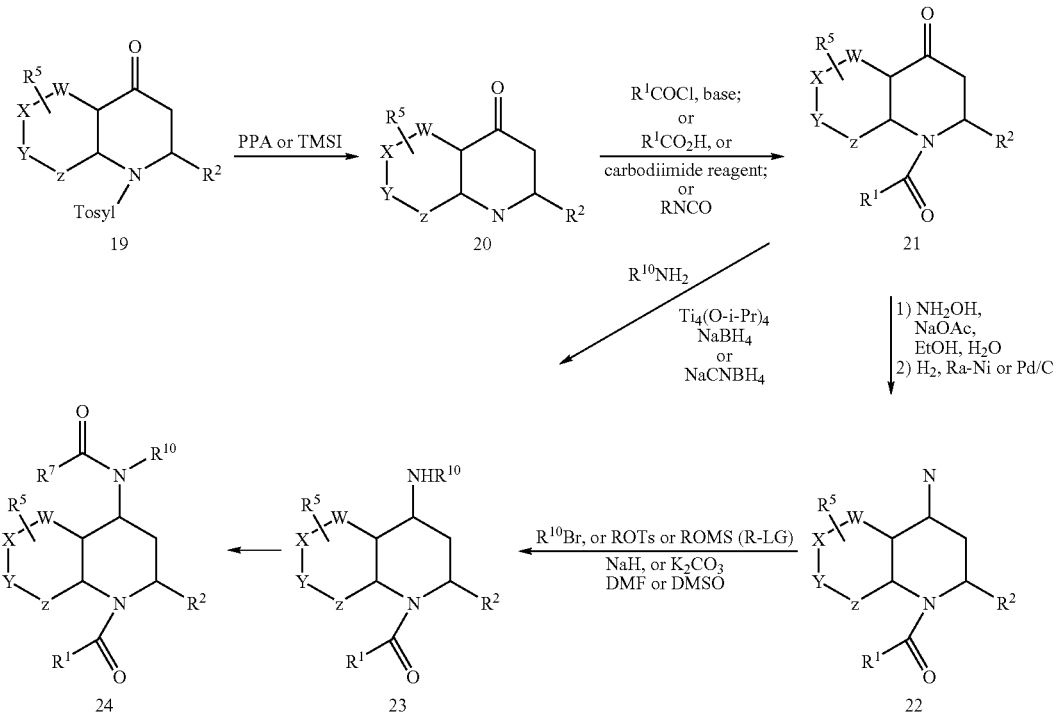
As shown in Scheme 2, intermediates of general structure 19 (prepared in Scheme 1e) are converted to 23 (a compound of the invention) utilizing conditions similar to those described in Scheme 1.
Compounds of formula I may be prepared according to scheme 3 below.
Scheme 3
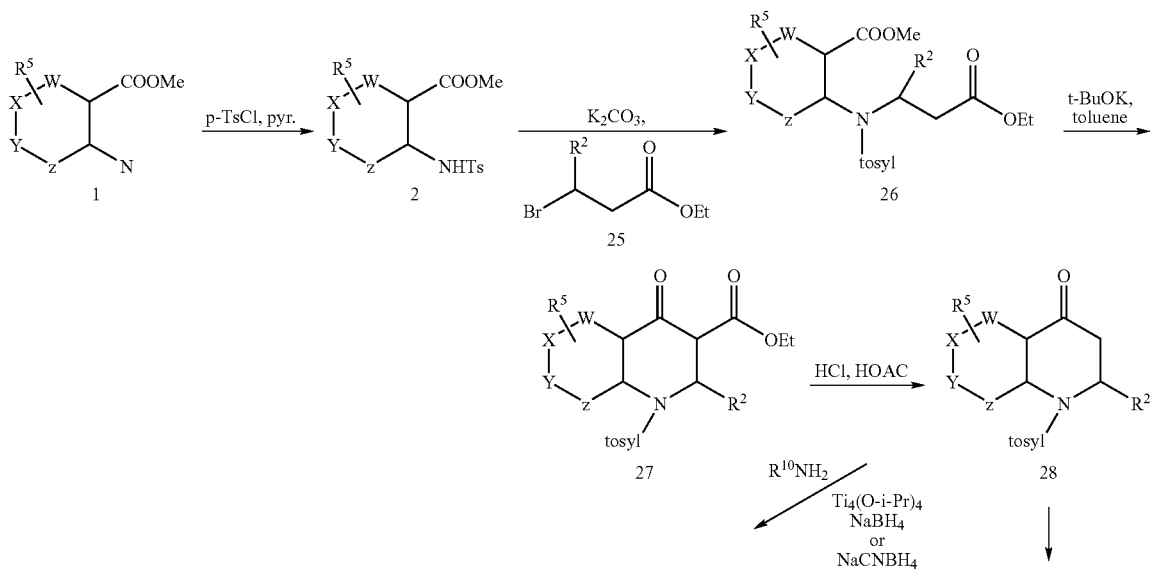

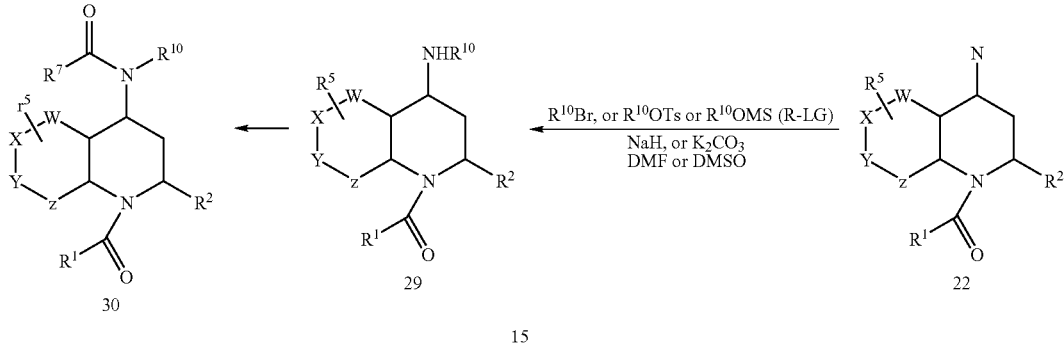

As shown in Scheme 3 intermediates of general structure 1 such as for example 2-aminopyridine 3-methylcarboxylate, are converted to 30 (a compound of the invention) utilizing conditions similar to those described in Scheme 1.

Compounds of the invention such as 8 can be prepared according to Scheme 4.

Scheme 4

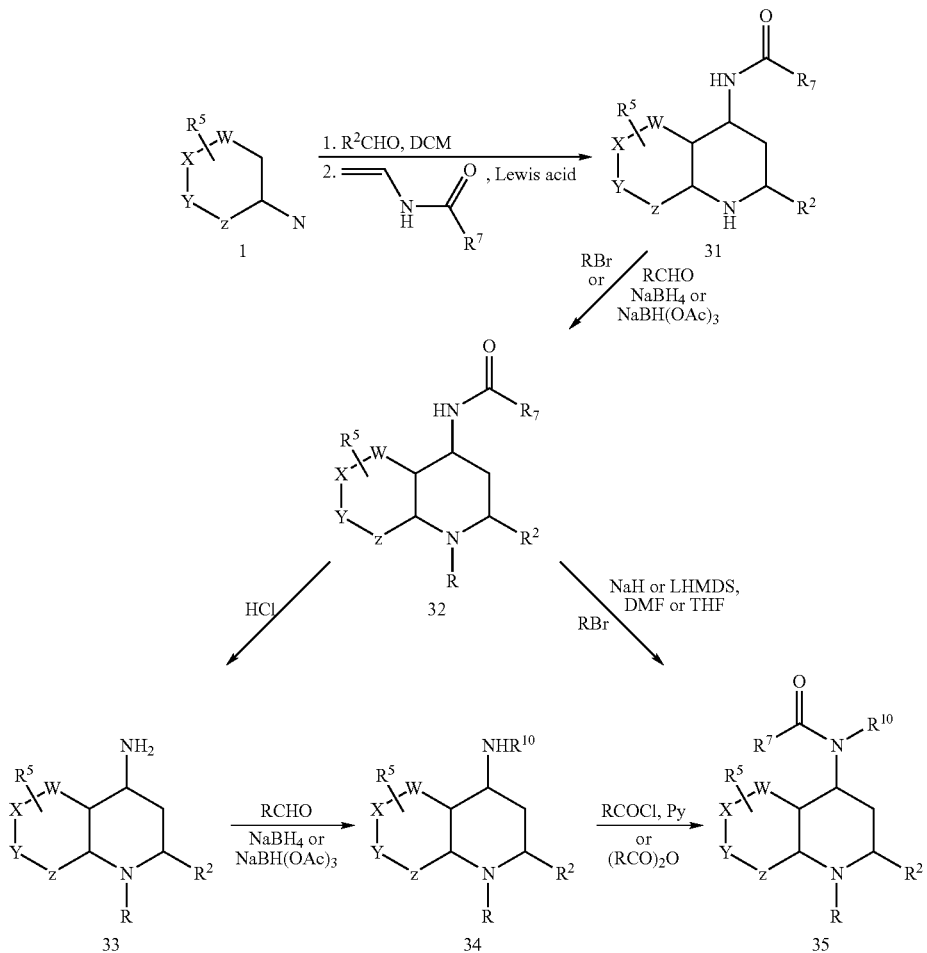

As shown in Scheme 34, heteroaryl amine 1 such as for example 2-methoxy-5-aminopyridine, can be converted to 31 by reaction of the appropriate aldehyde or ketone, followed by treatment with an N-acylated enamine in the presence of acid. Reductive amination, or alkylation provides 32, a compound of the invention, which can be further functionalized at the N-4 nitrogen by amide hydrolysis to give 33, which in turn is alkylated via reductive amination to provide 34. Compound 34 may be acylated or sulfonylated using standard procedures by one skilled in the art to provide 35. Alternatively amide 32 may be directly alkylated using an appropriate alkyl halide, alkyl tosylate, or the like, in the presence of base to provide 35.

Alternatively, compounds of the present invention may also be prepared according to Scheme 5 or known variations thereof.

Scheme 5

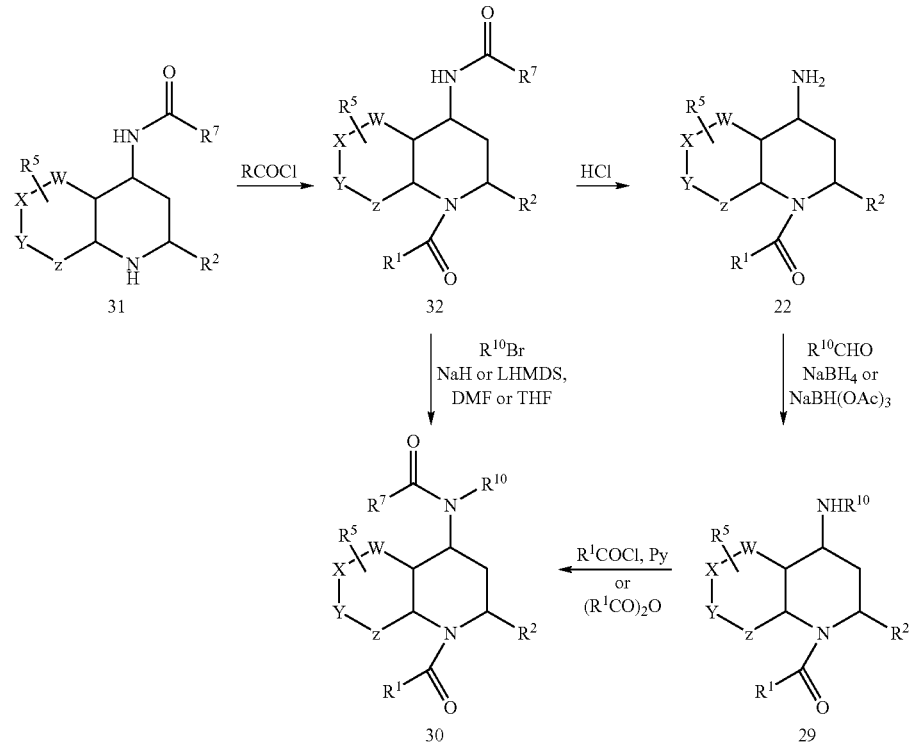

Compound 31 is acylated to provide compound 32, which in turn is selectively hydrolysed to afford amine 22. Compound 32 can be alkylated using an appropriate alkyl halide, alkyl tosylate, or the like, in the presence of base to provide 30. Alternatively, 22 can be alkylated using reductive amination conditions to afford 29, which in turn may be acylated or sufonylated to afford 30.

Certain compounds of formula I may be prepared as shown in Scheme 6.

Scheme 6

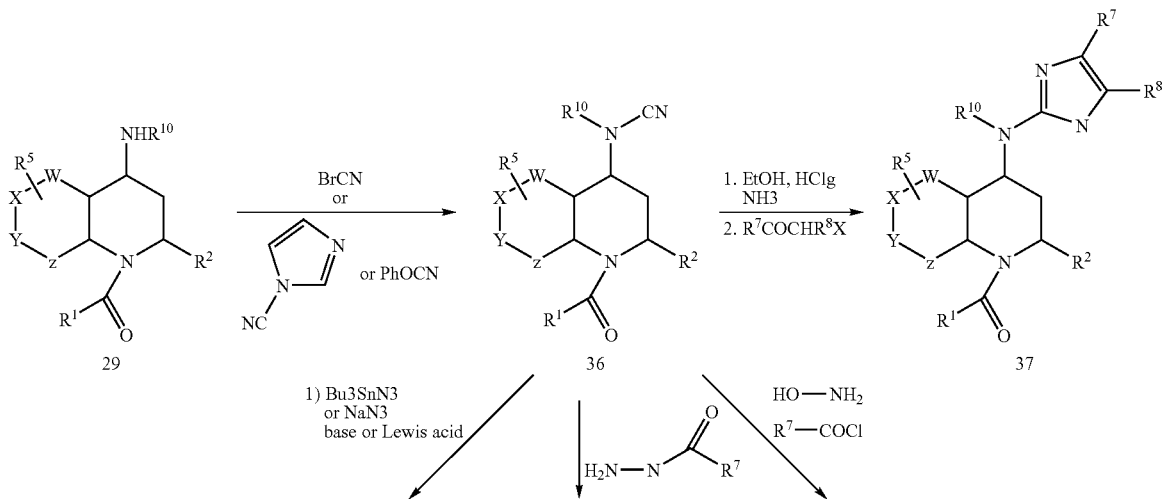

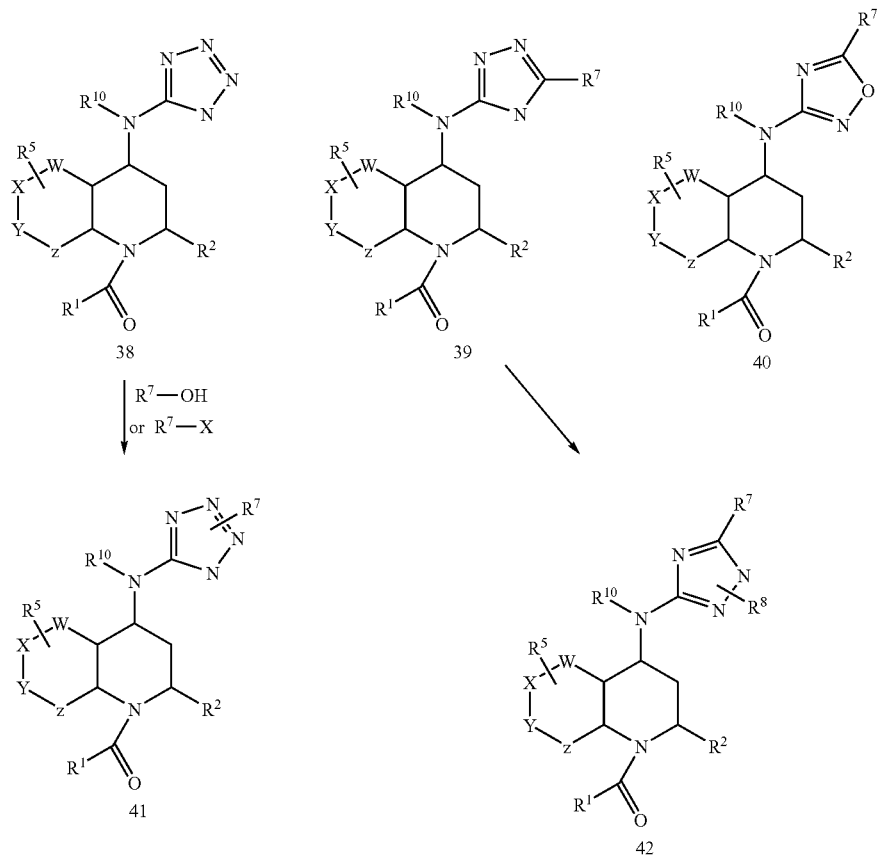

As shown in Scheme 6, amine 29 can be treated with for example cyanogen bromide or N-cyano imidazole in the presence or absence of base to form the N-cyano derivative 36. The synthesis of imidazole 37, tetrazole 38, triazole 39 and oxadiazole 40 is illustrated in the scheme. Tetrazole 89 can be alkylated using the appropriate alcohol under Mitsunobu conditions, or with the appropriate alkyl iodide, mesylate, or the like in the presence of base to provide 41. Triazole 39 can be alkylated using an appropriate alkyl iodide, mesylate, or the like in the presence of base to afford 42.

Scheme 7

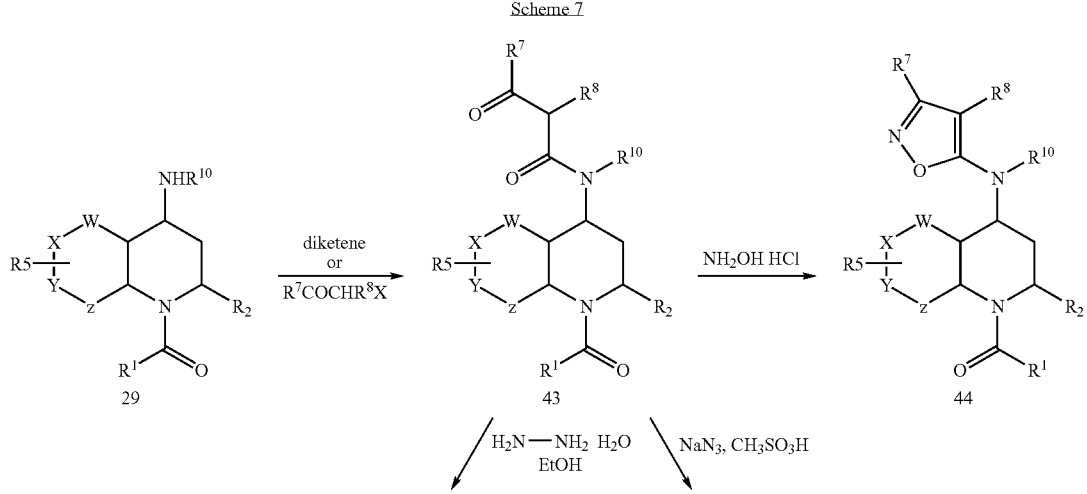

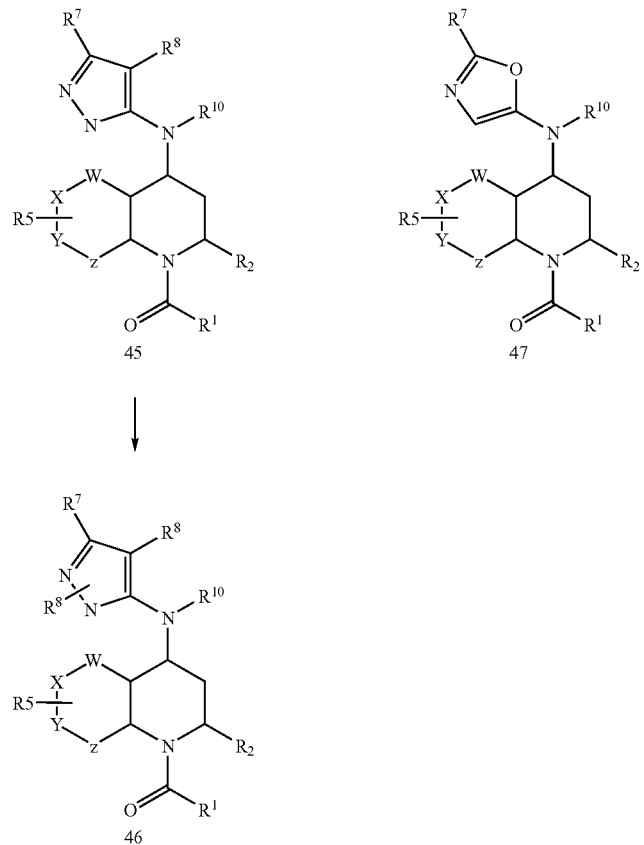

As shown in scheme 7 compound 29 can be transformed to compound 43 by reaction with diketene or a α-haloketone, further treatment with hydroxylamine hydrochloride can afford isoxazole 44. Alternatively 43 can react with hydrazine in a solvent such as ethanol to afford pyrazole 45 that can be alkylated or acylated to afford compound 46.

Alternatively compound 43 can be converted into the oxazole 47 by tratment with sodium azide and methanesulfonic acid.

Scheme 8

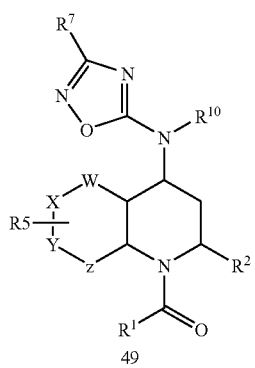

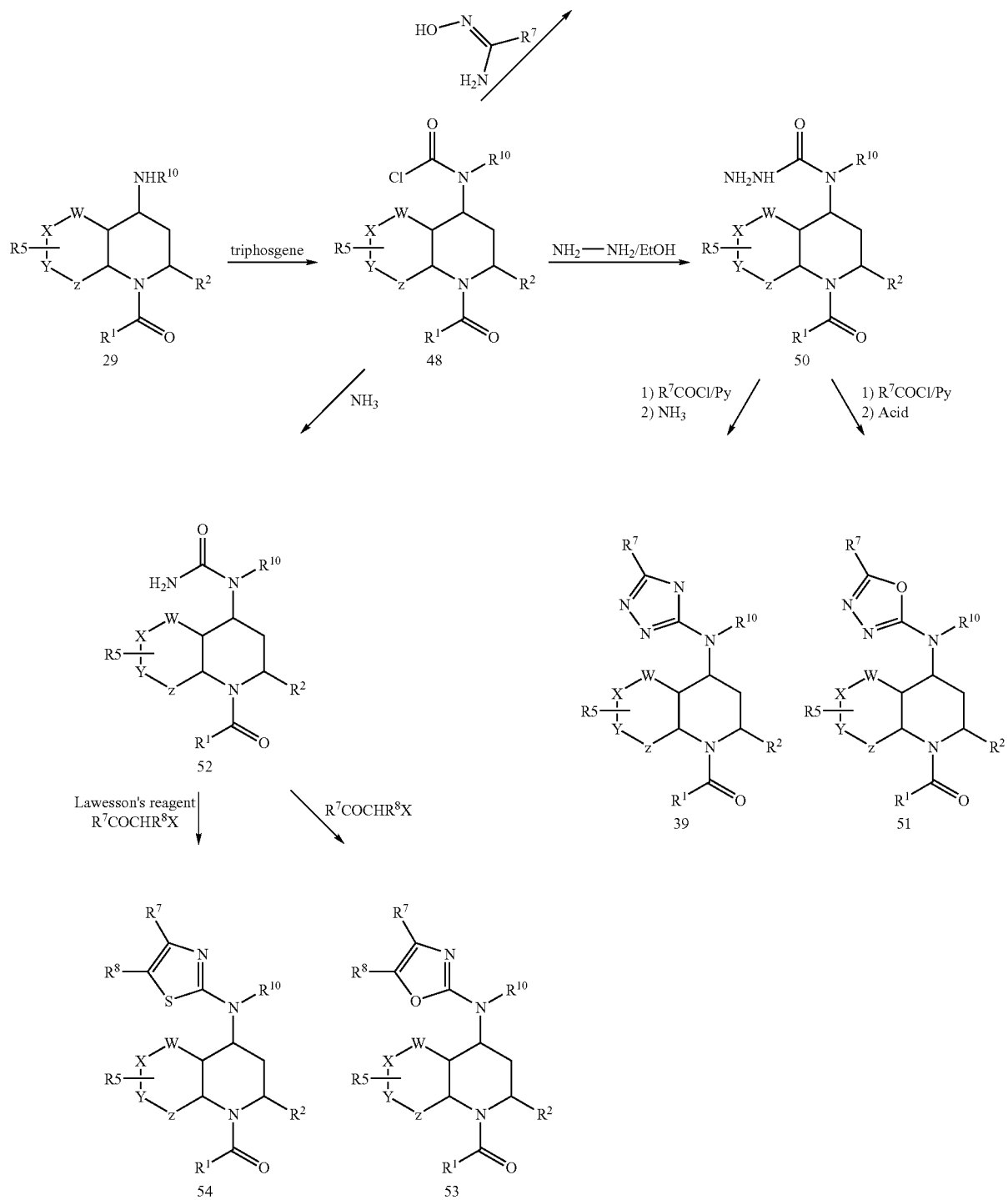

As shown in scheme 8, secondary amine 29 can be transformed to the acyl chloride 48 by treatment with triphosgene. Compound 48 may be converted into the oxadiazole 49 by reaction with an appropriate amidoxime. Alternatively 48 can be reacted with hydrazine to yield compound 50. Compound 50 upon treatment with an appropriate acyl chloride in the presence of ammonia affords triazole 39 or in the presence of acid such as sulfuric acid and water affords the oxadiazole 51. Compound 48 can be treated with ammonia to yield the ureido derivative 52 that can be transformed into oxazole 53 by reaction with an α-haloketone in the presence of a base. Alternatively compound 52 can be converted to the corresponding thioamide with Lawesson's reagent and which then reacts with a α-haloketone can afford the thiazole 54.

Scheme 9
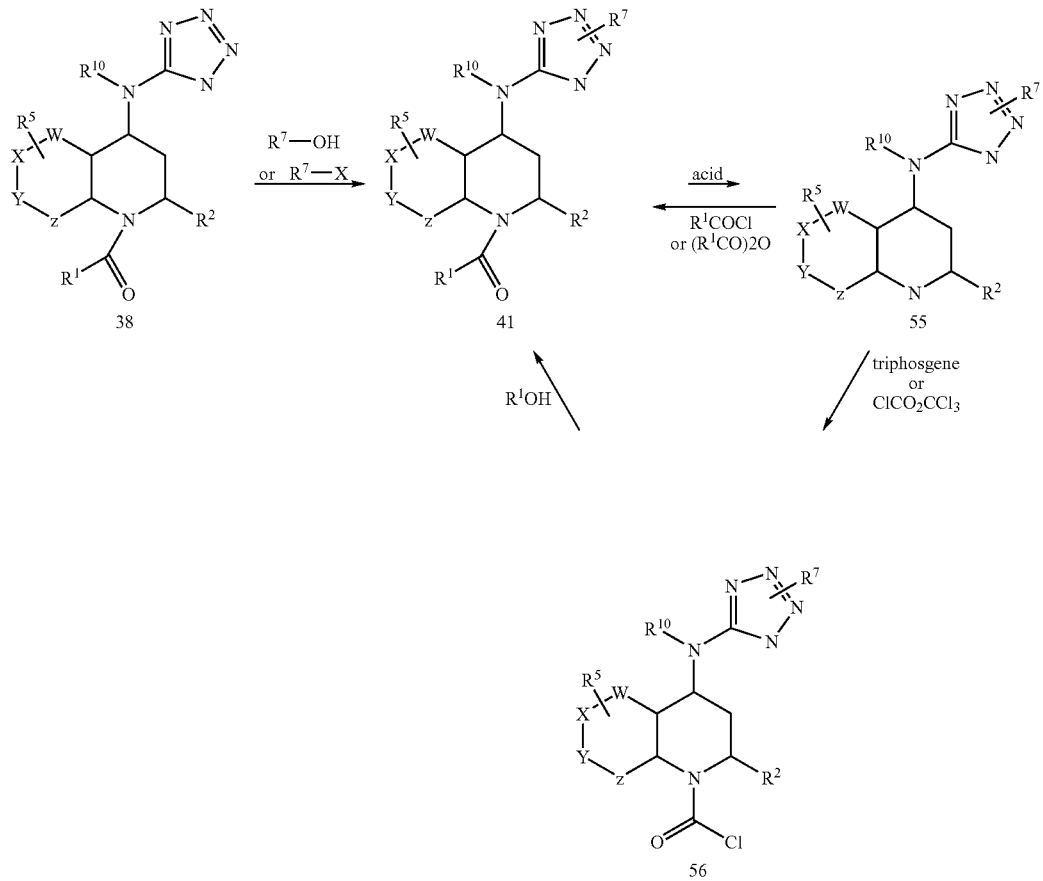
As shown in scheme 9, compound 41 may be hydrolyzed to the corresponding amine 55, and may be further acylated using standard procedures by one skilled in the art to provide 41. Or alteratively 55 can be treated with triphosgene or trichloromethylchoroformate to provide 56. Compound 56 can afford compound 41 by reaction with the appropriate alcohols.
Scheme 10
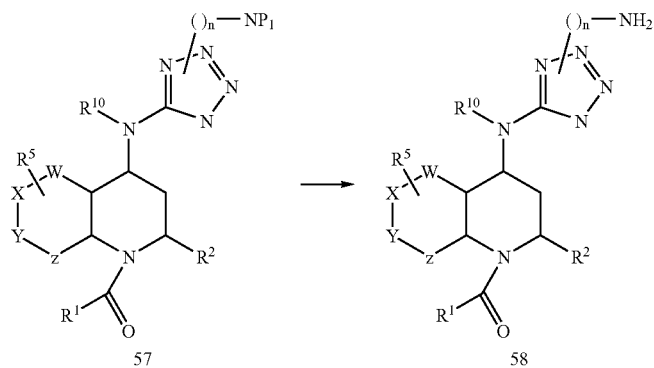

-continued

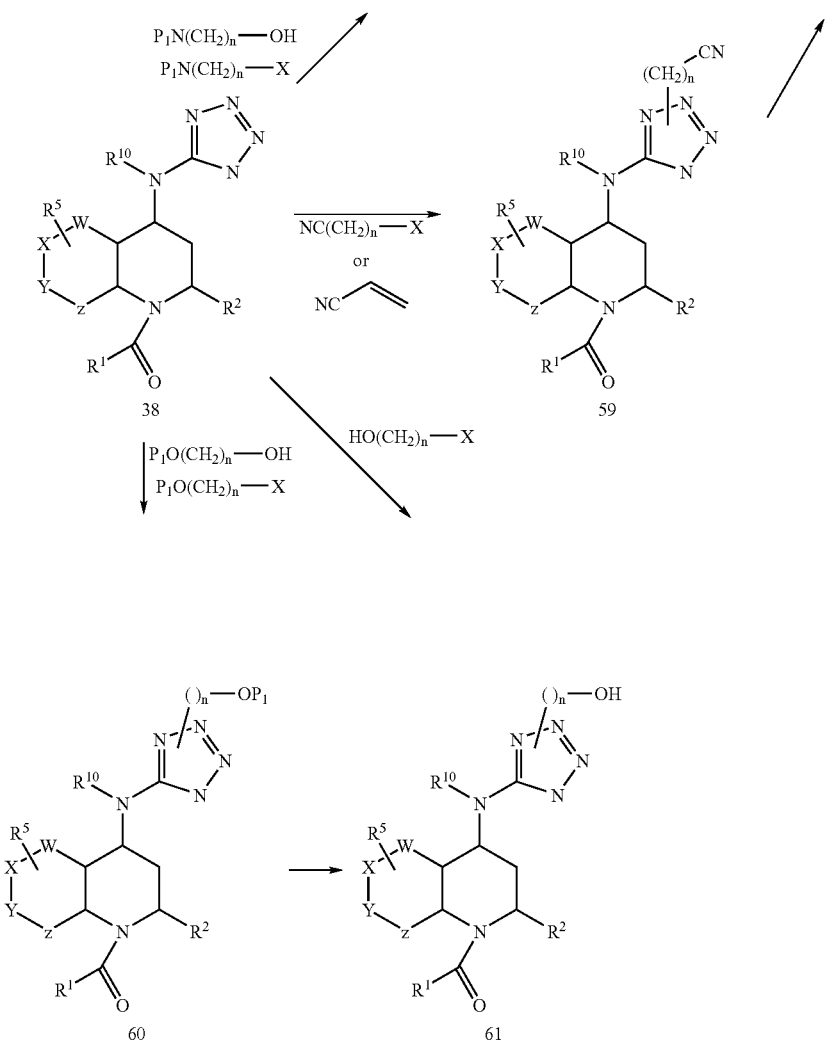

As shown in Scheme 10, tetrazole 38 can be alkylated with the appropriate protected aminoalcohol under Mitsunobu conditions or with the appropriate protected aminoalkylbromide, iodide or mesylate, or the like in the presence of base to provide a protected aminoalkyltetrazole 57. Removal of P1 using methods well known in the art can yield compound 58. Alternatively, tetrazole 38 can be alkylated with the appropriate alkylcyano bromide or with the appropriate acrylonitrile under Michael reaction conditions. Cyano derivative 59 can be then reduced to the corresponding amine 58. Tetrazole 38 can be alkylated using the appropriate alcohol under Mitsunobu conditions, or with the appropriate alkyl halide or the like in the presence of base to provide 60. Removal of P1 (protecting group) using methods well known in the art can yield compound 61. Alternatively hydroxyalkyltetrazole 61 can be obtained by alkylation of 38 with the corresponding halide in the presence of base.

Scheme 11

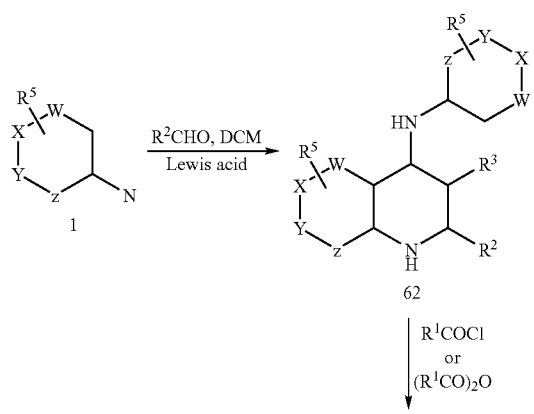

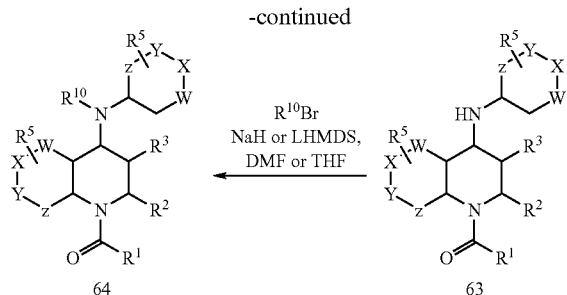

As shown in scheme 11, heteroaryl amine 1 can be converted to 62 by reaction with the appropriate aldehyde in the presence of acid. Compound 62 may be acylated using standard procedures by one skilled in the art to provide 63. Heteroaryl derivative 63 may be alkylated using an appropriate halide or tosylate or the like, in the presence of base to provide 64

Assay

The following assay protocol and result(s) thereof demonstrating the utility and efficacy of the compounds and/or methods of the current invention are given for the purpose of illustration and are not meant to be limiting in any way.

In Vitro Cetp Inhibitor Assay: Spa Assay

An in vitro Scintillation proximity assay (SPA) has been used to test the ability of compounds of this invention to inhibit the transfer of radiolabeled cholesterol esters between HDL and LDL. This assay monitors the inhibition of the transfer of [$^3$H]cholesterol esters from HDL (Amersham) to biotinylated LDL (Amersham) by a CETP source. CETP produced by AV-12 cells that have been created to express human CETP has been used to mediate the transfer. After 30 minutes incubation in which the radiolabeled cholesterol ester is transferred in a HEPES-NaCl based buffer, the reaction is stopped and the biotinylated LDL is bound to streptavidin/scintillant coated SPA beads (Amersham). Then the radioactive signal is measured in a Packard 96-well scintillation TopCounter with window settings fully open. A decrease in radioactive signal represents the ability of compounds of the invention to inhibit the activity of CETP.

Alternatively, additional CETP sources can be used to mediate the transfer of radiolabeled cholesterol ester in this assay. Endogenous CETP from human plasma, CETP from mice made to express human CETP, and endogenous CETP from hamsters can be used as the CETP source in this assay.

Alternatively, other sources may be used as the buffer. In addition to the HEPES-NaCl based buffer that has been used in this assay, human plasma, mouse plasma or a Tris-bufer that is high in albumin may be used as the buffer in which the transfer of radiolabeled cholesterol esters from HDL to LDL may occur.

Alternatively, other sources of radioactivity may be used to track the CETP activity in this assay. In yet another alternative, radiolabeled-LDL may be used in this assay.

Compounds of the present invention tested have shown inhibition of CETP activity below about 100 micromolar when subjected to the SPA assay procedure above.

Assay of Cetp Activity In Vivo

Syrian Golden Hamsters, which express endogenous CETP, are used to assess the activity of the compounds in vivo. Test compounds are administered orally in selected aqueous or oil based vehicles for up to one week. At various times after dosing, ranging from 4 h to 48 h, blood can be obtained. CETP activity is determined by a method similar to that described for the in vitro CETP activity assay, except that plasma from treated animals is used as the CETP source in the assay.

A strain of transgenic mice that express human CETP (Taconic, Germantown, N.Y.) are used to test compounds of this invention. Test compounds are administered orally in selected aqueous or oil based vehicles for up to one week. At various times after dosing, ranging from 4 h to 48 h, blood can be obtained. CETP activity is determined by a method similar to that described for the in vitro CETP activity assay, except that plasma from treated animals is used as the CETP source in the assay.

Alternatively, a strain of transgenic mice that express both human CETP and human apolipoprotein A-1 (Taconic, Germantown, N.Y.) are used to test compounds of this invention. Test compounds are administered orally in selected aqueous or oil based vehicles for up to one week. At various times after dosing, ranging from 4 h to 48 h, blood is obtained. CETP activity is determined by a method similar to that described for the in vitro CETP activity assay, except that plasma from treated animals is used as the CETP source in the assay.

Assay of Plasma Lipids In Vivo

Activity of compounds of this invention in vivo can be determined by comparing the level of elevation of HDL cholesterol relative to control by a given amount of a compound in a CETP-containing animal species. A strain of transgenic mice that express both human CETP and human apolipoprotein A-1 (Taconic, Germantown, N.Y.) is used to test compounds of this invention. Test compounds are administered once orally in selected aqueous or oil based vehicles. At various times after dosing, ranging from 4 h to 24 h, blood is obtained. Blood is allowed to clot and serum is obtained by centrifugation. HDL cholesterol levels in the serum is determined by HDL-C plus reagents (Roche/Hitachi, Indianapolis, Ind.) with a clinical chemistry analyzer (Roche/Hitachi, Indianapolis, Ind.). Additional serum lipids can be analyzed by enzymatic methods. Lipids in the VLDL, LDL and HDL fractions are analyzed by enzymatic methods after precipitation or size exclusion chromatography. An example of the elevation of HDL cholesterol levels at 8 hr are summarized in table 1

TABLE 1

Elevation of HDL cholesterol levels at 8 hr

| Compound of Example No. | Single Oral Dose (mg/kg) | % HDL cholesterol increase |
|---|---|---|
| 8 | 30 | 313 |
| 11 | 30 | 134 |
| 15 | 30 | 91 |
| 18 | 30 | 187 |
| 19 | 30 | 52 |
| 52 | 30 | 66 |

The efficacy of these compounds in vivo can also be determined utilizing Syrian Golden Hampsters. The compounds can be tested in hamsters made hypercholesterolemic by feeding a high fat high cholesterol diet for a minimum of two weeks or in non-hypercholesterolemic hamsters fed normal chow for two weeks. Test compounds can be administered orally in selected aqueous or oil based vehicles for up to 1 week. Serum can be obtained and lipids can be analyzed by enzymatic methods. Lipids in the VLDL, LDL and HDL franctions are analyzed by enzymatic methods after precipitation or size exclusion chromatography.

Alternatively, a strain of transgenic mice that express human CETP (Taconic, Germantown, N.Y.) are used to test the efficacy of the compounds of this invention. The hCETP mice can be made hypercholesterolemic by feeding a high fat chow diet such as TD 88051, as described by Nishina et al. (J Lipid Res., 31, 859-869 (1990)) for at least two weeks before the start of the study. Test compounds can be administered orally in selected aqueous or oil base vehicles for up to 1 week. Serum can be obtained and lipids can be analyzed by enzymatic methods. Lipids in the VLDL, LDL and HDL fractions are analyzed by enzymatic methods after precipitation or size exclusion chromatography.

Method of Treatment

As used herein, the term "effective amount" means an amount of compound of the present invention, i.e., formula I that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.01 mg to about 100 mg/day of a compound of the present invention. Preferred daily doses generally will be from about 1 mg to about 250 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, solvate, prodrug, enantiomer or prodrug thereof, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well-known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, generally, will be administered in a convenient formulation as determined by the attending physician. The following formulation examples are only illustrative and are not intended to limit the scope of the present invention.

Formulations

In the formulations which follow, "Active Ingredient" means a compound of formula I, a salt, solvate, racemate, enantiomer diastereomer or mixture of diastereomers, or prodrug thereof, or a combination of a compound of formula I and other effective agent useful for the prwctice of the invention.

Formulation 1: Gelatin Capsules

Hard gelatin capsules are prepared using the following:

| Ingredient | Quantity (mg/capsule) |
|---|---|
| Active ingredient | 0.1-1000 |
| Starch, NF | 0-650 |
| Starch flowable powder | 0-650 |
| Silicone fluid 350 centistokes | 0-15 |

The formulation above may be changed in compliance with the reasonable variations provided.

A tablet formulation is prepared using the ingredients below:

Formulation 2: Tablets

| Ingredient | Quantity (mg/tablet) |
|---|---|
| Active ingredient | 2.5-1000 |
| Cellulose, microcrystalline | 200-650 |
| Silicon dioxide, fumed | 10-650 |
| Stearate acid | 5-15 |

The components are blended and compressed to form tablets.

Alternatively, tablets each containing 2.5-1000 mg of active ingredient are made up as follows:

Formulation 3: Tablets

| Ingredient | Quantity (mg/tablet) |
|---|---|
| Active ingredient | 25-1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders that are then passed through a No. 14 mesh U.S. sieve. The granules so produced are dried at 50-60° C. and passed through a No. 18 mesh U.S. sieve. The sodium carboxymethyl starch, magnesium stearate, and talc, previously passed through a No. 60 U.S. sieve, are then added to the granules, which after mixing, are compressed on a tablet machine to yield tablets.

Suspensions each containing 0.1-1000 mg of medicament per 5 ml dose are made as follows:

Formulation 4: Suspensions

| Ingredient | Quantity (mg/5 ml) |
|---|---|
| Active ingredient | 0.1-1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to about 30 C and transferred to a filling device. The required amount is then fed to a stainless steel container and diluted with the remaining propellant. The valve units are then fitted to the container.

Formulation 6: Intravenous Solution

| Ingredient | Quantity |
|---|---|
| Active ingredient | 50 mg |
| Isotonic saline | 1,000 mL |

The solution of the above ingredients is intravenously administered to a patient at a rate of about 1 mL per minute.

EXAMPLES

The following examples are illustrative of compounds made or compounds that could be made by one of skill in the art following the teachings disclosed herein and known to one of skill in the art and requiring minimal experimentation. The disclosed examples should in no way limit the scope of the claims.

Example 1

7-[Acetyl-(3,5-bis-trifluoromethyl-benzyl)-amino]-5-ethyl-6,7-dihydro-5H-thieno[3,2-b]pyridine-4-carboxylic acid isopropyl ester

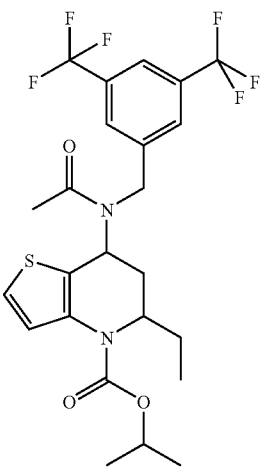

Step 1. Preparation of 3-Amino-thiophene-2-carboxylic acid

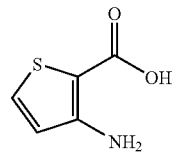

Add 5 N NaOH (50 ml) to a solution of metlhyl 3-aminothiophene-2-carboxylate (7.86, 50.0 mmole) in methanol (250 ml). Heat the reaction mixture at 60° C. overnight. Adjust the pH to about 6 to 7 by adding 1 N HCl. Extract with ethyl acetate (5×200 ml). Combine the organic layers, dry over $Na_2SO_4$. Filter and concentrate to provide 3-amino-thiophene-2-carboxylic acid (5.84 g, 82%) as a white powder, which was used immediately for the next step. MS (ES+): 144 (M+H); (ES−): 142 (M−H).

Step 2. Preparation of 2-(Thiophen-3-ylaminomethylene)-malonic acid diethyl ester

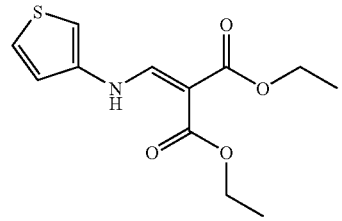

Add diethyl etboxymethylenemalonate (8.99 ml, 44.9 mmol) to a solution of 3-amino-thiophene-2-carboxylic acid (5.84 g, 40.8 mmol) in to]uene (100 ml). Heat the mixture under reflux overnight. Evaporate the solvent in vacuo. Purify using silica gel column chromatography (gradient eluent, 0-20% ethyl acetate in hexane) to provide 2-(thiophen-3-ylaminomethylene)-malonic acid diethyl ester (7.86 g, 86%) as a white crystalline solid. MS (ES+): 270 (M+H).

Step 3. Preparation of 7-Hydroxy-thieno[3,2-b]pyridine-6-carboxylic acid ethyl ester

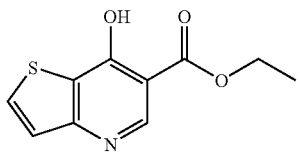

Add 2-(thiophen-3-ylaminomethylene)-malonic acid diethyl ester (7.66 g, 28.4 mmol) to refluxing phenyl ether (100 ml) over a period of 5 min under nitrogen. After the addition is complete, keep the reaction under reflux for 30 min. Cool the reaction mixture to room temperature, and then pour it into ethyl acetate (1000 ml). Collect the brown precipitate by filtration to obtain 7-hydroxy-thieno[3,2-b]pyridine-6-carboxylic acid ethyl ester (4.82 g, 76%). MS (ES+): 224 (M+H); (ES−): 222 (M−H).

Step 4. Preparation of 7-Oxo-7H-thieno[3,2-b]pyridine-4,6-dicarboxylic acid 6-ethyl ester 4-isopropyl ester

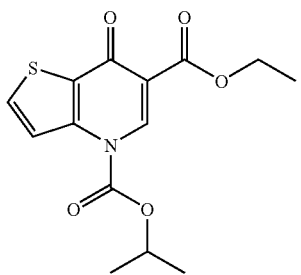

Add pyridine (1.20 ml, 14.8 mmol) to a suspension of 7-hydroxy-thieno[3,2-b]pyridine-6-carboxylic acid ethyl ester (1.10 g, 4.93 mmol) in dichloromethane (50 ml), and then add isopropyl chloroformate (1.0 N in toluene, 14.8 ml). Stir the reaction mixture at room temperature overnight. Wash the mixture with 1 N HCl (50 ml) followed by brine (3×50 ml). Separate the organic layer, dry over sodium sulfate, filter and concentrate. Purify using silica gel column chromatography (gradient eluent, 0-60% ethyl acetate in hexane) to provide 7-oxo-7H-thieno[3,2-b]pyridine-4,6-dicarboxylic acid 6-ethyl ester 4-isopropyl ester (1.37 g, 90%) as a white crystalline solid. MS (ES+): 310 (M+H).

Step 5. Preparation of 5-Ethyl-7-oxo-6,7-dihydro-5H-thieno[3,2-b]pyridine-4,6-dicarboxylic acid 6-ethyl ester 4-isopropyl ester

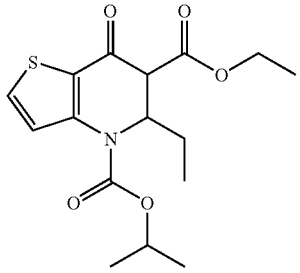

Mix 7-oxo-7H-thieno[3,2-b]pyridine-4,6-dicarboxylic acid 6-ethyl ester 4-isopropyl ester (0.512 g, 1.66 mmol) and copper(I) iodide (0.695 g, 3.65 mmol) in THF (35 ml). Cool the mixture to −78° C. Inject ethyl magnesium bromide (3.0 M in diethyl ether, 1.66 ml) and stir for 1.5 h. Add another portion of ethyl magnesium bromide (3.0 M in diethyl ether, 3.30 ml) and keep the reaction at −78° C. for one more hour. Warm up to −20° C. overnight in a freezer. Pour the reaction mixture into saturated ammonium chloride solution (200 ml). Extract with ethyl acetate (3×200 ml). Combine all the organic layers, dry over Na₂SO₄, filter and concentrate to give 5-ethyl-7-oxo-6,7-dihydro-5H-thieno[3,2-b]pyridine-4,6-dicarboxylic acid 6-ethyl ester 4-isopropyl ester (0.520 g, 93%) as a crude oil. MS (ES+): 340 (M+H).

Step 6. Preparation of 5-Ethyl-7-oxo-6,7-dihydro-5H-thieno[3,2-b]pyridine-4-carboxylic acid isopropyl ester

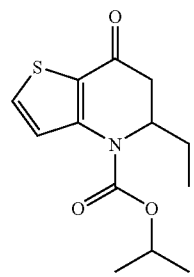

Add lithium chloride (0.162 g, 3.83 mmol) in one portion to a mixture of 5-ethyl-7-oxo-6,7-dihydro-5H-thieno[3,2-b]pyridine-4,6-dicarboxylic acid 6-ethyl ester 4-isopropyl ester (0.520 g, 1.53 mmol) in dimethylsulfoxide (15 ml) and water (2 drops). Heat the mixture at 160° C. for 4 h. Cool the reaction to room temperature and partition between ethyl acetate (50 ml) and brine (50 ml). Separate the organic layer and wash with brine (3×50 ml). Dry the organic portion over sodium sulfate, filter and concentrate. Purify using silica gel column chromatography (gradient eluent, 0-15% ethyl acetate in hexane) to give 5-ethyl-7-oxo-6,7-dihydro-5H-thieno[3,2-b]pyridine-4-carboxylic acid isopropyl ester (0.236 g, 58% for two steps) as an oil. MS (ES+): 268 (M+H).

Step 7. Preparation of 7-(3,5-Bis-trifluoromethyl-benzylamino)-5-ethyl-6,7-dihydro-5H-thieno[3,2-b]pyridine-4-carboxylic acid isopropyl ester

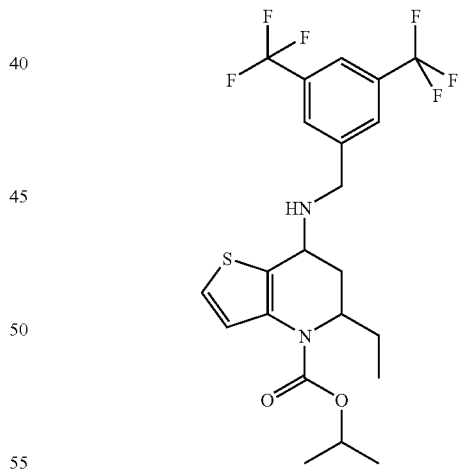

Inject titanium(IV)isopropoxide (0.372 ml, 1.26 mmol) to a mixture of 5-ethyl-7-oxo-6,7-dihydro-5H-thieno[3,2-b]pyridine-4-carboxylic acid isopropyl ester (0.225 g, 0.842 mmol), 3,5-bis(trifluoromethyl)benzylamine (0.211 g, 0.842 mmol), and then stir at room temperature for 4 h. Inject a solution of sodium cyanoborohydride (0.212 g, 3.37 mmol) in methanol (8 ml) to the reaction mixture and continue to stir at room temperature overnight. Add another portion of solution of sodium cyanoborohydride (0.212 g, 3.37 mmol) in methanol (8 ml) and continue to stir for 4 h. Add sodium borohydride (0.159 g, 4.21 mmol) and heat the reaction at 60° C. overnight. Treat the mixture with 0.1 N sodium hydroxide (25 ml) for 10 minutes, and then filter through a Celite® pad. Wash the filtered residue thoroughly with ethyl acetate. Separate the organic layer, wash with brine (3×50 ml), dry over Na$_2$SO$_4$, filter and concentrate to provide crude 7-(3,5-bis-trifluoromethyl-benzylamino)-5-ethyl-6,7-dihydro-5H-thieno [3,2-b]pyridine-4-carboxylic acid isopropyl ester (0.315 g) which was elaborated without further purification. MS (ES+): 495 (M+H).

Step 8. Preparation of 7-[Acetyl-(3,5-bis-trifluoromethyl-benzyl)-amino]-5-ethyl-6,7-dihydro-5H-thieno [3,2-b]pyridine-4-carboxylic acid isopropyl ester

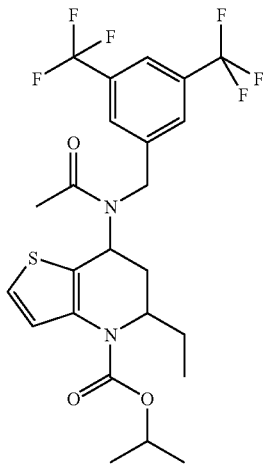

Inject acetic anhydride (0.250 ml, 2.65 mmol) dropwise to a solution of crude 7-(3,5-bis-trifluoromethyl-benzylamino)-5-ethyl-6,7-dihydro-5H-thieno[3,2-b]pyridine-4-carboxylic acid isopropyl ester (0.120 g, 0.243 mmol) and pyridine (0.250 ml, 3.10 mmol) in dichloromethane (1 ml) at room temperature. Stir the mixture at room temperature for 16 h. Evaporate the solvents and purify the resulting reside using silica gel column chromatography (gradient eluent, 0-35% ethyl acetate in hexane) to provide the title compound (0.0290 g, 22%). MS (ES+): 559 (M+Na); (ES−): 535 (M−H). cl Example 2

4-[Acetyl-(3,5-bis-trifluoromethyl-benzyl)-amino]-2-ethyl-7-methyl-3,4-dihydro-2H-[1,8]naphthyridine-1-carboxylic acid isopropyl ester

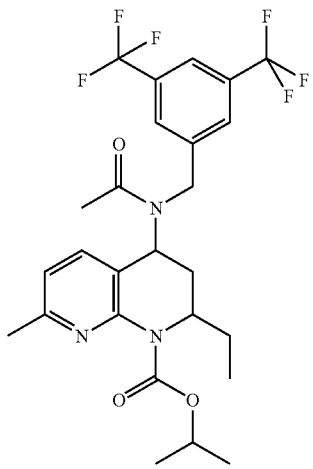

Step 1. Preparation of 2-[(6-Methyl-pyridin-2-ylamino)-methylene]-malonic acid diethyl ester

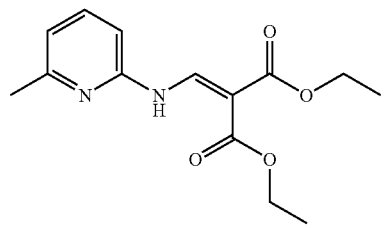

Add diethyl ethoxymethylenemalonate (10.0 ml, 55.0 mmol) to a solution of 6-methyl-pyridin-2-ylamine (5.41 g, 50.0 mmol) in toluene (100 ml). Heat the mixture under reflux overnight. Evaporate the solvent in vacuo to provide 2-[(6-methyl-pyridin-2-ylamino)-methylene]-malonic acid diethyl ester (14.8 g) as a white solid. MS (ES+): 279 (M+H).

Step 2. Preparation of 7-Methyl-4-oxo-1,4-dihydro-[1,8]naphthyridine-3-carboxylic acid ethyl ester

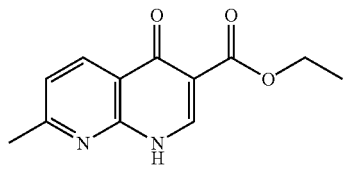

Add 2-[(6-methyl-pyridin-2-ylamino)-methylene]-malonic acid diethyl ester (14.8 g) to the refluxing phenyl ether (100 ml) over a period of 5 min under nitrogen. After the addition is complete, keep the reaction under reflux for 3 h. Cool it to room temperature, and then pour the reaction mixture into 1:1 hexane/ethyl acetate (2000 ml). Collect the brown precipitate by filtration to obtain 7-methyl-4-oxo-1,4-dihydro-[1,8]naphthyridine-3-carboxylic acid ethyl ester (8.35 g, 72% for two steps). MS (ES+): 233 (M+H); (ES−): 231 (M−H).

Step 3. Preparation of 7-Methyl-4-oxo-4H-[1,8]naphthyridine-1,3-dicarboxylic acid 3-ethyl ester 1-isopropyl ester

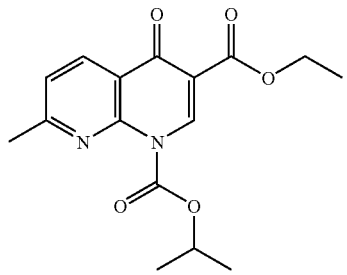

Add pyridine (2.43 ml, 30.0 mmol) to a suspension of 7-methyl-4-oxo-1,4-dihydro-[1,8]naphthyridine-3-carboxylic acid ethyl ester (2.32 g, 10.0 mmol) in dichloromethane (100 ml), and then add isopropyl chloroformate (1.0 N in toluene, 30.0 ml). Stir the reaction mixture at room temperature overnight. Wash with brine (3×100 ml). Separate the organic layer, dry over Na$_2$SO$_4$, filter, and concentrate. Purify using silica gel column chromatography (gradient eluent, 0-60% ethyl acetate in hexane) to provide 7-methyl-4-oxo- 4H-[1,8]naphthyridine-1,3-dicarboxylic acid 3-ethyl ester 1-isopropyl ester (1.31 g, 41%). MS (ES+): 319 (M+H).

Step 4. Preparation of 2-Ethyl-7-methyl-4-oxo-3,4-dihydro-2H-[1,8]naphthyridine-1,3-dicarboxylic acid 3-ethyl ester 1-isopropyl ester

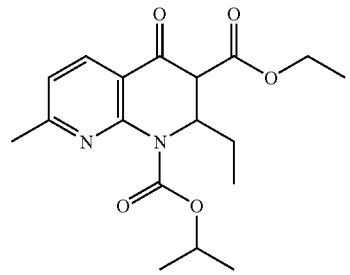

Mix 7-methyl-4-oxo-4H-[1,8]naphthyridine-1,3-dicarboxylic acid 3-ethyl ester 1-isopropyl ester (1.21 g, 3.80 mmol) and copper(I) iodide (1.59 g, 8.36 mmol) in THF (75 ml). Cool the mixture to −78° C. Inject ethyl magnesium bromide (3.0 M in diethyl ether, 7.60 ml) and stir for 2 h. Warm up to −20° C. and keep the reaction at that temperature for 3 h. Pour the reaction mixture into saturated ammonium chloride solution (100 ml). Extract with ethyl acetate (3×100 ml). Combine the organic layers, dry over sodium sulfate, filter and concentrate. Purify using silica gel column chromatography (gradient eluent, 0-60% ethyl acetate in hexane) to provide 2-ethyl-7-methyl-4-oxo-3,4-dihydro-2H-[1,8]naphthyridine-1,3-dicarboxylic acid 3-ethyl ester 1-isopropyl ester (0.715 g, 54%). MS (ES+): 349 (M+H).

Step 5. Preparation of 2-Ethyl-7-methyl-4-oxo-3,4-dihydro-2H-[1,8]naphthyridine-1-carboxylic acid isopropyl ester

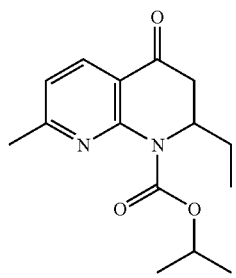

Add lithium chloride (0.216 g, 5.10 mmol) in one portion to a mixture of 2-ethyl-7-methyl-4-oxo-3,4-dihydro-2H-[1,8]naphthyridine-1,3-dicarboxylic acid 3-ethyl ester 1-isopropyl ester (0.710 g, 2.04 mmol) in dimethylsulfoxide (20 ml) and water (4 drops). Heat the mixture at 160° C. for 3 h. Cool down to room temperature, partition between ethyl acetate (100 ml) and brine (100 ml). Separate the organic layer, wash with brine (3×100 ml). Dry over sodium sulfate, filter and concentrate. Purify using silica gel column (gradient eluent, 0-20% ethyl acetate in hexane) to provide 2-ethyl-7-mnethyl-4-oxo-3,4-dihydro-2H-[1,8]naphthyridine-1-carboxylic acid isopropyl ester (0.457 g, 81) as a pale yellow solid. MS (ES+): 277 (M+H).

Step 6. Preparation of 4-(3,5-Bis-trifluoromethyl-benzylamino)-2-ethyl-7-methyl-3,4-dihydro-2H-[1,8]naphthyridine-1-carboxylic acid isopropyl ester

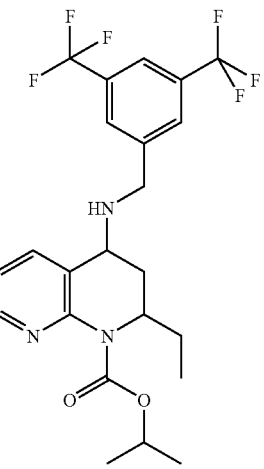

Inject titanium(IV)isopropoxide (0.0870 ml, 0.299 mmol) to a mixture of 2-ethyl-7-methyl-4-oxo-3,4-dihydro-2H-[1,8]naphthyridine-1-carboxylic acid isopropyl ester (0.055 g, 0.199 mmol), and 3,5-bis(trifluoromethyl)benzylamine (0.0500 g, 0.199 mmol), and then stir at room temperature for 6 h. Add methanol (2 ml) followed by NaBH$_4$ (0.0380 g, 0.995 mmol) and stir at room temperature overnight. Treat the mixture with 1 N sodium hydroxide (2 ml) and ethyl acetate (5 ml), and then filter through a Celite® pad. Wash the filtered residue thoroughly with ethyl acetate (30 ml). Separate the organic layer, wash with brine (3×50 ml), dry over sodium sulfate, filter, and concentrate to provide crude 4-(3,5-bis-trifluoromethyl-benzylamino)-2-ethyl-7-methyl-3,4-dihydro-2H-[1,8]naphthyridine-1-carboxylic acid isopropyl ester (0.0900 g) which was elaborated without further purification. MS (ES+): 504 (M+H).

Step 7. Preparation of 4-[Acetyl-(3,5-bis-trifluoromethyl-benzyl)-amino]-2-ethyl-7-methyl-3,4-dihydro-2H-[1,8]naphthyridine-1-carboxylic acid isopropyl ester

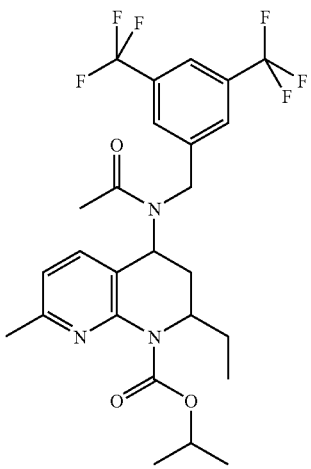

Inject acetic anhydride (0.250 ml, 2.65 mmol) dropwise to a solution of crude 4-(3,5-trifluoromethyl-benzylamino)-2-ethyl-7-methyl-3,4-dihydro-2H-[1,8]naphthyridine-1-carboxylic acid isopropyl ester (0.090 g, 0.199 mmol) and pyridine (0.250 ml, 3.10 mmol) in dichloromethane (1 ml) at room temperature. Stir the mixture at room temperature for 16 h. Evaporate the solvents and purify using silica gel column chromatography (gradient eluent, 0-40% ethyl acetate in hexane) to provide the title compound (0.0650 g, 66%). MS (ES+): 546 (M+H).

Example 3

(+/−)-cis-4-[Acetyl-(3,5-bis-trifluoromethyl-benzyl)-amino]-2-ethyl-6-methoxy-3,4-dihydro-2H-[1,5]naphthyridine-1-carboxylic acid isopropyl ester

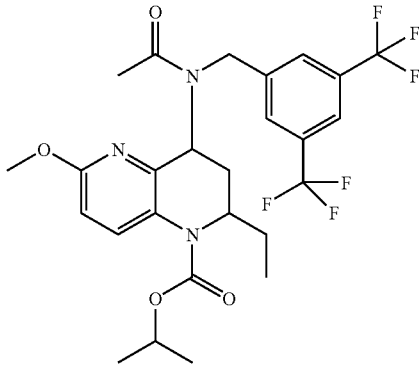

Step 1. Preparation of (+/−)-cis-(2-Ethyl-6-methoxy-1,2,3,4-tetrahydro-[1,5]naphthyridin-4-yl)acetamide

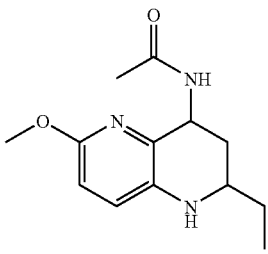

Dissolve 6-methoxy-pyridin-3-ylamine (1.05 g, 8.05 mmol) in anhydrous dichloromethane (35 mL), add sodium sulfate (1.14 g) and cool the reaction mixture to −20° C. Add propionaldehyde (0.659 mL, 8.85 mmpl) and stir the mixture from −20 to 0° C. for 1.5 h. Filter the sodium sulfate and add N-vinyl acetamide (0.706 g, 8.85 mmol) to the filtrate at −20° C. followed by boron trifluoride diethyl etherate (0.088 mL, 0.805 mmol). Stir the reaction mixture from −20 to −10° C. for 2 h. Remove the solvent in vacuo and chromatograph the residue over a silica cartridge, eluting with hexanes/ethyl acetate to afford the title compound (1.25 g, 63%). MS (ES+): 250 (M+H).

Step 2. Preparation of (+/−)-cis-4-Acetylamino-2-ethyl-6-methoxy-3,4-dihydro-2H-[1,5]naphthyridine-1-carboxylic acid isopropyl ester

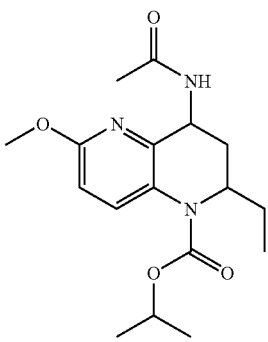

Add isopropyl chloroformate (3.10 mL, 2.82 mmol, 1.0 M in toluene) dropwise to a solution of (+/−)-cis-N-(2-ethyl-6-methoxy-1,2,3,4-tetrahydro-[1,5]naphthyridin-4-yl)acetamide (702 mg, 3.102 mmol) and pyridine (0.677 mL, 8.46 mmol) in dichloromethane (15 mL) at 0° C. under an atmosphere of nitrogen and stir at room temperature for 10 min. Add 1 M HCl and separate the layers. Extract the aqueous layer with dichloromethane. Dry the organic layers over anhydrous sodium sulfate, filter, and remove the solvent under reduced pressure, to afford the title compound (895 mg, 95%). MS (ES+): 336 (M+H).

Step 3. Preparation of (+/−)-cis-4-Amino-2-ethyl-6-methoxy-3,4-dihydro-2H-[1,5]naphthyridine-1-carboxylic acid isopropyl ester

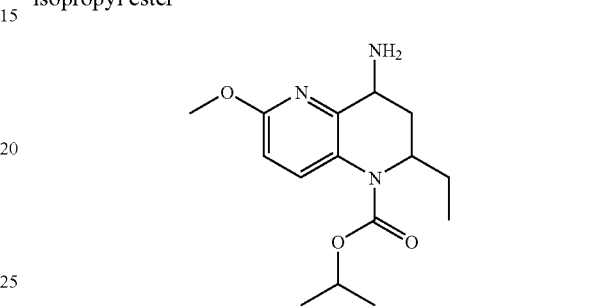

Heat at 80° C. a solution of (+/−)-cis-4-acetylamino-2-ethyl-6-methoxy-3,4-dihydro-2H-[1,5]naphthyridine-1-carboxylic acid isopropyl ester (100 mg, 0.298 mmol) in 5 N HCl (1 mL) for 4 h. Cool the reaction mixture to room temperature, pour the crude onto a saturated solution of sodium carbonate and extract with dichloromethane. Dry the organic layer over anhydrous sodium sulfate, filter, and remove the solvent under reduced pressure, to afford the title compound (85 mg, 98%). MS (ES+): 277 (M−NH$_2$).

Step 4. Preparation of (+/−)-cis-4-(3,5-Bis-trifluoromethyl-benzylamino)-2-ethyl-6-methoxy-3,4-dihydro-2H-[1,5]naphthyridine-1-carboxylic acid isopropyl ester

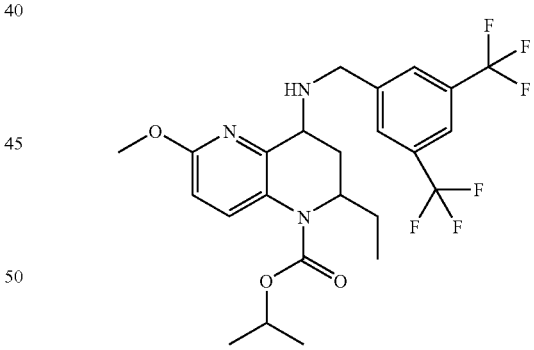

Add sodium triacetoxyborohydride (0.091 mg, 0.409 mmol) to a mixture of 3,5-bis(trifluoromethyl)benzaldehyde (0.045 mL, 0.273 mmol), acetic acid (0.018 mL, 0.303 mmol) and (+/−)-cis-4-amino-2-ethyl-6-methoxy-3,4-dihydro-2H-[1,5]naphthyridine-1-carboxylic acid isopropyl ester (0.08 mg, 0.273 mmol) in dichloroethane (3 mL). Stir the mixture at room temperature under an atmosphere of nitrogen for 14 h. Add a saturated solution of ammonium chloride, separate the layers, and extract the aqueous layer with dichloromethane. Dry the combined organic layers over anhydrous sodium sulfate, filter and remove the solvent under reduced pressure. Purify the residue by flash chromatography, eluting with hexanes/ethyl acetate, to afford the title compound (125 mg, 88%). MS (ES+): 520 (M+H).

Step 5. Preparation of (+/−)-cis-4-[Acetyl-(3,5-trifluoromethyl-benzyl)-amino]-2-ethyl-6-methoxy-3,4-dihydro-2H-[1,5]naphthyridine-1-carboxylic acid isopropyl ester

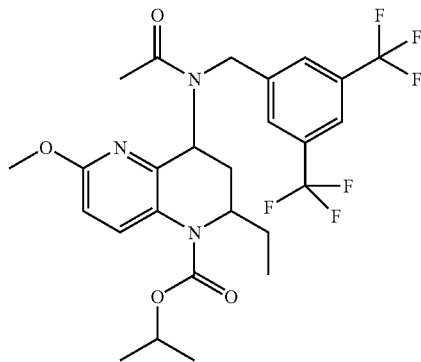

Add acetic anhydride (0.023 mL, 1.205 mmol) to a solution of (+/−)-cis-4-(3,5-bis-trifluoromethyl-benzylamino)-2-ethyl-6-methoxy-3,4-dihydro-2H-[1,5]naphthyridine-1-carboxylic acid isopropyl ester (125 mg, 0.241 mmol) and pyridine (0.097 mL, 1.205 mmol) in dichloromethane (2 mL), and stir at room temperature for 14 h. Remove the solvent under reduced pressure and purify the residue by flash chromatography, eluting with hexanes/ethyl acetate, to afford the title compound (105 mg, 78%). $^1$H NMR (CDCl$_3$, 300 MHz): δ 0.66-0.72 (m, 3H), 1.20-1.29 (m, 7H), 1.33-1.69 (m, 3H), 2.01-2.21 (m, 3H), 2.26-2.33 (m, 1H), 3.82, 3.86 (s, 3H), 4.22-4.28 (m, 1H), 4.81-5.01 (m, 2H), 6.59, 6.65 (d, J=8.7 Hz, 1H), 7.61-7.73 (m, 4H). MS (ES+): 562 (M+H).

Example 4

(+/−)-cis-4-[Acetyl-(3,5-bis-trifluoromethyl-benzyl)-amino]-2-ethyl-6-trifluoromethyl-3,4-dihydro-2H-[1,5]naphthyridine-1-carboxylic acid isopropyl ester

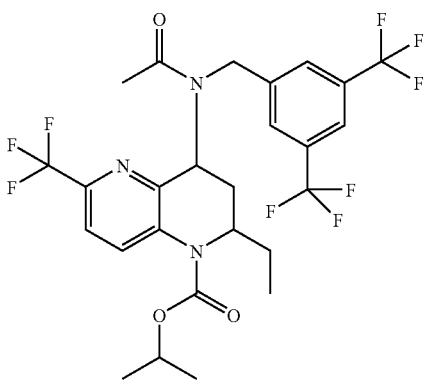

Prepare the title compound by essentially following the procedures described in Example 3, Steps 1-5, by replacing 6-methoxy-pyridin-3-ylamine with 6-trifluoromethyl-pyridin-3-yl-amine in Example 3, Step 1. MS (ES+): 600 (M+H).

Example 5

(+/−)-cis-4-[Acetyl-(3,5-bis-trifluoromethyl-benzyl)-amino]-2-ethyl-6-bromo-3,4-dihydro-2H-[1,5]naphthyridine-1-carboxylic acid isopropyl ester

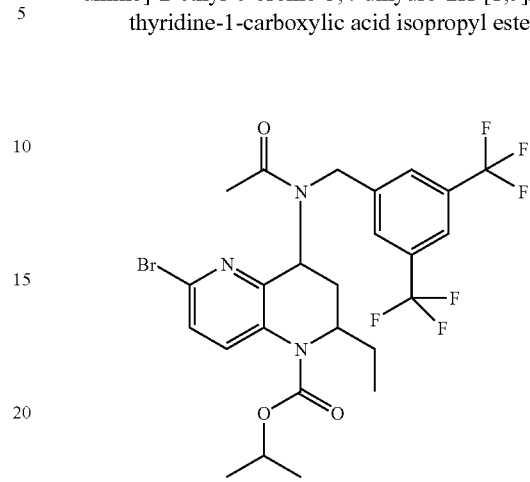

Prepare the title compound by essentially following the procedures described in Example 3, Steps 1-5, by replacing 6-methoxy-pyridin-3-ylamine with 6-bromo-pyridin-3-ylamine in Example 3, Step 1. MS (ES+): 610, 612 (M+H).

Example 6

(+/−)-cis-4-[Acetyl-(3,5-bis-trifluoromethyl-benzyl)-amino]-2-ethyl-6-dimethylamino-3,4-dihydro-2H-[1,5]naphthyridine-1-carboxylic acid isopropyl ester

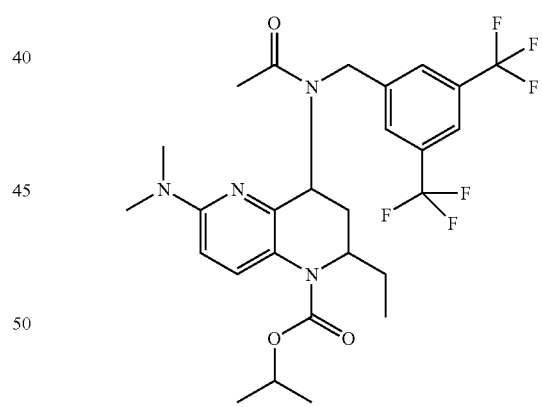

Add N,N-dimethylamine 40% in water (0.5 mL) to a solution of (+/-)-cis-4-[acetyl-(3,5-trifluoromethyl-benzyl)-amino]-2-ethyl-6-bromo-3,4-dihydro-2H-[1,5]naphthyridine-1-carboxylic acid isopropyl ester (60 mg, 0.098 mmol) in dimethylsulfoxide (0.2 mL) and heat the mixture at 100° C. in a sealed tube for 15 h. Cool the reaction mixture to room temperature, add water and extract with ethyl acetate. Dry the organic layer over anhydrous sodium sulfate, filter, and remove the solvent under reduced pressure. Chromatograph the residue over a silica gel cartridge, eluting with hexanes/ethyl acetate to provide the title compound (32 mg, 57%). MS (ES+): 575 (M+H).

Example 7

(+/−)-cis-4-[Acetyl-(3,5-bis-trifluoromethyl-benzyl)-amino]-2-ethyl-6-methyl-3,4-dihydro-2H-[1,5]naphthyridine-1-carboxylic acid isopropyl ester

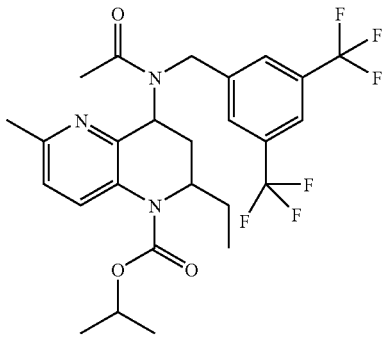

Add 1,1′-bis(diphenylphosphino)(II) chloride, complex with dichloromethane (9 mg, 0.012 mmol) to a suspension of (+/−)-cis-4-[acetyl-(3,5-bis-trifluoromethyl-benzyl)-amino]-2-ethyl-6-bromo-3,4-dihydro-2H-[1,5]naphthyridine-1-carboxylic acid isopropyl ester (50 mg, 0.08 mmol), methyl boronic acid (15 mg, 0.24 mmol) and cesium fluoride (40 mg, 0.28 mmol) in dry dioxane (1.5 mL) and heat the mixture at 80° C. in a sealed tube for 15 h. Cool the reaction mixture to room temperature, add water and extract with dichloromethane. Dry the organic layer over anhydrous sodium sulfate, filter and remove the solvent under reduced pressure. Chromatograph the residue over a silica gel cartridge, eluting with hexanes/ethyl acetate to provide the title compound (37 mg, 84%). MS (ES+): 546 (M+H).

Example 8

(+/−)-cis-4-[(3,5-Bis-trifluoromethyl-benzyl)-2-methyl-2H-tetrazol-5-yl)-amino]-2-ethyl-6-methoxy-3,4-dihydro-2H-[1,5]naphthyridine-1-carboxylic acid isopropyl ester

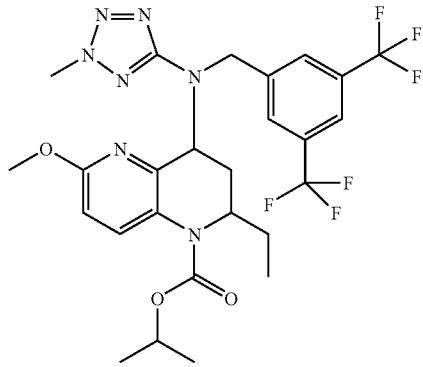

Step 1. Preparation of (+/−)-cis-4-[(3,5-Bis-trifluoromethyl-benzyl)-cyano-amino]-2-ethyl-6-methoxy-3,4-dihydro-2H-[1,5]naphthyridine-1-carboxylic acid isopropyl ester

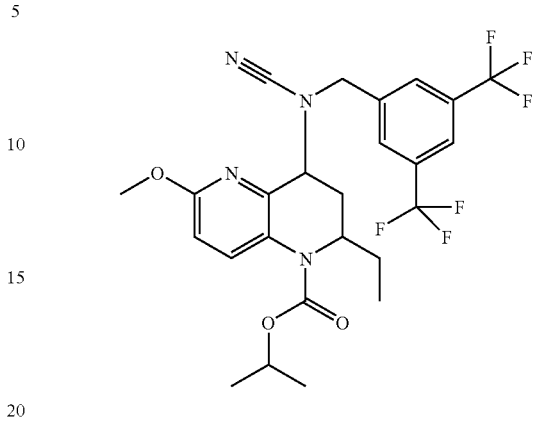

Add diisopropylethylamine (0.146 mL, 0.962 mmol) followed by cyanogen bromide (63 mg, 0.577 mmol) to a solution of (+/−)-cis-4-(3,5-bis-trifluoromethyl-benzylamino)-2-ethyl-6-methoxy-3,4-dihydro-2H-[1,5]naphthyridine-1-carboxylic acid isopropyl ester (200 mg, 0.385 mmol) in dry tetrahydrofuran (5 mL) and stir the mixture at room temperature for 15 h. Add water, separate the layers, and extract the aqueous layer with ethyl acetate. Dry the combined organic layers over anhydrous sodium sulfate, filter and remove the solvent under reduced pressure. Purify the residue by flash chromatography, eluting with hexanes/ethyl acetate, to afford the title compound (104 mg, 50%). MS (ES+): 545 (M+H).

Step 2. Preparation of (+/−)-cis-4-[(3,5-Bis-trifluoromethyl-benzyl)-(2H-tetrazol-5-yl)-amino]-2-ethyl-6-methoxy-3,4-dihydro-2H-[1,5]naphthyridine-1-carboxylic acid isopropyl ester

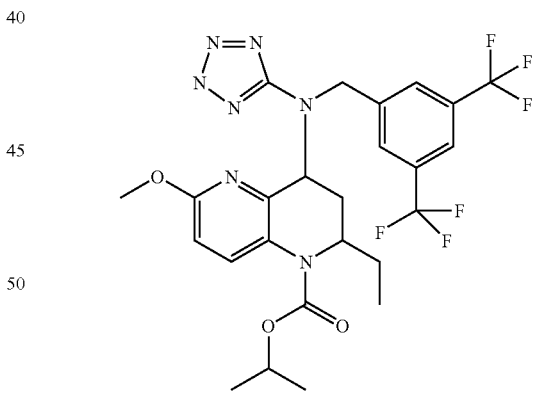

Heat at 120° C. a mixture of (+/−)-cis-4-[(3,5-bis-trifluoromethyl-benzyl)-cyano-amino]-2-ethyl-6-methoxy-3,4-dihydro-2H-[1,5]naphthyridine-1-carboxylic acid isopropyl ester (100 mg, 0.184 mmol), sodium azide (17 mg, 0.258 mmol) and triethyl amine hydrochloride (35 mg, 0.258 mmol) in dry toluene under an atmosphere of nitrogen for 8 h. Then add more sodium azide (6 mg) and triethyl amine hydrochloride (13 mg) and heat the mixture for 4 h. Cool to room temperature, dilute with ethyl acetate, and wash with 1 N HCl. Dry the organic layer over anhydrous sodium sulfate, filter, and remove the solvent under reduced pressure. Purify the residue by flash chromatography, eluting with hexanes/ethyl acetate, to afford the title compound (61 mg, 50%). MS (ES+): 588 (M+H).

Step 3. Preparation of (+/−)-cis-4-[(3,5-Bis-trifluoromethyl-benzyl)-(2-methyl-2H-tetrazol-5-yl)-amino]-2-ethyl-6-methoxy-3,4-dihydro-2H-[1,5]naphthyridine-1-carboxylic acid isopropyl ester

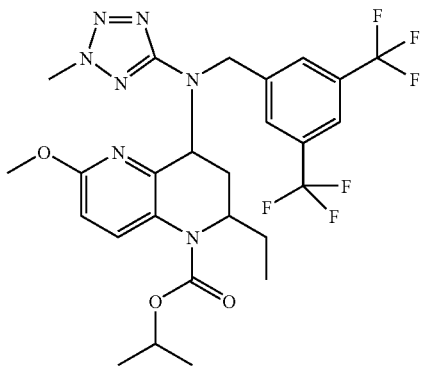

Add triphenylphosphine (27 mg, 0.104 mmol), methanol (17 mg, 0.52 mmol), and diisopropylazodicarboxylate (0.018 mL, 0.104 mmol) to a solution of (+/−)-cis-4-[(3,5-bis-trifluoromethyl-benzyl)-(2H-tetrazol-5-yl)-amino]-2-ethyl-6-methoxy-3,4-dihydro-2H-[1,5]naphthyridine-1-carboxylic acid isopropyl ester in dry dichloromethane (1 mL) and stir the mixture for 15 h at room temperature. Remove the solvent in vacuo and purify the residue by silica gel chromatography, eluting with ethyl acetate/hexanes to afford the title compound (41 mg, 66%). MS (ES+): 602 (M+H).

Example 9

(+/−)-cis-4-[(3,5-Bis-trifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester

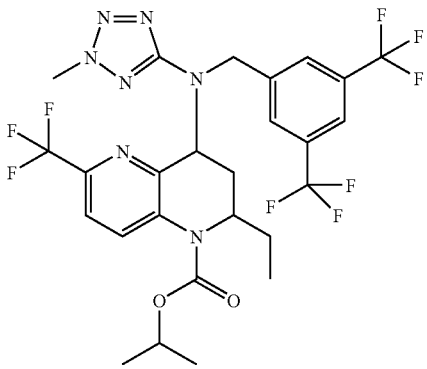

Prepare the title compound by essentially following the procedures described in Example 8 (Steps 1-3), by replacing (+/−)-cis-4-(3,5-bis-trifluoromethyl-benzylamino)-2-ethyl-6-methoxy-3,4-dihydro-2H-[1,5]naphthyridine-1-carboxylic acid isopropyl ester with (+/−)-cis-4-(3,5-bis-trifluoromethyl-benzylamino)-2-ethyl-6-trifluoromethyl-3,4-dihydro-2H-[1,5]naphthyridine-1-carboxylic acid isopropyl ester (from Example 4) in Example 8, Step 1. MS (ES+): 640 (M+H).

Example 10

(2S,4R)-4-[(3,5-Bis-trifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester

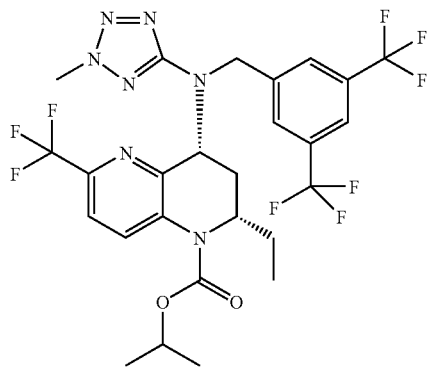

Obtain the title compound by chiral resolution of (+/−)-cis-4-[(3,5-bis-trifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester (Example 9) on a Chiralpak AD (4.6×150 mm), flow rate 0.6 mL/min, solvents: 10% propan-2-ol in heptane with N,N-dimethylethylamine, $R_f$=5.2 min, wavelength: 270 nm. EE=100%. MS (ES+): 640 (M+H).

Example 11

(2R,4S)-4-[(3,5-Bis-trifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester

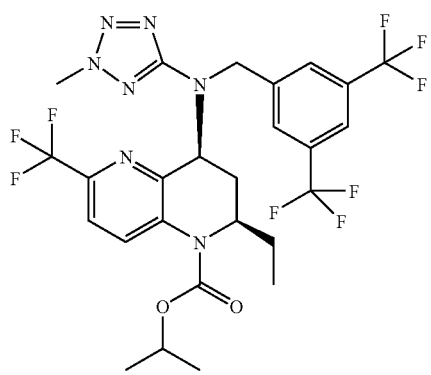

Obtain the title compound by chiral resolution of (+/−)-cis-4-[(3,5-bis-trifluoromethyl-benzyl)-2-methyl-2H-tetrazol-5-yl)-amino]-2-ethyl-6-trifluoromethyl-3,4-dihydro-2H-[1,5]naphthyridine-1-carboxylic acid isopropyl ester (Example 9) on a Chiralpak AD (4.6×150 mm), flow rate 0.6 mL/min, solvents: 10% propan-2-ol in heptane with N,N-dimethylethylamine, $R_f$=6.1 min, wavelength: 270 nm. EE=100%. MS (ES+): 640 (M+H).

Example 12

(+/−)-cis-4-[(3,5-Bis-trifluoromethyl-benzyl)-[2-(2-tert-butoxycarbonylamino-ethyl)-2H-tetrazol-5-yl)-amino]-2-ethyl-6-trifluoromethyl-3,4-dihydro-2H-[1,5]naphthyridine-1-carboxylic acid isopropyl ester

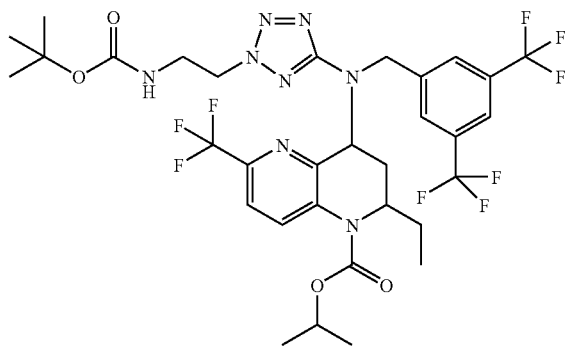

Prepare the title compound by essentially following the procedures described in Example 8, Step 3, by replacing methanol with (2-amino-ethyl) carbamic acid tert-butyl ester and (+/−)-cis-4-[(3,5-bis-trifluoromethyl-benzyl)-(2H-tetrazol-5-yl)-amino]-2-ethyl-6-methoxy-3,4-dihydro-2H-[1,5]naphthyridine-1-carboxylic acid isopropyl ester with (+/−)-cis-4-(3,5-bis-trifluoromethyl-benzylamino)-2-ethyl-6-trifluoromethyl-3,4-dihydro-2H-[1,5]naphthyridine-1-carboxylic acid isopropyl ester. MS (ES+): 767 (M−H).

Example 13

(+/−)-cis-4-[[2-(2-Amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester

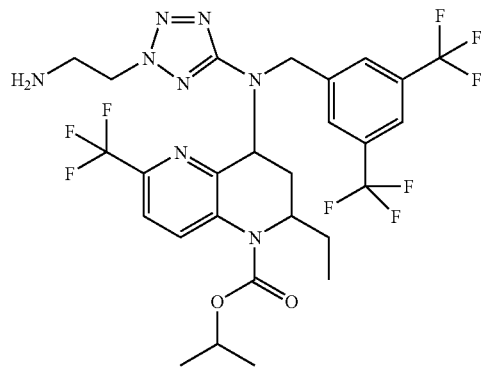

Add trifluoroacetic acid (1 mL) to a solution of (+/−)-cis-4-[(3,5-bis-trifluoromethyl-benzyl)-[2-(2-tert-butoxycarbonylamino-ethyl)-2H-tetrazol-5-yl)-amino]-2-ethyl-6-trifluoromethyl-3,4-dihydro-2H-[1,5]naphthyridine-1-carboxylic acid isopropyl ester (61 mg, 0.079 mmol) in dichloromethane (3 mL) and stir the mixture at room temperature for 3 h. Pour the reaction mixture onto a saturated solution of sodium bicarbonate and extract with dichloromethane. Dry the organic layer over anhydrous sodium sulfate, filter, and remove the solvent under reduced pressure. Purify the residue by silica gel chromatography, eluting with ethyl acetate, to afford the title compound (24 mg, 45%). MS (ES+): 669 (M+H).

Example 14

(2S,4R)-cis-4-[[2-(2-Amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester

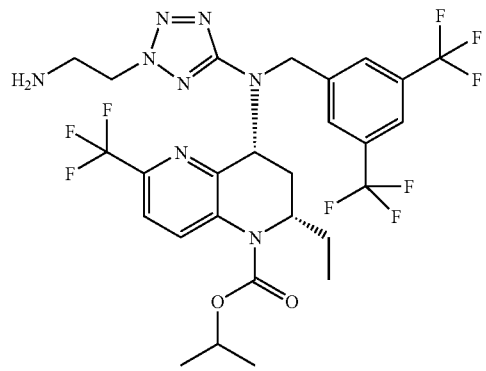

Obtain the title compound by chiral resolution of (+/−)-cis-4-[[2-(2-amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester (Example 13) on a Chiralpak AD (4.6×150 mm), flow rate 0.6 mL/min, solvents: 10% absolute ethanol in heptane with dimethylethylamine, $R_f$=5.2 min, wavelength: 270 nm. EE>97%. MS (ES+): 669 (M+H).

Example 15

(2R,4S)-cis-4-[[2-(2-Amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester

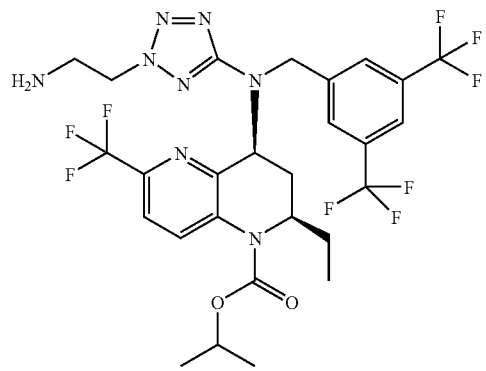

Obtain the title compound by chiral resolution of (+/−)-cis-4-[[2-(2-amino-ethyl)-2H-tetrazol-5-yl]-(3,5-bis-trifluoromethyl-benzyl)-amino]-2-ethyl-6-trifluoromethyl-3,4-dihydro-2H-[1,5]naphthyridine-1-carboxylic acid isopropyl ester (Example 13) on a Chiralpak AD (4.6×150 mm), flow rate 0.6 mL/min, solvents: 10% absolute ethanol in heptane with dimethylethylamine, $R_t$=6.1 min, wavelength: 270 nm. EE>97%. MS (ES+): 669 (M+H).

Example 16

(+/−)-cis and trans-4-[(3,5-Bis-trifluoromethyl-benzyl)-[[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester

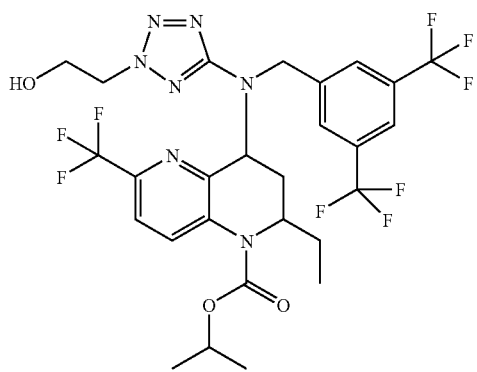

Add 2-bromoethanol (0.093 mL, 1.25 mmol) to a solution of (+/−)-cis-4-(3,5-bis-trifluoromethyl-benzyl-(2H-tetrazol-5-yl)amino)-2-ethyl-6-trifluoromethyl-3,4-dihydro-2H-[1,5]naphthyridine-1-carboxylic acid isopropyl ester (653 mg, 1.045 mmol) and cesium carbonate (749 mg, 2.30 mmol) in dry dimethylformamide under an atmosphere of nitrogen and stir the mixture at 50° C. for 24 h. Cool to room temperature, add water, and extract with ethyl acetate. Dry the organic solvent over sodium sulfate, filter, and remove the solvent under reduced pressure. Purify the residue by silica gel chromatography, eluting with ethyl acetate/hexanes to afford a mixture of two compounds. Separate by normal phase HPLC eluting with standard hexane/ethanol gradient to afford (+/−)-trans-4-[(3,5-bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1carboxylic acid isopropyl ester (48 mg, 7%). $^1$H NMR (CDCl$_3$, 300 MHz): δ 0.95 (t, J=7.7 Hz, 3H), 1.33 (d, J=6.3 Hz, 3H), 1.35 (d, J=6.3 Hz, 3H), 1.55-1.69 (m, 2H), 2.31-2.47 (m, 3H), 3.98-4.00 (m, 2H), 4.49-4.73 (m, 5H), 5.09 (septuplet, J=7.5 Hz, 1H), 5.41 (dd, J=11.9, 7.5 Hz, 1H), 7.49 (d, J=8.7 Hz, 1H), 7.75 (s, 1H), 7.81 (s, 2H), 8.39 (d, J=8.6 Hz, 1H). MS (ES+): 670 (M+H).

and (+/−)-cis-4-[(3,5-bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester (132 mg, 19%). $^1$H NMR (CDCl$_3$, 300 MHz): δ 0.84 (t, J=7.4 Hz, 3H), 1.30 (d, J=6.3 Hz, 3H), 1.33 (d, J=6.3 Hz, 3H), 1.51-1.68 (m, 1H), 1.76-2.03 (m, 2H), 2.21 (t, J=6.5 Hz, 1H), 2.57-2.65 (m, 1H), 4.01-4.06 (m, 2H), 4.39-4.61 (m, 4H), 4.98-5.13 (m, 2H), 5.39 (dd, J=12.7, 4.0 Hz, 1H), 7.55 (d, J=8.3 Hz, 1H), 7.78 (s, 1H), 7.90 (s, 2H), 7.99 (d, J=8.5 Hz, 1H). MS (ES+): 670 (M+H).

Example 17

(2R,4S)-4-[(3,5-Bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester

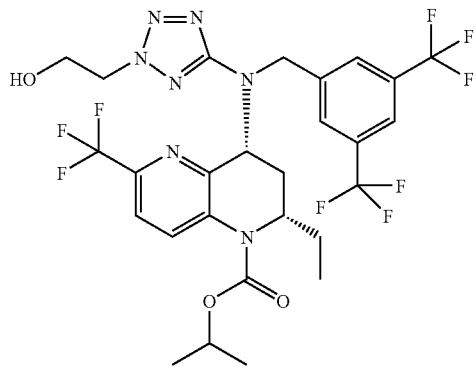

Obtain the title compound by chiral resolution of (+/−)-cis-4-[(3,5-bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester (Example 16) on a Chiralpak AD (4.6×250 mm), flow rate 1 mL/min, solvents: 15% propan-2-ol in hexane 0.2% dimethylethylamine, $R_t$=6.1 min, wavelength: 215.26 nm. EE>97%. MS (ES+): 670 (M+H).

Example 18

(2S,4R)-4-[(3,5-Bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester

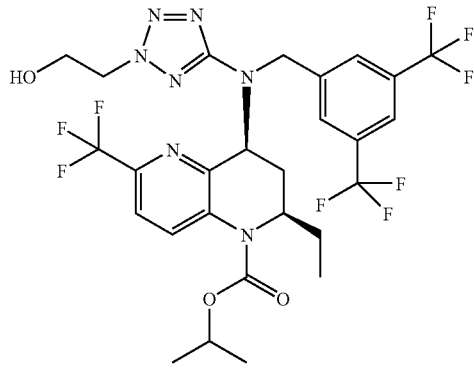

The title compound is obtained by chiral resolution of (+/−)-cis-4-[(3,5-bis-trifluoromethyl-benzyl)-[2-(2-hydroxy-ethyl)-2H-tetrazol-5-yl)-amino]-2-ethyl-6-trifluoromethyl-3,4-dihydro-2H-[1,5]naphthyridine-1-carboxylic acid isopropyl ester (Example 16) on a Chiralpak AD (4.6× 250 mm), flow rate 1 mL/min, solvents: 15% propan-2-ol in hexane 0.2% dimethylethylamine, R$_f$=9.3 min, wavelength: 215.26 nm. EE>97%. MS (ES+): 670 (M+H).

Example 19

(+/−)-4-[(3,5-Bis-trifluoromethyl-benzyl)-[2-methyl-2H-tetrazol-5-yl)-amino]-2-ethyl-6-trifluoromethyl-3,4-dihydro-2H-[1,5]naphthyridine-1-carboxylic acid isopropyl ester

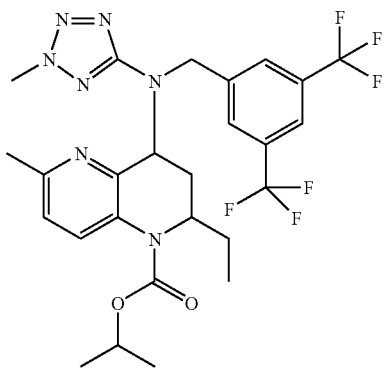

Step 1. Preparation of (+/−)-cis-4-[(3,5-Bis-trifluoromethyl-benzyl)-(2H-tetrazol-5-yl-amino)-2-ethyl-6-bromo-3,4-dihydro-2H-[1,5]naphthyridine-1-carboxylic acid isopropyl ester

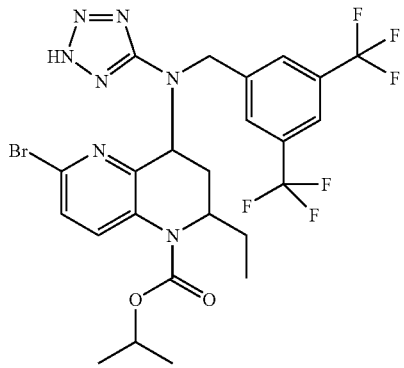

Prepare the title compound by essentially following the procedures described in Example 8 (Steps 1-2), by replacing (+/−)-cis-4-(3,5-bis-trifluoromethyl-benzylamino)-2-ethyl-6-methoxy-3,4-dihydro-2H-[1,5]naphthyridine-1-carboxylic acid isopropyl ester with (+/−)-cis-4-(3,5-bis-trifluoromethyl-benzylamino)-2-ethyl-6-bromo-3,4-dihydro-2H-[1,5] naphthyridine-1-carboxylic acid isopropyl ester in Example 8, Step 1. MS (ES+): 638, 640 (M+H).

Step 2. Preparation of (+/−)-cis-4-[(3,5-Bis-trifluoromethyl-benzyl)-(2H-tetrazol-5-yl-amino)-2-ethyl-6-methyl-3,4-dihydro-2H-[1,5]naphthyridine-1-carboxylic acid isopropyl ester

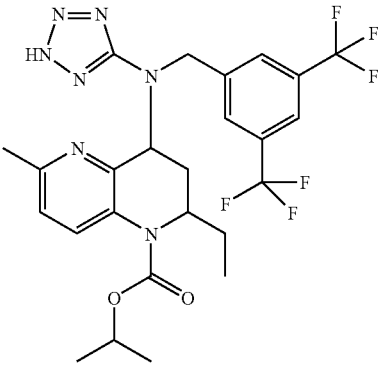

Prepare the title compound by essentially following the procedure described in Example 7, by replacing (+/−)-cis-4-[acetyl-(3,5-bis-trifluoromethyl-benzyl)-amino]-2-ethyl-6-bromo-3,4-dihydro-2H-[1,5]naphthyridine-1-carboxylic acid isopropyl ester with (+/−)-cis-4-[(3,5-bis-trifluoromethyl-benzyl)-(2H-tetrazol-5-yl-amino)-2-ethyl-6-bromo-3,4-dihydro-2H-[1,5]naphthyridine-1-carboxylic acid isopropyl ester. MS (ES+): 573 (M+H).

Step 3. Preparation of (+/−)-cis-4-[(3,5-Bis-trifluoromethyl-benzyl)-[2-methyl-2H-tetrazol-5-yl)-amino]-2-ethyl-6-trifluoromethyl-3,4-dihydro-2H-[1,5]naphthyridine-1-carboxylic acid isopropyl ester

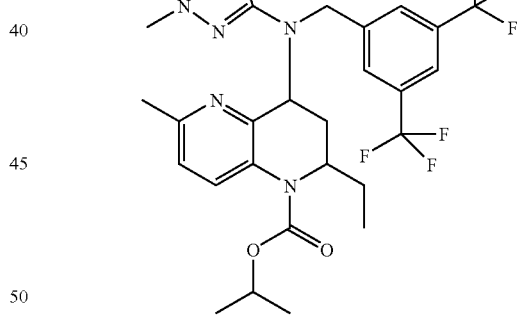

Prepare the title compound by essentially following the procedure described in Example 8, Step 3, by replacing (+/−)-cis-4-[(3,5-bis-trifluoromethyl-benzyl)-(2H-tetrazol-5-yl)-amino]-2-ethyl-6-methoxy-3,4-dihydro-2H-[1,5]naphthyridine-1-carboxylic acid isopropyl ester with (+/−)-cis-4-[(3,5-bis-trifluoromethyl-benzyl)-(2H-tetrazol-5-yl-amino)-2-ethyl-6-methyl-3,4-dihydro-2H-[1,5]naphthyridine-1-carboxylic acid isopropyl ester. 1H NMR (CDCl$_3$, 300 MHz): δ 0.79 (t, J=7.3 Hz, 3H), 1.27 (d, J=6.2 Hz, 3H), 1.32 (d, J=6.2 Hz, 3H), 1.41-1.56 (m, 1H), 1.71-1.82 (m, 1H), 1.87-1.99 (m, 1H), 2.36-2.44 (m, 4H), 4.15 (s, 3H), 4.23-4.39 (m, 1H), 4.65 (d, J=16.5 Hz, 1H), 4.97 (d, J=16.5 Hz, 1H), 4.99-5.09 (m, 1H), 5.27 (dd, J=12.7, 3.6 Hz, 1H), 7.12 (d, J=8.4 Hz, 1H), 7.77 (s, 1H), 7.85 (d, J=8.4 Hz, 1H), 7.93 (s, 2H). MS (ES+): 586 (M+H).

Example 20

(2R,4S)-4-[(3,5-Bis-trifluoromethyl-benzyl)-[2-methyl-2H-tetrazol-5-yl)-amino]-2-ethyl-6-trifluoromethyl-3,4-dihydro-2H-[1,5]naphthyridine-1-carboxylic acid isopropyl ester trifluoroacetate

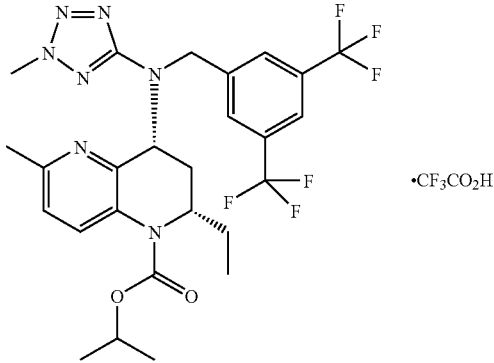

Obtain the title compound by chiral resolution of (+/−)-cis-4-[(3,5-bis-trifluoromethyl-benzyl)-[2-methyl-2H-tetrazol-5-yl)-amino]-2-ethyl-6-trifluoromethyl-3,4-dihydro-2H-[1,5]-naphthyridine-1-carboxylic acid isopropyl ester (Example 19, Step 3) on a Chiralpak AD (4.6×250 mm), flow rate 1 mL/min, solvents: hexane-trifluoroacetic acid 0.05%/ethanol. Isocratic mode 5% ethanol, $R_f$=4.7 min, wavelength: 215.26 nm. EE>97%. MS (ES+): 586 (M+H).

Example 21

(2S,4R)-4-[(3,5-Bis-trifluoromethyl-benzyl)-[2-methyl-2H-tetrazol-5-yl)-amino]-2-ethyl-6-trifluoromethyl-3,4-dihydro-2H-[1,5]naphthyridine-1-carboxylic acid isopropyl ester trifluoroacetate

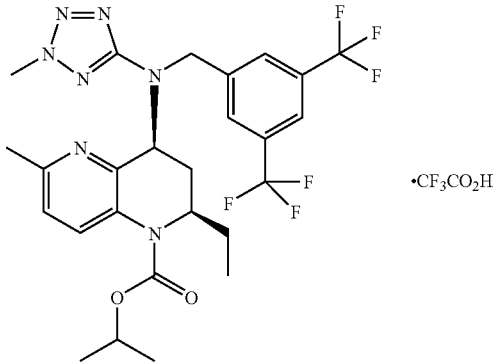

Obtain the title compound by chiral resolution of (+/−)-cis-4-[(3,5-bis-trifluoromethyl-benzyl)-[2-methyl-2H-tetrazol-5-yl)-amino]-2-ethyl-6-tri fluoromethyl-3,4-dihydro-2H-[1,5]-naphthyridine-1-carboxylic acid isopropyl ester (Example 19, step 3) on a Chiralpak AD (4.6×250 mm), flow rate 1 mL/min, solvents: hexane-trifluoroacetic acid 0.05%/ethanol. Isocratic mode 5% ethanol, $R_f$=5.3 min, wavelength: 215.26 nm. EE>97%. MS (ES+): 586 (M+H).

Example 22

(+/−)-cis-4-[[2-(2-Amino-ethyl)-2H-tetrazol-5-yl]-(3,5-bis-trifluoromethyl-benzyl)-amino]-2-ethyl-6-methyl-3,4-dihydro-2H-[1,5]naphthyridine-1-carboxylic acid isopropyl ester

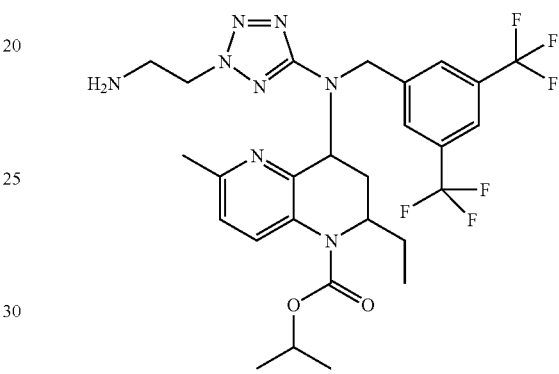

Step 1. Preparation of (+/−)-cis-4-[(3,5-Bis-trifluoromethyl-benzyl)-[2-(2-tert-butoxycarbonylamino-ethyl)-2H-tetrazol-5-yl)-amino]-2-ethyl-6-methyl-3,4-dihydro-2H-[1,5]naphthyridine-1-carboxylic acid isopropyl ester

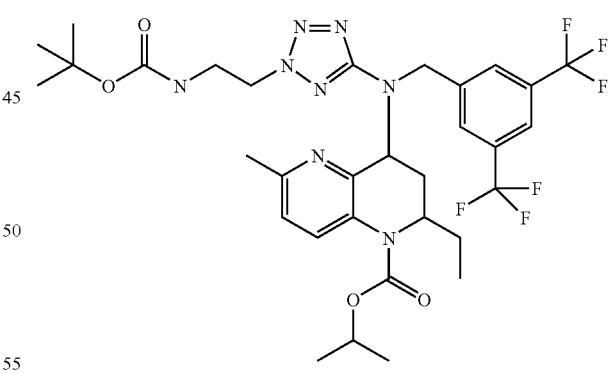

Prepare the title compound by essentially following the procedures described in Example 12, by replacing (+/−)-cis-4-[(3,5-bis-trifluoromethyl-benzyl)-(2H-tetrazol-5-yl)-amino]-2-ethyl-6-trifluoromethyl-3,4-dihydro-2H-[1,5] naphthyridine-1-carboxylic acid isopropyl ester with (+/−)-cis-4-[(3,5-bis-trifluoromethyl-benzyl)-(2H-tetrazol-5-yl-amnino)-2-ethyl-6-methyl-3,4-dihydro-2H-[1,5] naphthyridine-1-carboxylic acid isopropyl ester. MS (ES+): 715 (M+H).

Step 2. Preparation of (+/−)-cis-4-[[2-(2-amino-ethyl)-2H-tetrazol-5-yl]-(3,5-bis-trifluoromethyl-benzyl)-amino]-2-ethyl-6-methyl-3,4-dihydro-2H-[1,5]naphthyridine-1-carboxylic acid isopropyl ester

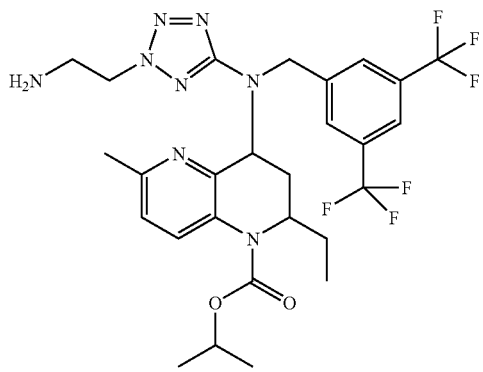

Prepare the title compound by essentially following the procedures described in Example 13, by replacing (+/−)-cis-4-[(3,5-bis-trifluoromethyl-benzyl)-[2-(2-tert-butoxycarbonylamino-ethyl)-2H-tetrazol-5-yl)-amino]-2-ethyl-6-trifluoromethyl-3,4-dihydro-2H-[1,5]naphthyridine-1-carboxylic acid isopropyl ester with (+/−)-cis-4-[(3,5-bis-trifluoromethyl-benzyl)-[2-(2-tert-butoxycarbonylamino-ethyl)-2H-tetrazol-5-yl)-amino]-2-ethyl-6-methyl-3,4-dihydro-2H-[1,5]naphthyridine-1-carboxylic acid isopropyl ester. MS (ES+): 615 (M+H).

Example 23

(+/−)-cis-4-[(3,5-Bis-trifluoromethyl-benzyl)-[2-(2-hydroxy-ethyl)-2H-tetrazol-5-yl)-amino]-2-ethyl-6-methyl-3,4-dihydro-2H-[1,5]naphthyridine-1-carboxylic acid isopropyl ester

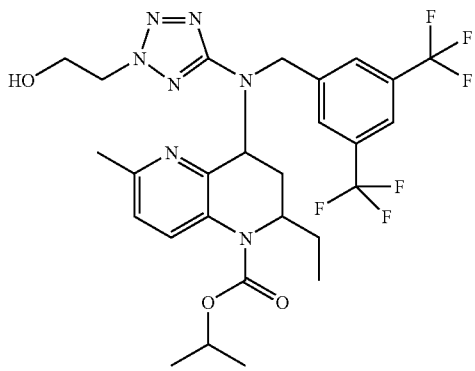

Prepare the title compound by essentially following the procedures described in Example 16, by replacing (+/−)-cis-4-[(3,5-bis-trifluoromethyl-benzyl)-(2H-tetrazol-5-yl)-amino]-2-ethyl-6-trifluoromethyl-3,4-dihydro-2H-[1,5]naphthyridine-1-carboxylic acid isopropyl ester with (+/−)-cis-4-[(3,5-bis-trifluoromethyl-benzyl)-(2H-tetrazol-5-yl-amino)-2-ethyl-6-methyl-3,4-dihydro-2H-[1,5]naphthyridine-1-carboxylic acid isopropyl ester. MS (ES+): 616 (M+H).

Example 24

(+/−)-cis-6-Amino-4-[(3,5-bis-trifluoromethyl-benzyl)-[2-methyl-2H-tetrazol-5-yl)-amino]-2-ethyl-7-methyl-3,4-dihydro-2H-[1,5]naphthyridine-1-carboxylic acid isopropyl ester

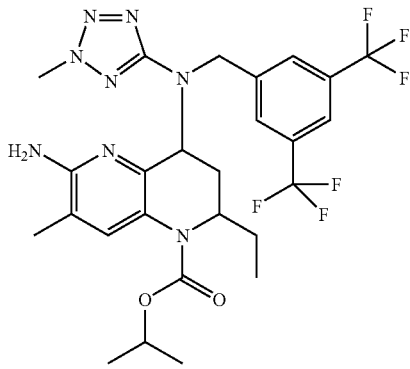

Step 1. Preparation of Benzyl-(3-methyl-5-nitro-pyridin-2-yl)-amine

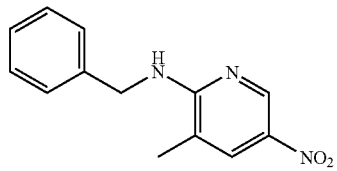

Heat at 100° C. a mixture of 2-chloro-3-methyl-5-nitropyridine (3.0 g, 17.39 mmol), benzylamine (2.85 mL, 26.08 mmol), palladium (II) acetate (195 mg, 0.869 mmol), 2,2'-bis(diphenylphosphino)-1,1'-binaphthyl (BINAP) (812 mg, 1.30 mmol) and sodium tert-butoxide (2.58 g, 26.08 mmol) in dry toluene (15 mL) under an atmosphere of nitrogen for 15 h. Cool to room temperature, add water, separate the layers and extract the aqueous layer with ethyl acetate. Dry the combined organic layers over anhydrous sodium sulfate, filter, and remove the solvent under reduced pressure. Purify the residue by silica gel chromatography, eluting with hexanes/ethyl acetate, to afford the title compound (2.12 g, 50%). MS (ES−): 242 (M−H).

Step 2. Preparation of benzyl-3-methyl-pyridine-2,5-diamine

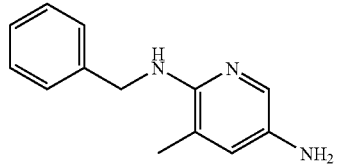

Heat at 90° C. a mixture of benzyl-(3-methyl-5-nitro-pyridin-2-yl)-amine (2.1 g, 8.63 mmol), ammonium formate (2.17 g, 34.52 mmol) and 10% palladium on carbon (0.2 g) in ethanol (30 mL) for 3 h. Filter through Celite® and evaporate the solvent its vacuo. Purify the residue using a SCX cartridge to afford the title compound (652 mg, 35%). MS (ES+): 214 (M+H).

Step 3. Preparation of (+/−)-cis-(6-Benzylamino-2-ethyl-7-methyl-1,2,3,4-tetrahydro-[1,5]naphthyridin-4-yl)acetamide

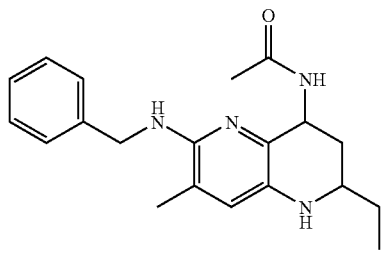

Prepare the title compound by essentially following the procedures described in Example 3, Step 1, by replacing 6-methoxy-pyridin-3-yl-amine with benzyl-3-methyl-pyridine-2,5-diamine. MS (ES+): 339 (M+H).

Step 4. Preparation of (+/−)-cis-4-Acetylamino-6-benzylamino-2-ethyl-7-methyl-3,4-dihydro-2H-[1,5]naphthyridine-1-carboxylic acid isopropyl ester

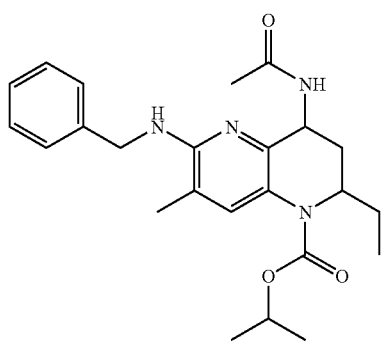

Prepare the title compound by essentially following the procedures described in Example 3, Step 2, by replacing (+/−)-cis-(2-ethyl-6-methoxy-1,2,3,4-tetrahydro-[1,5]naphthyridin-4-yl)acetamide with (+/−)-cis-(6-benzylamino-2-ethyl-7-methyl-1,2,3,4-tetrahydro-[1,5]naphthyridin-4-yl)acetamide. MS (ES+): 425 (M+H).

Step 5. Preparation of (+/−)-cis-4-Amino-6-benzylamino-2-ethyl-7-methyl-3,4-dihydro -2H-[1,5]naphthyridine-1-carboxylic acid isopropyl ester

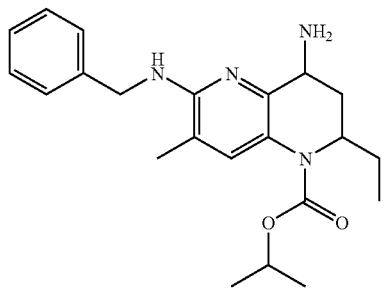

Prepare the title compound by essentially following the procedure described in Example 3, Step 3, by replacing (+/−)-cis-4-acetylamino-2-ethyl-6-methoxy-3,4-dihydro-2H-[1,5]naphthyridine-1-carboxylic acid isopropyl ester with (+/−)-cis-4-acetylamino-6-benzylamino-2-ethyl-7-methyl-3,4-dihydro-2H-[1,5]naphthyridine-1-carboxylic acid isopropyl ester. MS (ES+): 383 (M+H).

Step 6. Preparation of (+/−)-cis-6-Benzylamino-4-(3,5-bis-trifluoromethyl-benzylamino)-2-ethyl-7-methyl-3,4-dihydro-2H-[1,5]naphthyridine-1-carboxylic acid isopropyl ester

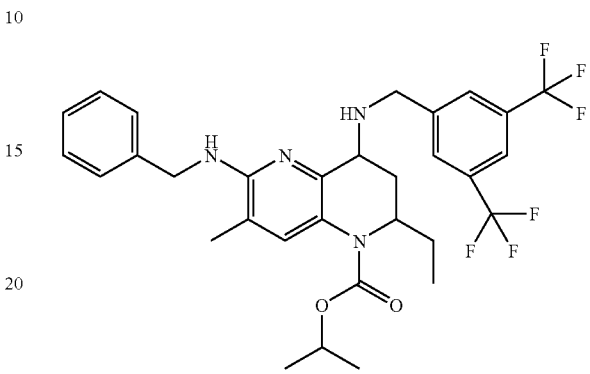

Prepare the title compound by essentially following the procedure described in Example 3, Step 4, by replacing (+/−)-cis-4-amino-2-ethyl-6-methoxy-3,4-dihydro-2H-[1,5]-naphthyridine-1-carboxylic acid isopropyl ester with (+/−)-cis-4-amino-6-benzylamino-2-ethyl-7-methyl-3,4-dihydro-2H-[1,5]naphthyridine-1-carboxylic acid isopropyl ester. MS (ES+): 609 (M+H).

Step 7. Preparation of (+/−)-cis-6-Benzylamino-4-[(3,5-bis-trifluoromethyl-benzyl)-cyano-amino]-2-ethyl-7-methyl-3,4-dihydro-2H-[1,5]naphthyridine-1-carboxylic acid isopropyl ester

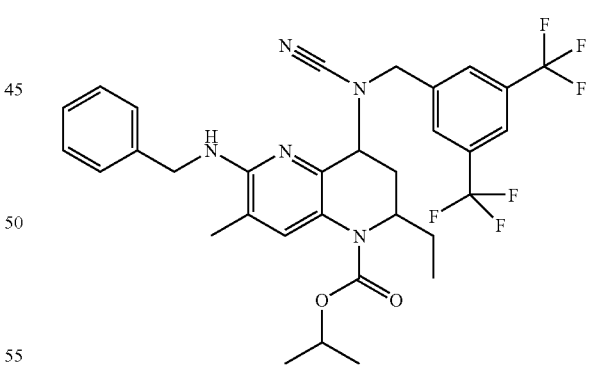

Prepare the title compound by essentially following the procedure described in Example 8, Step 1, by replacing (+/−)-cis-4-[(3,5-bis-trifluoromethyl-benzyl)-amino]-2-ethyl-6-methoxy-3,4-dihydro-2H-[1,5]naphthyridine-1-carboxylic acid isopropyl ester with (+/−)-cis-6-benzylamino-4-(3,5-bis-trifluoromethyl-benzylamino)-2-ethyl-7-methyl-3,4-dihydro-2H-[1,5]naphthyridine-1-carboxylic acid isopropyl ester. MS (ES+): 634 (M+H).

Step 8. Preparation of (+/−)-cis and trans-6-Benzylamino-4-[(3,5-bis-trifluoromethyl-benzyl)-(2-methyl-2H-tetrazol-5-yl)-amino]-2-ethyl-7-methyl-3,4-dihydro-2H-[1,5]naphthyridine-1-carboxylic acid isopropyl ester

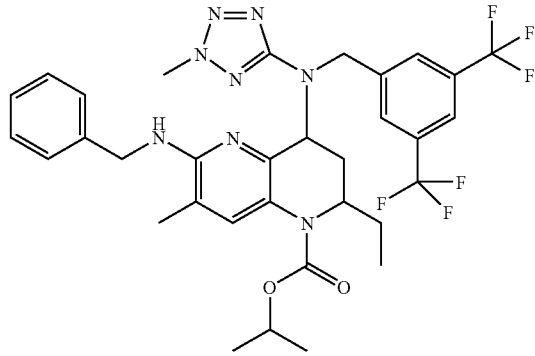

Heat at 110° C. a mixture of (+/−)-cis-6-benzylamino-4-[(3,5-bis-trifluoromethyl-benzyl)-cyano-amino]-2-ethyl-7-methyl-3,4-dihydro-2H-[1,5]naphthyridine-1-carboxylic acid isopropyl ester (110 mg, 0.174 mmol), sodium azide (16 mg, 0.244 mmol) and triethyl amine hydrochloride (33 mg, 0.244 mmol) in dry toluene under a nitrogen atmosphere for 15 h. Then add more sodium azide (10 mg) and triethyl amine hydrochloride (25 mg) and heat the mixture for 20 h. Cool to room temperature, dilute with ethyl acetate, and wash with 1 N HCl. Dry the organic layer over anhydrous sodium sulfate, filter, and remove the solvent under reduced pressure. Purify the residue by flash chromatography, eluting with hexanes/ethyl acetate. Dissolve the residue in dry dichloromethane (1 mL), add triphenylphosphine (38 mg, 0.146 mmol), methanol (22 mg, 0.66 mmol) followed by diisopropylazodicarboxylate (0.046 mL, 0.104 mmol) and stir the mixture for 15 h at room temperature. Remove the solvent in vacuo and purify the residue by silica gel chromatography, eluting with ethyl acetate/hexanes to afford (+/−)-trans-4-[(3,5-bis-trifluoromethyl-benzyl)-2-methyl-2H-tetrazol-5-yl)-amino]-2-ethyl-6-benzylamino-7-methyl-3,4-dihydro-2H-[1,5]naphthyridine-1-carboxylic acid isopropyl ester [15 mg, 16%, MS (ES+): 691 (M+H)] and (+/−)-cis-4-[(3,5-bis-trifluoromethyl-benzyl)-2-methyl-2H-tetrazol-5-yl)-amino]-2-ethyl-6-benzylamino-7-methyl-3,4-dihydro-2H-[1,5]naphthyridine-1-carboxylic acid isopropyl ester [20 mg, 22%, MS (ES+): 691 (M+H)].

Step 9. Preparation of (+/−)-cis-6-Amino-4-[(3,5-bis-trifluoromethyl-benzyl)-(2-methyl-2H-tetrazol-5-yl)-amino]-2-ethyl-7-methyl-3,4-dihydro-2H-[1,5]naphthyridine-1-carboxylic acid isopropyl ester

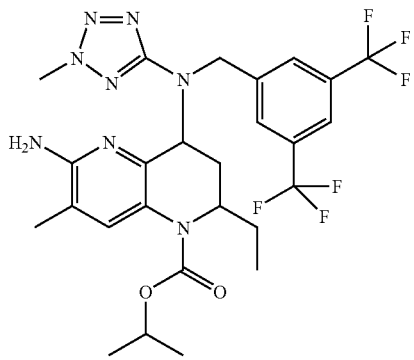

Stir at room temperature a mixture of (+/−)-cis-4-[(3,5-bis-trifluoromethyl-benzyl)-2-methyl-2H-tetrazol-5-yl)-amino]-2-ethyl-6-benzylamino-7-methyl-3,4-dihydro-2H-[1,5]naphthyridine-1-carboxylic acid isopropyl ester (20 mg, 0.029 mmol) and 10% palladium on carbon (2 mg) in methanol (1 mL) under an atmosphere of hydrogen for 20 h. Filter through Celite®, evaporate the solvent in vacuo, and purify the residue by using a silica gel cartridge, eluting with hexanes/ethyl acetate 1:1 to afford the title compound (8 mg, 44%). $^1$H NMR (CDCl$_3$, 300 MHz): δ 0.79 (t, J=7.3 Hz, 3H), 1.26 (d, J=6.2 Hz, 3H), 1.30 (d, J=6.2 Hz, 3H), 1.41-1.50 (m, 1H), 1.61-1.72 (m, 2H), 2.09 (s, 3H), 2.42-2.51 (m, 1H), 4.13 (s, 3 H), 4.32-4.39 (m, 1H), 4.47 (d, J=17.2 Hz, 1H), 4.95-5.04 (m, 2 H), 5.28 (dd, J=12.1, 4.4 Hz, 1H), 7.41 (s, 1H), 7.74 (s, 1H), 7.91 (s, 2H). MS (ES+): 601 (M+H).

Example 25

(+/−)-trans-6-Amino-4-[(3,5-bis-trifluoromethyl-benzyl)-(2-methyl-2H-tetrazol-5-yl)-amino]-2-ethyl-7-methyl-3,4-dihydro-2H-[1,5]naphthyridine-1-carboxylic acid isopropyl ester

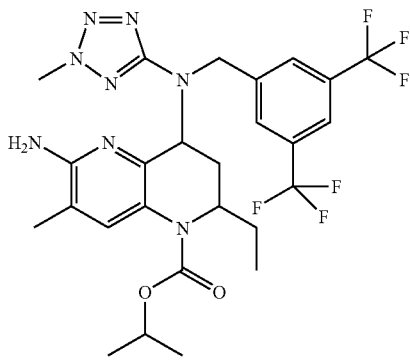

Prepare the title compound by essentially following the procedure described in Example 24, Step 9, by replacing (+/−)-cis 4-[(3,5-bis-trifluoromethyl-benzyl)-2-methyl-2H-tetrazol-5-yl)-amino]-2-ethyl-6-benzylamino-7-methyl-3,4-dihydro-2H-[1,5]naphthyridine-1-carboxylic acid isopropyl ester with (+/−)-trans 4-[(3,5-bis-trifluoromethyl-benzyl)-2-methyl-2H-tetrazol-5-yl)-amino]-2-ethyl-6-benzylamino-7-methyl-3,4-dihydro-2H-[1,5]naphthyridine-1-carboxylic acid isopropyl ester. $^1$H NMR (CDCl$_3$, 300 MHz): δ 0.90 (t, J=7.3 Hz, 3H), 1.28 (d, J=6.2 Hz, 3H), 1.31 (d, J=6.2 Hz, 3H), 1.51-1.60 (m, 2H), 2.05 (s, 3H), 2.07-2.16 (m, 1H), 2.27-2.34 (m, 1 H), 4.14 (s, 3 H), 4.31-4.57 (m, 3 H), 5.03 (septuplet, J=6.2 Hz, 1H), 5.40 (dd, J=10.6, 7.7 Hz, 1H), 7.60 (bs, 1H), 7.67 (s, 1H), 7.82 (s, 2H). MS (ES+): 601 (M+H).

Example 26

(+/−)-cis-4-[(3,5-Bis-triflu)romethyl-benzyl)-(2-methyl-2H-tetrazol-5-yl)-amino]-2-ethyl-6-methoxy-7-methyl-3,4-dihydro-2H-[1,5]naphthyridine-1-carboxylic acid isopropyl ester

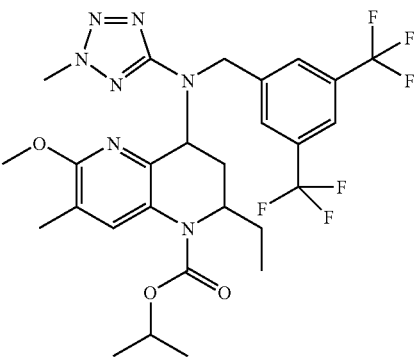

Step 1. Preparation of 2-Methoxy-3-methyl-5-nitro-pyridine

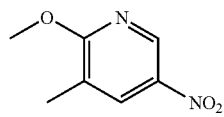

Add sodium methoxide 30% in methanol (3.26 mL, 17.4 mmol) to a solution of 2-chloro-3-methyl-5-nitro-pyridine (1.0 g, 5.8 mmol) in methanol (5 mL) and heat the mixture at 100° C. under a nitrogen atmosphere for 6 h. Remove the solvent under reduced pressure, suspend the residue in water, and extract with dichloromethane. Dry the organic layer over anhydrous sodium sulfate, filter, and remove the solvent under reduced pressure to afford the title compound (859 mg, 88%). $^1$H NMR (CDCl$_3$, 300 MHz): δ 2.26 (s, 3H), 4.07 (s, 3H), 8.17 (d, J=2.8Hz, 1H), 8.92 (d, J=2.4Hz, 1H).

Step 2. Preparation of 2-methoxy-3-methyl-pyridine-3-ylamine

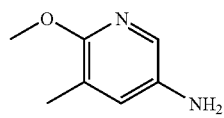

Prepare the title compound by essentially following the procedure described in Example 24, Step 2, by replacing benzyl-(3-methyl-5-nitro-pyridin-2-yl)-amine with 2-methoxy-3-methyl-5-nitro-pyridine, heating the mixture for 1 h. MS (ES+): 139 (M+H).

Step 3. Preparation of (+/−)-cis-4-(3,5-Bis-trifluoromethyl-benzylamino)-2-ethyl-6-methoxy-7-methyl-3,4-dihydro-2H-[1,5]naphthyridine-1-carboxylic acid isopropyl ester

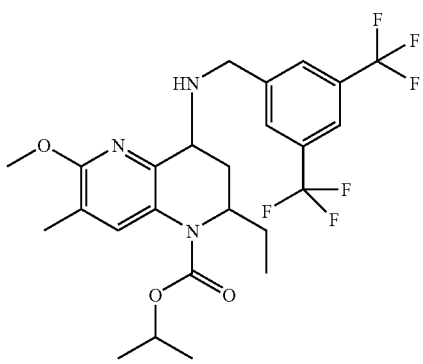

Prepare the title compound by essentially following the procedures described in Example 3, Steps 1-4, by replacing 6-methoxy-pyridin-3-ylamine with 2-methoxy-3-methyl-pyridine-3-ylamine in Example 3, Step 1. MS (ES+): 534 (M+H).

Step 4. Preparation of (+/−)-cis-4-[(3,5-bis-trifluoromethyl-benzyl)-(2-methyl-2H-tetrazol-5-yl)-amino]-2-ethyl-6-methoxy-7-methyl-3,4-dihydro-2H-[1,5]naphthyridine-1-carboxylic acid isopropyl ester

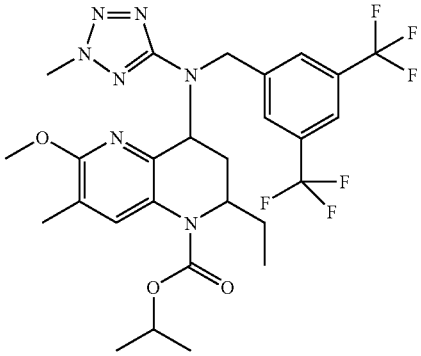

Prepare the title compound by essentially following the procedures described in Example 8, Steps 1-3, by replacing (+/−)-cis-4-(3,5-bis-trifluoromethyl-benzylamino)-2-ethyl-6-methoxy-3,4-dihydro-2H-[1,5]naphthyridine-1-carboxylic acid isopropyl ester with (+/−)-cis-4-(3,5-Bis-trifluoromethyl-benzylamino)-2-ethyl-6-methoxy-7-methyl-3,4-dihydro-2H-[1,5]naphthyridine-1-carboxylic acid isopropyl ester in Example 8 Step 1. MS (ES+): 616 (M+H).

Example 27

(2R,4S)-4-[(3,5-Bis-tifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid ethyl ester

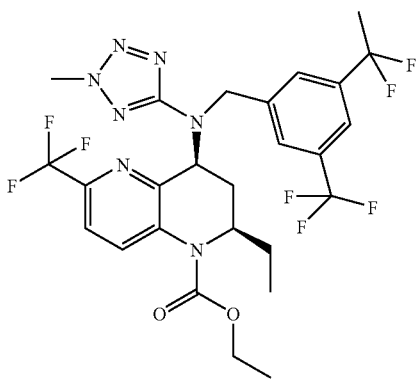

Step 1. Preparation of (2R,4S)-(3,5-Bis-trifluoromethyl-benzyl)-(2-ethyl-6-trifluoromethyl-1,2,3,4-tetrahydro-[1,5]naphthyridin-4-yl)-(2-methyl-2H-tetrazol-5-yl)-amine

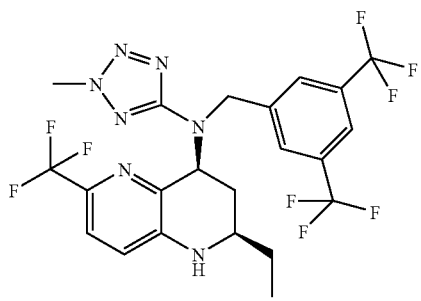

Add sulphuric acid 98% (7 mL) to a solution of (2R,4S)-4-[(3,5-bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid isopropyl ester (Example 11) (3.30 g, 5.60 mmol) in trifluoroacetic acid (88 mL). Stir the mixture at room temperature overnight. Concentrate and dissolve the residue in dichloromethane. Wash with saturated NaHCO₃ and brine. Dry the organic layers over Na₂SO₄, filter, and concentrate to afford the title compound (2.88 g, 100%). MS (ES+): 554 (M+H).

Step 2. Preparation of (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carbonyl chloride

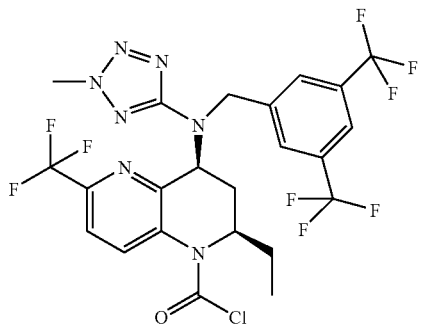

Add trichloromethyl chloroformate (0.36 mL, 3.02 mmol) to a solution of (2R,4S)-(3,5-Bis-trifluoromethyl-benzyl)-(2-ethyl-6-trifluoromethyl-1,2,3,4-tetrahydro-[1,5]naphthyridin-4-yl)-(2-methyl-2H-tetrazol-5-yl)-amine (1.67 g, 3.02 mmol) and triethylamine (0.84 mL, 6.04 mmol) in toluene (19 mL). Stir the mixture at room temperature under nitrogen for 3 h, then add more triethylamine (0.50 mL, 3.6 mmol) and trichloromethyl chloroformate (0.21 mL, 1.8 mmol). Stir the mixture overnight. Evaporate the solvent and purify the residue by silica gel chromatography (elution with hexane/ethyl acetate) to afford the title compound (1.83 g, 98%). MS (ES+): 616 (M+H).

Step 3. Preparation of (2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid ethyl ester

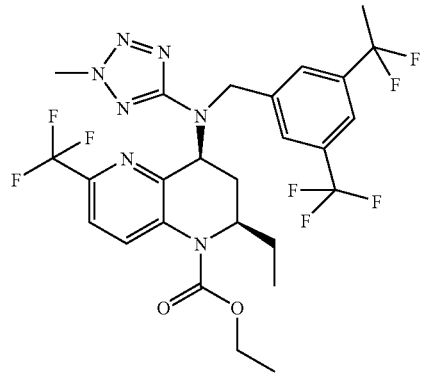

Add triethylamine (25 µL) and 4-dimethylaminopyridine (10 mg, 80 µmol) to a solution of (2R,4S)-4-[(3,5-bis-trifluoromethyl-benzyl)-(2-methyl-2H-tetrazol-5-yl)-amino]-2-ethyl-6-trifluoromethyl-3,4-dihydro-2H-[1,5]naphthyridine-1-carbonyl chloride (100 mg, 0.16 mmol) and ethanol (28 µL) in dichloromethane (0.9 mL). Stir the mixture at room temperature for 8 h. Evaporate the solvent and purify the crude material by silica gel chromatography (elution with hexane/ethyl acetate) to afford the title compound (51 mg, 51%). MS (ES+): 626 (M+H).

Example 28

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-dimethylamino-ethyl ester

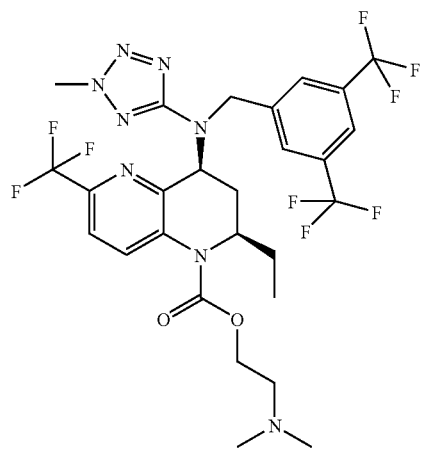

Prepare the title compound by essentially following the procedure as described in Example 27, by replacing ethanol with 2-dimethylamino-ethanol in Example 27, Step 3. MS (ES+): 669 (M+H).

Example 29

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid tetrahydro-pyran-4-yl ester

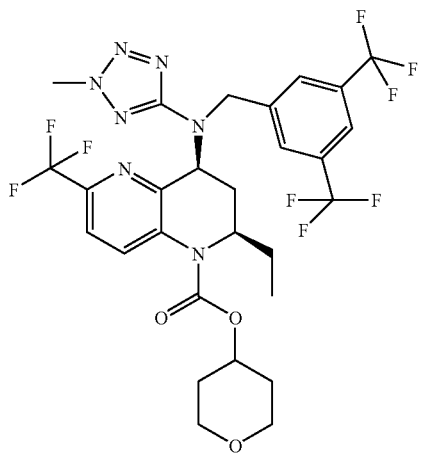

Prepare the title compound by essentially following the procedure as described in Example 27, by replacing ethanol with tetrahydro-pyran-4-ol in Example 27, Step 3. MS (ES+): 682 (M+H).

Example 30

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 1-methyl-piperidin-4-yl ester

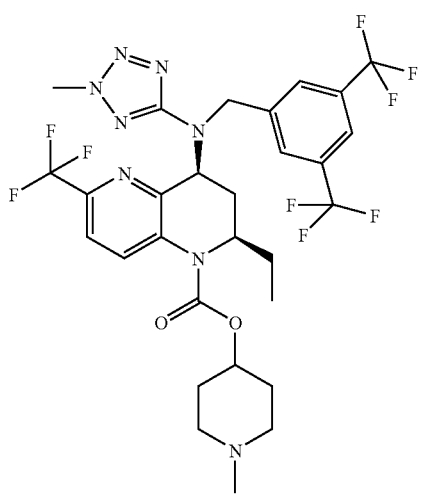

Prepare the title compound by essentially following the procedure as described in Example 27, by replacing ethanol with 1-methyl-piperidin-4-ol in Example 27, Step 3. MS (ES+): 695 (M+H).

Example 31

(2R,3'R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid tetrahydro-furan-3-yl ester

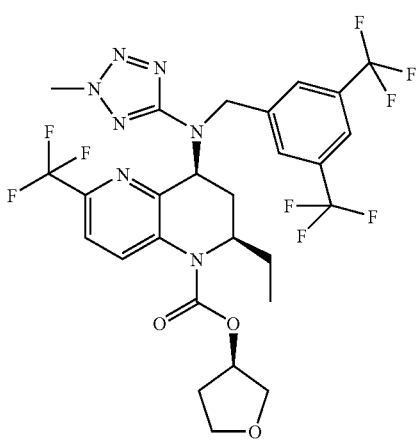

Prepare the title compound by essentially following the procedure as described in Example 27 by replacing ethanol with 3R-tetrahydro-furan-3-ol in Example 27, Step 3. MS (ES+): 668 (M+H).

Example 32

(2R,3'S,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid tetrahydro-furan-3-yl ester

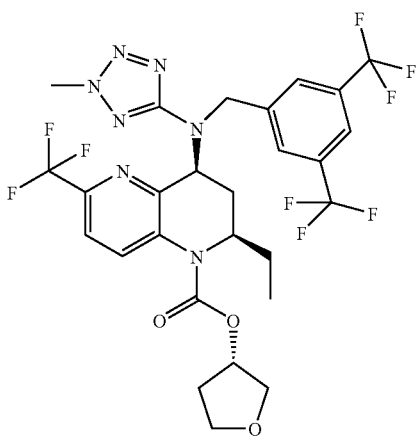

Prepare the title compound by essentially following the procedure as described in Example 27 by replacing ethanol with 3S-tetrahydro-furan-3-ol in Example 27, Step 3. MS (ES+): 668 (M+H).

Example 33

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-morpholin-4-yl-ethyl ester

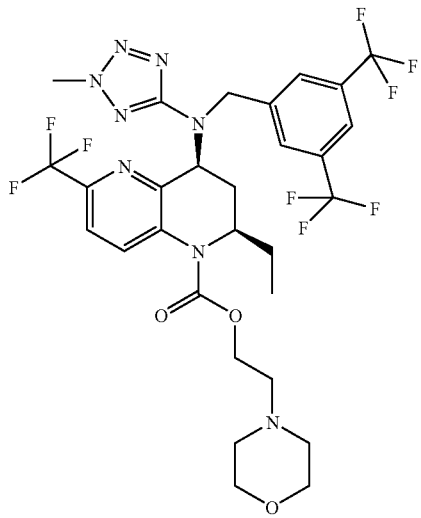

Prepare the title compound by essentially following the procedure as described in Example 27 by replacing ethanol with 2-molpholin-4-yl-ethanol in Example 27, Step 3. MS (ES+): 711 (M+H).

Example 34

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-(4-methyl-piperazin-1-yl)-ethyl ester

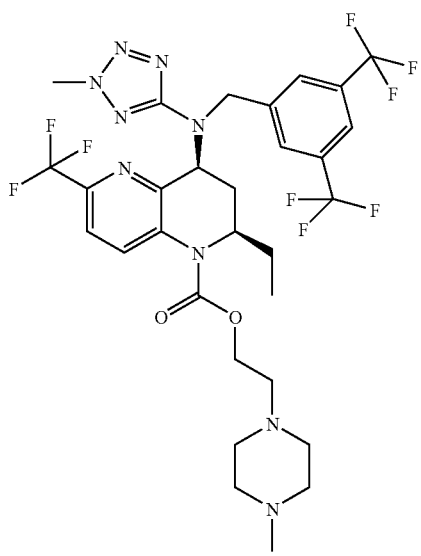

Prepare the title compound by essentially following the procedure as described in Example 27 by replacing ethanol with 2-(4-methyl-piperazin-1-yl)-ethanol in Example 27, Step 3. MS (ES+): 724 (M+H).

Example 35

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-methoxycarbonyl-2-methyl-propyl ester

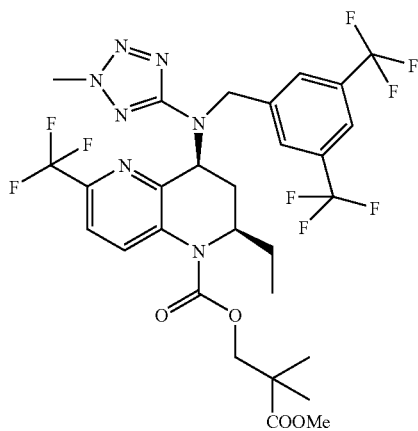

Prepare the title compound by essentially following the procedure as described Example 27, by replacing ethanol with 3-hydroxy-2,2-dimethyl-propionic acid methyl ester in Example 27, Step 3. MS (ES+): 712 (M+H).

Example 36

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-carboxy-2-methyl-propyl ester

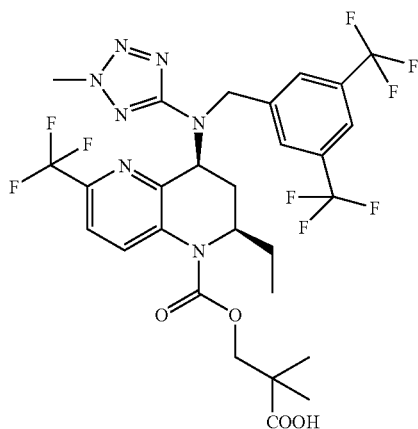

Add LiOH 2.5 M (1.9 mL, 4.8 mmol) to a solution of (2R,4S)-4-[(3,5-bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-methoxycarbonyl-2-methyl-propyl ester (74 mg, 0.10 mmol) in THF (1.9 mL). Stir the mixture at room temperature for 72 h. Acidify with 1 M HCl. Extract the aqueous phase with dichloromethane. Dry the organic layers over $Na_2SO_4$, filter, and concentrate. Purify the residue using silica gel chromatography (elution with hexane/ethyl acetate) to afford the title compound (14 mg, 20%). MS (ES+): 698 (M+H).

Example 37

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-cyano-ethyl ester

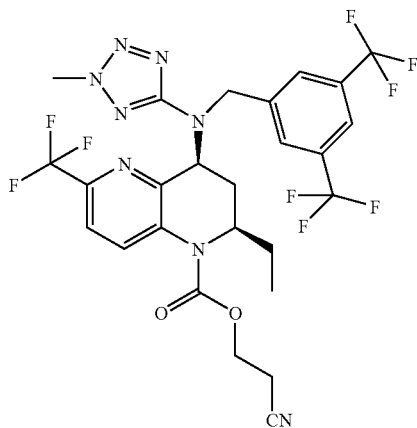

Prepare the title compound by essentially following the procedure as described in Example 27, by replacing ethanol with 3-hydroxy-propionitrile in Example 27, Step 3. MS (ES+): 651 (M+H).

Example 38

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-(2H-tetrazol-5-yl)-ethyl ester

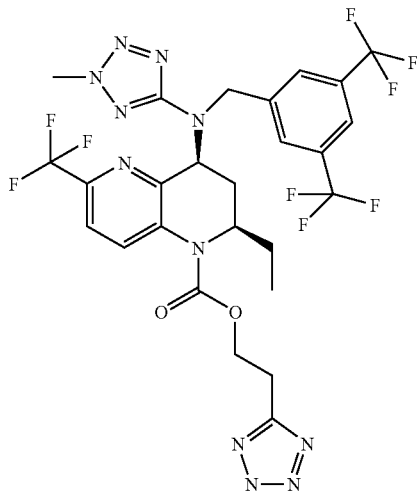

Add sodium azide (16 mg, 0.24 mmol) and triethylamine hydrochloride (33 mg, 0.24 mmol) to a solution of (2R,4S)-4-[(3,5-bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-cyano-ethyl ester (77 mg, 0.12 mmol) in toluene (2.4 mL). Stir the mixture at 80° C. for 1.5 h and at 100° C. overnight. Add more sodium azide (24 mg, 0.36 mmol) and triethylamine hydrochloride (50 mg, 0.36 mmol) and stir the mixture for 8 h at 100° C. Add more sodium azide (24 mg, 0.36 mmol) and triethylamine hydrochloride (50 mg, 0.36 mmol) and stir the mixture for 6 h at 100° C. Cool down to room temperature. Add 1 M HCl and extract the aqueous phase with dichloromethane. Wash the organic layers with water and brine, then dry over $Na_2SO_4$, filter, and concentrate. Purify the crude material by silica gel chromatography (elution with dichloromethane/methanol) to afford the title compound (55 mg, 66%). MS (ES+): 694 (M+H).

Example 39

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-benzyloxy-ethyl ester

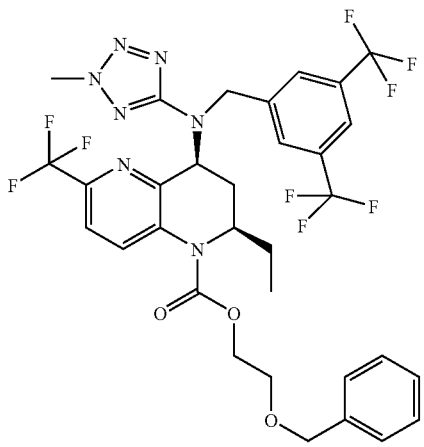

Prepare the title compound by essentially following the procedure as described in Example 27 by replacing ethanol with 2-benzyloxy-ethanol in Example 27, Step 3. MS (ES+): 732 (M+H).

Example 40

(2R,4S)-4-[(3,5-Bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-hydroxy-ethyl ester

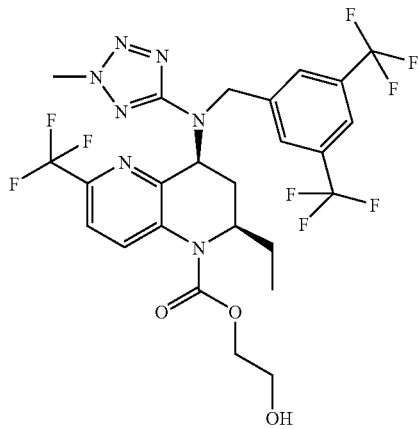

Stir a mixture of (2R,4S)-4-[(3,5-bis-trifluoromethyl-benzyl)-(2-methyl-2H-tetrazol-5-yl)-amino]-2-ethyl-6-trifluoromethyl-3,4-dihydro-2H-[1,5]naphthyridine-1-carboxylic acid 2-benzyloxy-ethyl ester (69 mg, 94 µmol) and Pd/C 10% (7 mg) in MeOH (1 mL) under a hydrogen atmosphere for 1 h. Filter the mixture over a pad of Celite®. Wash the solids with dichloromethane. Concentrate the filtrate and purified by silica gel chromatography (elution with hexane/ethyl acetate) to afford the title compound (45 mg, 75%). MS (ES+): 642 (M+H).

Example 41

(+/−)-cis-4-[(3,5-Bistrifluoromethylbenzyl)-(5-methyl-1H-pyrazol-3-yl)amino]-2-ethyl-6-trifluoromethyl-3,4-dihydro-2H-[1,5]naphthyridine-1-carboxylic acid isopropyl ester

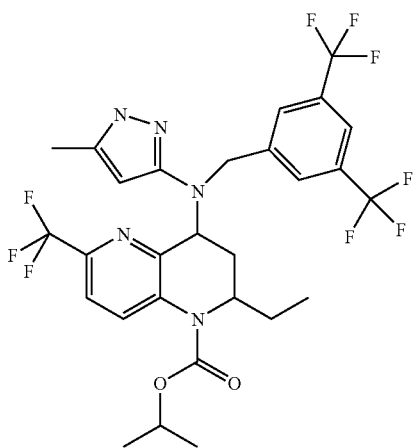

Step 1. Preparation of (+/−)-cis-4-[(3,5-Bis-trifluoromethyl-benzyl)-(3-oxo-butyryl)-amino]-2-ethyl-6-trifluoromethyl-3,4-dihydro-2H-[1,5]naphthyridine-1-carboxylic acid isopropyl ester

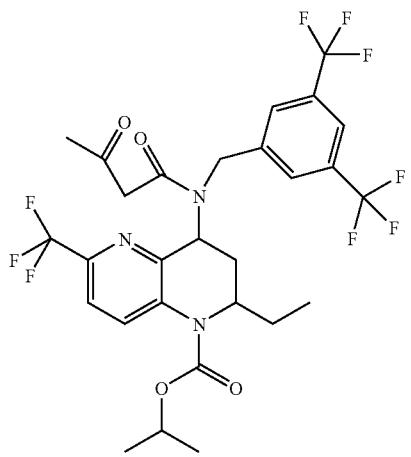

Add a solution of diketene (0.539 mL, 6.99 mmol) in dry THF (3.7 mL) to a solution of (+/−)-cis-4-(3,5-Bis-trifluoromethyl-benzylamino)-2-ethyl-6-trifluoromethyl-3,4-dihydro-2H-[1,5]naphthyridine-1-carboxylic acid isopropyl ester (from Example 4) (1.95 g, 3.49 mmol) and dimethylaminopyridine (55 mg, 0.45 mmol) in dry THF (12.5 mL) at 0° C. under nitrogen atmosphere. Stir the mixture at 0° C. for 5 min and 4 h at room temperature. Then remove the solvents under reduced pressure and purify the residue by flash chromatography, eluting with hexanes/ethyl acetate, to afford the title compound (1.97 g, 85%): MS (ES+): 642 (M+H).

Step 2. Preparation of (+/−)-cis-4-[(3,5-bistrifluoromethyl-benzyl)-(5-methyl-1H-pyrazol-3-yl)amino]-2-ethyl-6-trifluoromethyl-3,4-dihydro-2H-[1,5]naphthyridine-1-carboxylic acid isopropyl ester

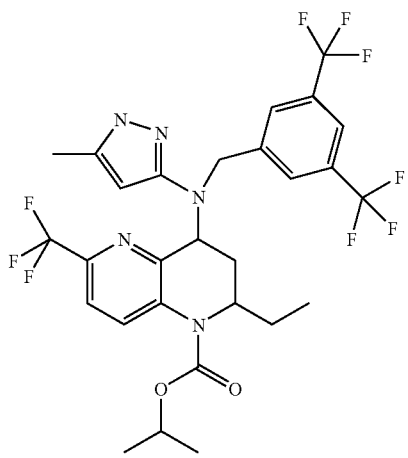

Add slowly cold (ice bath) absolute EtOH (1.7 mL) to a cooled 0° C. stirred mixture of (+/−)-cis-4-[(3,5-bis-trifluoromethyl-benzyl)-(3-oxo-butyryl)-amino]-2-ethyl-6-trifluoromethyl-3,4-dihydro-2H-[1,5]naphthyridine-1-carboxylic acid isopropyl ester (221 mg, 0.34 mmol) and phosphorus pentoxide (880 mg, 6.2 mmol). Add hydrazine hydrate (0.105 mL, 3.4 mmol) while keeping the mixture cooled at 0° C. Seal the tube and heat the reaction mixture at 100° C. overnight. Cool down the mixture and remove the solvents under reduced pressure. Partition the residue between water and dichloromethane. Separate the layers and dry the organic phase, filter, and concentrate in vacuo. Purify the residue by silica gel flash chromatography, eluting with hexanes/ethyl acetate, to afford the title compound (82 mg, 38%). MS (ES+): 638 (M+H).

Example 42

(+/−)-cis-4-[(3,5-Bis-trifluoromethylbenzyl)-(3-methyl-isoxazol-5-yl)-amino]-2-ethyl-6-trifluoromethyl-3,4-dihydro-2H-[1,5]naphthyridine-1-carboxylic acid isopropyl ester

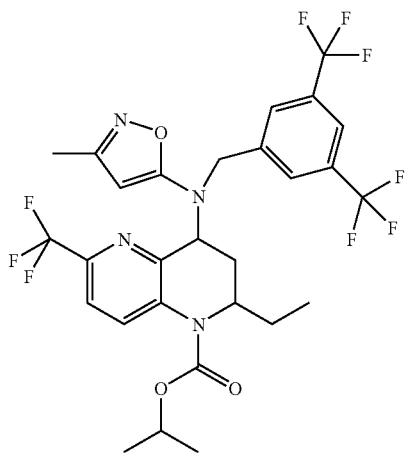

To a solution of (+/−)-cis-4-[(3,5-bis-trifluoromethyl-benzyl)-(3-oxo-butyryl)-amino]-2-ethyl-6-trifluoromethyl-3,4-dihydro-2H-[1,5]naphthyridine-1-carboxylic acid isopropyl ester (225 mg, 0.35 mmol) in MeOH (1.7 mL) at 0° C., add hydroxylamine hydrochloride (37 mg, 0.53 mmol) and sodium acetate (1.4 mg, 0.017 mmol). Stir the reaction mixture under reflux overnight. Cool the mixture and remove the solvents under reduced pressure. Dilute the residue with ethyl acetate and brine. Separate the layers, and dry the organic phase over magnesium sulfate, filter, and concentrate in vacuo. Purify the residue by flash chromatography, eluting with hexanes/ethyl acetate, to afford the title compound (12 mg, 5%). MS (ES+): 639 (M+H).

Example 43

(+/−)-cis-4-[(3,5-Bis-trifluoromethyl-benzyl)-(5-methyl-[1,2,4]oxadiazol-3-yl)-amino]-2-ethyl-6-trifluoromethyl-3,4-dihydro-2H-[1,5]naphthyridine-1-carboxylic acid isopropyl ester

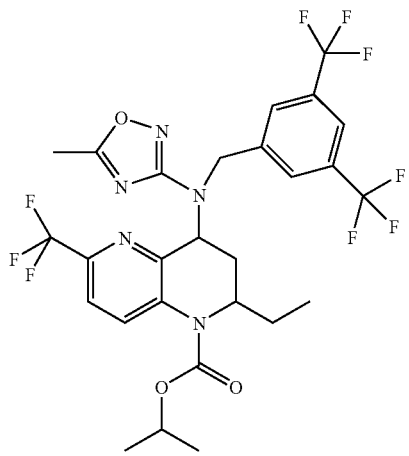

Step 1. Preparation of (+/−)-cis-4-[N-(3,5-Bis-trifluoromethyl-benzyl)-hydroxyguanidino]-2-ethyl-6-trifluoromethyl-3,4-dihydro-2H-[1,5]naphthyridine-1-carboxylic acid isopropyl ester

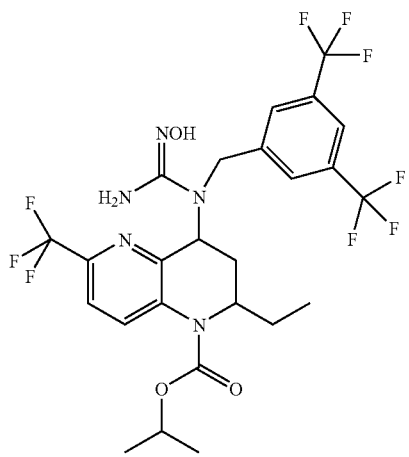

To a solution of 4-[(3,5-bis-trifluoromethyl-benzyl)-cyano-amino]-2-ethyl-6-trifluoromethyl-3,4-dihydro-2H-[1,5]naphthyridine-1-carboxylic acid isopropyl ester (from Example 9) (250 mg, 0.429 mmol) in EtOH (2.6 mL), add hydroxylamine hydrochloride (75 mg, 1.07 mmol) and triethylamine (0.150 mL, 1.07 mmol) at room temperature. Stir the reaction mixture at 80° C. overnight. Cool the mixture and remove the solvents under reduced pressure. Dilute the residue with ethyl acetate and add brine. Separate the layers, dry the organic phase over magnesium sulfate, filter, and concentrate in vacuo. Purify the residue by flash chromatography, eluting with hexanes/ethyl acetate, to afford the title compound (84 mg, 32%). MS (ES+): 616 (M+H).

Step 2. Preparation of (+/−)-cis-4-[(3,5-Bis-trifluoromethyl-benzyl)-(5-methyl-[1,2,4]oxadiazol-3-yl)-amino]-2-ethyl-6-trifluoromethyl-3,4-dihydro-2H-[1,5]naphthyridine-1-carboxylic acid isopropyl ester

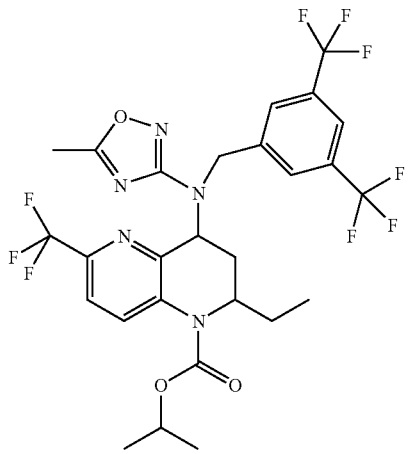

To (+/−)-cis-4-[N-(3,5-bis-trifluoromethyl-benzyl)-hydroxyguanidino]-2-ethyl-6-trifluoromethyl-3,4-dihydro-2H-[1,5]naphthyridine-1-carboxylic acid isopropyl ester (80 mg, 0.13 mmol), add acetic anhydride (0.5 mL). Seal the tube and heat the reaction mixture at 80° C. overnight. Cool down the mixture and remove the solvents under reduced pressure. Add 2 N NaOH (2 mL) and ether to the crude material. Separate the layers, and extract the aqueous phase with ether. Dry the combined organic phase, filter, and concentrate in vacuo. Purify the residue by flash chromatography, eluting with hexanes/ethyl acetate, to afford the title compound (32 mg, %). MS (ES+): 640 (M+H).

Example 44

(+/−)-cis-4-[(3,5-Bis-trifluoromethyl-benzyl)-(2,5-dimethyl-2H-pyrazole-3-carbonyl)-amino]-2-ethyl-6-trifluoromethyl-3,4-dihydro-2H-quinoline-1-carboxylic acid isopropyl ester

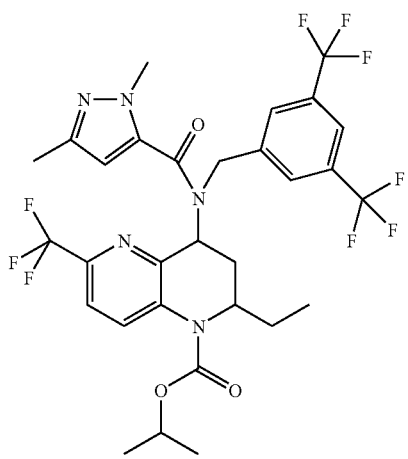

Add a solution of 1,3-dimethyl-1H-pyrazole-5-carbonyl chloride (50 mg, 0.31 mmol) in dry dichloromethane (0.5 mL) to a solution of 4-(3,5-bis-trifluoromethyl-benzylamino)-2-ethyl-6-trifluoromethyl-3,4-dihydro-2H-[1,5]naphthyridine-1-carboxylic acid isopropyl ester (159 mg, 0.28 mmol) in dry dichloromethane (2 mL) and pyridine (0.045 mL, 0.56 mmol) at 0° C. Stir the mixture at room temperature for 3 h. Add a solution of 1,3-dimethyl-1H-pyrazole-5-carbonyl chloride (57 mg, 0.36 mmol) in dry dichloromethane (0.5 mL) and stir the mixture overnight. Remove the solvents under reduced pressure and purify the residue by silica gel flash chromatography, eluting with hexanes/ethyl acetate, to afford the title compound (106 mg, 56%). MS (ES+): 680 (M+H).

Example 45

(+/−)-cis-4-(3,5-Bis-trifluoromethyl-benzyl)-1-(cyclopentylmethyl-2-ethyl-6-methoxy-1,2,3,4-tetrahydro-[1,5]naphthyridine-4-yl)-acetamide

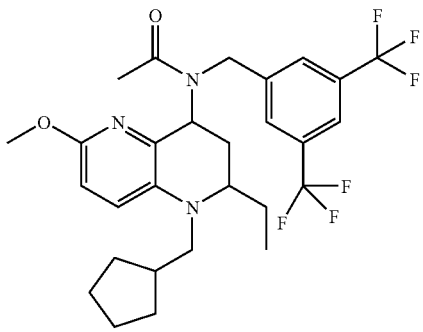

Step 1. Preparation of (+/−)-cis-1-(Cyclopentylmethyl-2-ethyl-6-methoxy-1,2,3,4-tetrahydro-[1,5]naphthyridine-4-yl)-acetamide

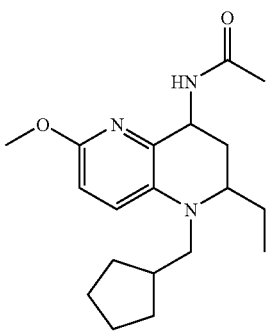

Add sodium triacetoxyborohydride (591 mg, 2.64 mmol) to a mixture of (+/−)-cis-(2-ethyl-6-methoxy-1,2,3,4-tetrahydro-[1,5]naphthyridin-4-yl)acetamide (Example 3, Step 1) (300 mg, 1.20 mmol), cyclopentanecarboxaldehyde (145 mg, 1.44 mmol) and acetic acid (0.086 mL, 1.44 mmol) in dichloroethane (7 mL) under an atmosphere of nitrogen and stir the mixture for 5 h at room temperature. Add a saturated solution of ammonium chloride, separate the layers, and extract the aqueous layer with dichloromethane. Dry the combined organic layers over anhydrous sodium sulfate, filter, and remove the solvent under reduced pressure. Purify the residue using flash chromatography, eluting with hexanes/ethyl acetate, to afford the title compound (281 mg, 71%). MS (ES+): 332 (M+1).

Step 2. Preparation of (+/−)-cis-1-Cyclopentylmethyl-2-ethyl-6-methoxy-1,2,3,4-tetrahydro-[1,5]naphthyridine-4-ylamine

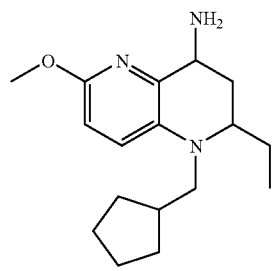

Prepare the title compound by essentially following the procedure described in Example 3, Step 3, by replacing (+/−)-cis-4-acetylamino-2-ethyl-6-methoxy-3,4-dihydro-2H-[1,5]naphthyridine-1-carboxylic acid isopropyl ester with (+/−)-cis-1-(cyclopentylmethyl-2-ethyl-6-methoxy-1,2,3,4-tetrahydro-[1,5]naphthyridine-4-yl)-acetamide. MS (ES+): 273 (M-NH$_2$).

Step 3. Preparation of (+/−)-cis-4-(3,5-bis-trifluoromethyl-benzyl)-1-(cyclopentylmethyl-2-ethyl-6-methoxy-1,2,3,4-tetrahydro-[1,5]naphthyridine-4-yl)-amine

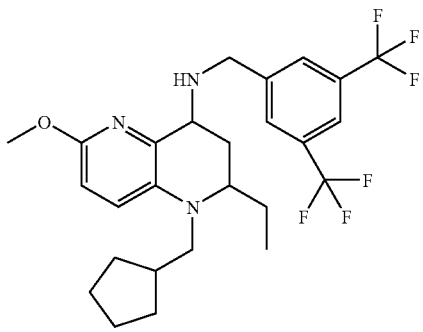

Prepare the title compound by essentially following the procedure described in Example 3, Step 4, by replacing (+/−)-cis-4-amino-2-ethyl-6-methoxy-3,4-dihydro-2H-[1,5]naphthyridine-1-carboxylic acid isopropyl ester with (+/−)-cis-1-cyclopentylmethyl-2-ethyl-6-methoxy-1,2,3,4-tetrahydro-[1,5]naphthyridine-4-ylamine. MS (ES+): 273 (M-NHAr).

Step 4. Preparation of (+/−)-cis-4-(3,5-Bis-trifluoromethyl-benzyl)-1-(cyclopentylmethyl-2-ethyl-6-methoxy-1,2,3,4-tetrahydro-[1,5]naphthyridine-4-yl)-acetamide

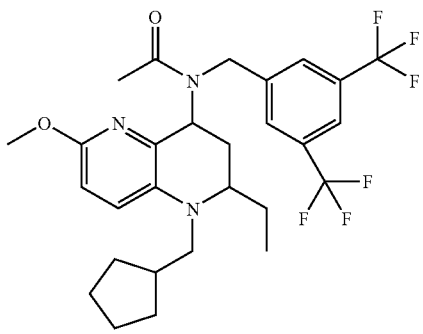

Prepare the title compound by essentially following the procedure described in Example 3, Step 5, by replacing (+/−)-cis-4-(3,5-bis-trifluoromethyl-benzylamino)-2-ethyl-6-methoxy-3,4-dihydro-2H-[1,5]naphthyridine-1-carboxylic acid isopropyl ester with (+/−)-cis-4-(3,5-bis-trifluoromethyl-benzyl)-1-(cyclopentylmethyl-2-ethyl-6-methoxy-1,2,3,4-tetrahydro-[1,5]naphthyridine-4-yl)-amine. MS (ES+): 558 (M+H).

Example 46

(+/−)-cis-4-[Acetyl-(3,5-bis-trifluoromethyl-benzyl)-amino]-6-methoxy-2-methyl-3,4-dihydro-2H-[1,5]naphthyridine-1-carboxylic acid isopropyl ester

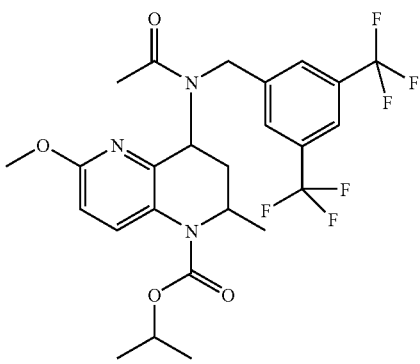

Step 1. Preparation of (+/−)-cis-N-(6-Methoxy-2-methyl-1,2,3,4-tetrahydro-[1,5]naphthyridin-4-yl)acetamide.

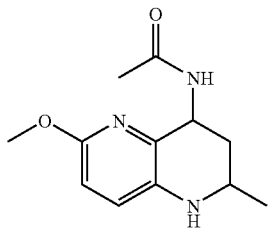

Dissolve 6-methoxy-pyridin-3-ylamine (1.24 g, 10.05 mmol) in anhydrous dichloromethane (20 mL), add sodium sulfate (1.0 g) and cool the reaction mixture to −20° C. Add acetaldehyde (0.560 mL, 10.05 mmol) and stir the mixture from −20 to 0° C. for 0.5 h. Filter off the sodium sulfate and add N-vinyl acetamide (0.851 g, 10.05 mmol) to the filtrate at −20° C. followed by boron trifluoride diethyl etherate (0.126 mL, 1.0 mmol). Stir the reaction mixture from −20 to −10° C. for 6 h. Remove the solvent under reduced pressure and purify using silica gel column chromatography (gradient eluent, 0-5% MeOH in ethyl acetate) to provide the title compound (1.09 g, 47%). MS (ES+): 236 (M+H).

Step 2. Preparation of (+/−)-cis-4-Acetylamino-6-methoxy-2-methyl-3,4-dihydro-2H-[1,5]naphthyridine-1-carboxylic acid isopropyl ester

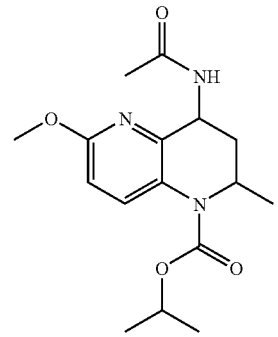

Add isopropyl chloroformate (8.50 mL, 8.50 mmol) to a solution of (+/−)-cis-N-(6-methoxy-2-methyl-1,2,3,4-tetrahydro-[1,5]naphthyridin-4-yl)acetamide (0.404 g, 1.702 mmol), pyridine (1.370 mL, 17.02 mmol) in dichloromethane (10 mL) at 0° C. and slowly warm to room temperature. After 12 h, remove the solvent under reduced pressure. Purify the crude material using silica gel chromatography, eluting with ethyl acetate (neat), to afford the title compound (0.496 g, 91%). MS (ES+): 322 (M+H).

Step 3. Preparation of (+/−)-cis-4-Amino-6-methoxy-2-methyl-3,4-dihydro-2H-[1,5]naphthyridine-1-carboxylic acid isopropyl ester

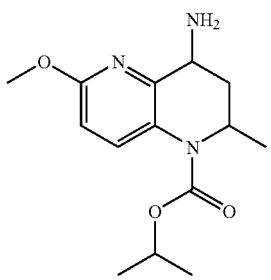

Heat at 80° C. a solution of (+/−)-cis-4-acetylamino-6-methoxy-2-methyl -3,4-dihydro-2H-[1,5]naphthyridine-1-carboxylic acid isopropyl ester (405 mg, 1.261 mmol) in 5 N HCl (3 mL) for 3 h. Cool the reaction mixture to room temperature, pour into a saturated solution of sodium carbonate, and extract with dichloromethane. Dry the organic layer over anhydrous sodium sulfate, filter, and remove the solvent under reduced pressure, to afford the title compound (0.315 g, 89%). MS (ES+): 280 (M+H).

Step 4. Preparation of (+/−)-cis-4-(3,5-Bis-trifluoromethyl-benzylamino)-6-methoxy-2-methyl-3,4-dihydro-2H-[1,5]naphthyridine-1-carboxylic acid isopropyl ester

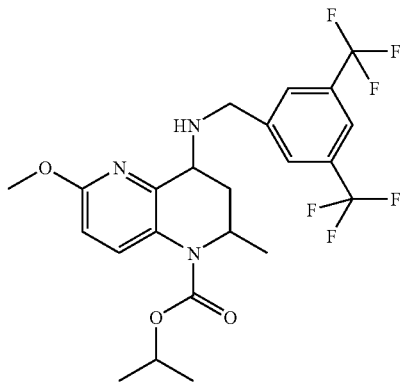

Add sodium triacetoxyborohydride (1.160 g, 5.50 mmol) to a mixture of 3,5-bis(trifluoromethyl)benzaldehyde (0.217 mL, 1.32 mmol), acetic acid (0.010 mL, 1.65 mmol), and (+/−)-cis-4-amino-6-methoxy-2-methyl-3,4-dihydro-2H-[1,5]naphthyridine-1-carboxylic acid isopropyl ester (0.318 mg, 1.12 mmol) in dichloroethane (10 mL). Stir thie mixture at room temperature under an atmosphere of nitrogen for 14 h. Add a saturated solution of sodium bicarbonate, separate the layers, and extract the aqueous layer with dichioromethane. Dry the combined organic layers over anhydrous sodium sulfate, filter, and remove the solvent under reduced pressure. Purify the residue by flash chromatography, eluting with hexanes/ethyl acetate (gradient eluent, 0-60% ethyl acetate in hexane), to afford the title compound (0.462 g, 83%). MS (ES+): 506 (M+H).

Step 5. Preparation of (+/−)-cis-4-[Acetyl-(3,5-bis-trifluoromethyl-benzyl)-amino]-6-methoxy-2-methyl-3,4-dihydro-2H-[1,5]naphthyridine-1-carboxylic acid isopropyl ester

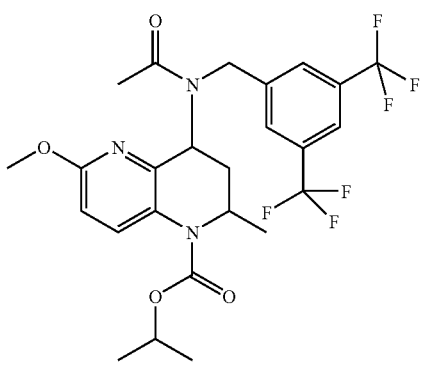

Cool to 0° C. a suspension of (+/−)-cis-4-(3,5-bis-trifluoromethyl-benzylamino)-6-methoxy-2-methyl-3,4-dihydro-2H-[1,5]naphthyridine-1-carboxylic acid isopropyl ester (0.210 g, 0.415 mmol) and pyridine (0.203 mL, 2.52 mmol) in dichloromethane (3 mL) under nitrogen. Add acetic anhydride (0.117 mL, 1. 247 mmol) dropwise. After the addition is complete, remove the cooling bath and warm the reaction to room temperature with stirring for 12 h. Dilute the mixture with dichloromethane (25 mL) and wash with saturated aqueous sodium bicarbonate (25 mL). Dry the organic layer over sodium sulfate, filter, and remove the solvent under reduced pressure. Purify the residue using silica gel chromatography, eluting with hexanes/ethyl acetate (gradient eluent, 0-30% ethyl acetate in hexane), to afford the title compound (0.196 g, 88%). MS (ES+): 548 (M+H).

Example 47

(+/−)-cis-4-[(3,5-Bis-trifluoromethyl-benzyl)-ethoxycarbonyl-amino]-6-methoxy-2-methyl-3,4-dihydro-2H-[1,5]naphthyridine-1-carboxylic acid isopropyl ester

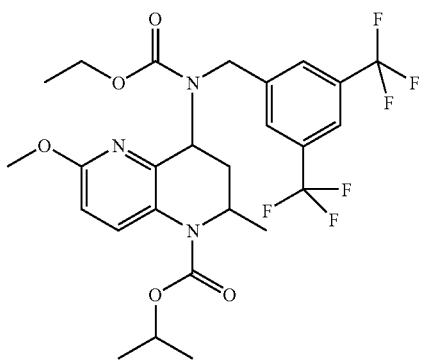

Add ethyl chloroformate (0.118 mL, 1.240 mmol), followed by pyridine (0.205 mL, 2.52 mmol), to a solution of (+/−)-cis-4-(3,5-bis-trifluoromethyl-benzylamino)-6-methoxy-2-methyl-3,4-dihydro-2H-[1,5]naphthyridine-1-carboxylic acid isopropyl ester (0.210 g, 0.415 mmol) in dichloromeihane (3 mL). After stirring at room temperature for 12 h remove the solvent in vacuo. Purify using silica gel chromatography, eluting with ethyl acetate/hexane (gradient eluent, 0-30% ethyl acetate in hexane) to afford the title compound (0.218 g, 92%): MS (ES+): 578 (M+H).

Example 48

(+/−)-cis-4-[(3,5-Bis-trifluoromethyl-benzyl)-(3-fluoro-5-trifluoromethyl-benzoyl)-amino]-6-methoxy-2-methyl-3,4-dihydro-2H-[1,5]naphthyridine-1-carboxylic acid isopropyl ester

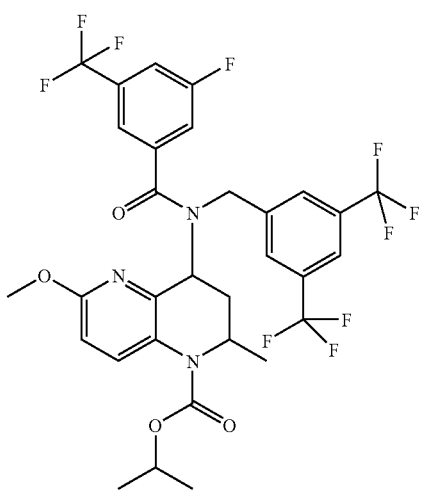

Prepare the title compound by essentially following the procedure described for the synthesis of Example 47, using (+/−)-cis-4-(3,5-bis-trifluoromethyl-benzylamino)-6-methoxy-2-methyl-3,4-dihydro-2H-[1,5]naphthyridine-1-carboxylic acid isopropyl ester (0.210 g, 0.415 mmol), 3-fluoro-5-trifluoromethyl benzoyl chloride (0.095 mL, 0.631 mmol) and pyridine (0.10 mL). Purify using silica gel column chromatography (gradient eluent, 0-30% ethyl acetate in hexane) to provide the title compound (0.246 g, 88%). MS (ES+): 696 (M+H).

Example 49

(+/−)-cis-N-(3,5-Bis-trifluoromethyl-benzyl)-N-(1-cyclopentyl-6-methoxy-2-methyl-1,2,3,4-tetrahydro-[1,5]napthyridin-4-yl)-acetamide

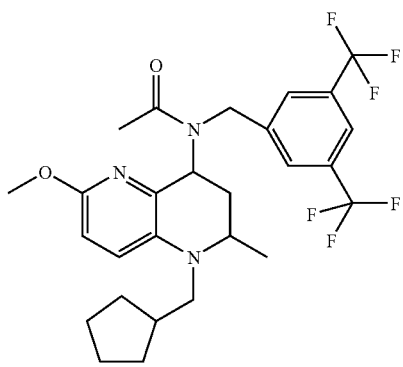

Step 1. Preparation of (+/−)-cis-N-(1-Cyclopentyl-6-methoxy-2-methyl-1,2,3,4-tetrahydro-[1,5]napthyridin-4-yl)-acetamide

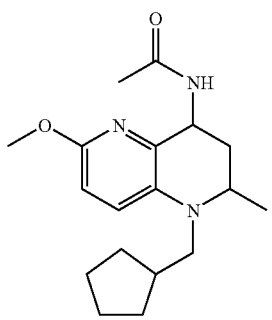

Prepare the title compound by essentially following the procedure described in Example 45, Step 1, using, (+/−)-cis-N-(6-methoxy-2-methyl-1,2,3,4-tetrahydro-[1,5]naphthyridin-4-yl)acetamide (0.410 g, 1.745 mmol), cyclopentane carboxaldehyde (0.833 mL, 8.51 mmol) and sodium triacetoxyborohydride (1.8 g, 8.5 mmol). Purify using silica gel column chromatography (gradient eluent, 0-100% ethyl acetate in hexane) to provide the title compound (0.532 g, 98%). MS (ES+): 318 (M+H).

Step 2. Preparation of (+/−)-N-(3,5-Bis-trifluoromethyl-benzyl)-N-(1-cyclopentyl-6-methoxy-2-methyl-1,2,3,4-tetrahydro-[1,5]napthyridin-4-yl)-acetamide

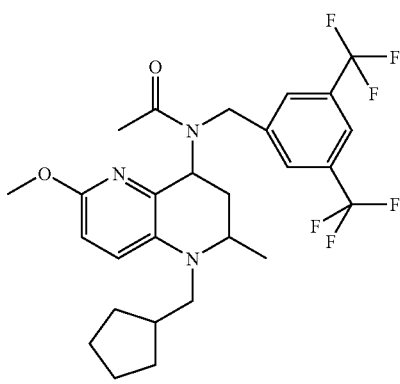

Add lithium hexamethyldisilazide (0.220 mL, 0.220 mmol, 1.0 M in toluene) to a solution of (+/−)-N-(1-cyclopently-6-methoxy-2-methyl-1,2,3,4-tetrahydro-[1,5]napthyridin-4-yl)-acetamide (0.065 g, 0.20 mmol) in THF (1 mL) at −78° C. and stir for 20 min. Treat the dark solution with a solution of 3,5-bis trifluoromethyl benzylbromide (0.240 mmol, 0.040 mL) in THF (1 mL). Stir the reaction mixture vigorously at −78° C. for 1 h and slowly warm to room temperature over 12 h. Dilute the reaction mixture with EtOAc (10 mL), and wash with water and brine. Separate the organic phase, dry over Na₂SO₄, filter, and concentrate iii vacuo. Purify by flash column chromatography (gradient eluent, 0-50% ethyl acetate in hexane) to provide the title compound (0.026 g, 27%). MS (ES+): 544 (M+H).

Example 50

Synthesis of (+/−)-cis-4-[Acetyl-(3,5-bis-trifluoromethyl-benzyl)-amino]-2-methyl-6-trifluoromethyl-3,4-dihydro-2H-[1,5]naphthyridine-1-carboxylic acid isopropyl ester

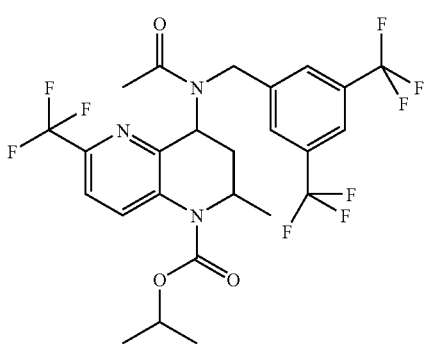

Step 1. Preparation of (+/−)-cis-N-(2-Methyl-6-trifluoromethyl-1,2,3,4-tetrahydro-[1,5]naphthyridin-4-yl)acetamide

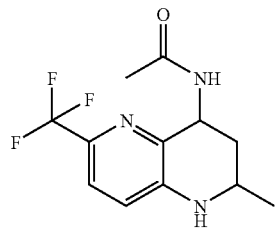

Prepare the title compound by essentially following the procedure described in Example 46, Step 1, using 6-trifluoromethyl-pyridin-3-ylamine (1.0 g, 6.168 mmol), acetaldehyde (0.380 mL, 6.780 mmol) and N-vinyl acetamide (0.520 g, 6.12 mmol). Purify using silica gel column chromatography (gradient eluent, 0-10% MeOH in ethyl acetate) to provide the title compound (0.69 g, 43%). MS (ES+): 274 (M+H).

Step 2. Preparation of (+/−)-cis-4-Acetylamino-2-methyl-6-trifluoromethyl-3,4-dihydro-2H-[1,5]naphthyridine-1-carboxylic acid isopropyl ester

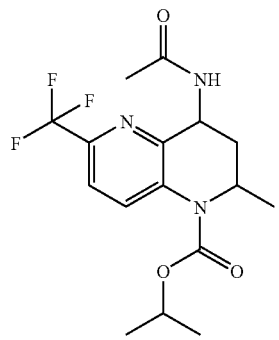

Prepare the title compound by essentially following the procedure described in Example 46, Step 2, by replacing (+/−)-cis-N-(6-methoxy-2-methyl-1,2,3,4-tetrahydro-[1,5]naphthyridin-4-yl)acetamide, with (+/−)-cis-N-(2-methyl-6-trifluoromethyl-1,2,3,4-tetrahydro-[1,5]naphthyridin-4-yl) acetamide (0.140.g, 0.512 mmol), and using isopropyl chloroformate, pyridine, and dimethylaminopyridine. Purify using silica gel column chromatography (gradient eluent, 0-5% MeOH in ethyl acetate) to provide the title compound (0.123 g, 68%). MS (ES+): 360 (M+H).

Step 3. Preparation of (+/−)-cis-4-[Acetyl-(3,5-bis-trifluoromethyl-benzyl)-amino]-2-methyl-6-trifluoromethyl-3,4-dihydro-2H-[1,5]naphthyridine-1-carboxylic acid isopropyl ester

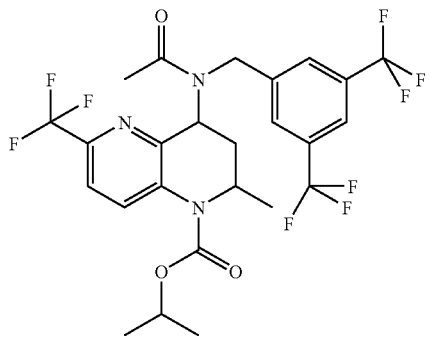

Prepare the title compound by essentially following the procedure described in Example 49, Step 2, by replacing (+/−)-N-(1-cyclopently-6-methoxy-2-methyl-1,2,3,4-tetrahydro-[1,5]napthyridin-4-yl)-acetamide with cis-4-acetylamino-2-methyl-6-trifluoromethyl-3,4-dihydro-2H-[1,5] naphthyridine-1-carboxylic acid isopropyl ester (0.065 g, 0.018 mmol), and using 3,5-bis trifluoromethyl benzylbromide and lithium hexamethyldisilazide. Purify using silica gel column chromatography (gradient eluent, neat ethyl acetate) to afford the title compound (0.031 g, 30%). MS (ES+): 586 (M+H).

Example 51

(+/−)-cis-4-[Acetyl-(3,5-bis-trifluoromethyl-benzyl)-amino]-2-cyclopropyl-6-trifluoromethyl-3,4-dihydro-2H-[1,5]naphthyridine-1-carboxylic acid isopropyl ester

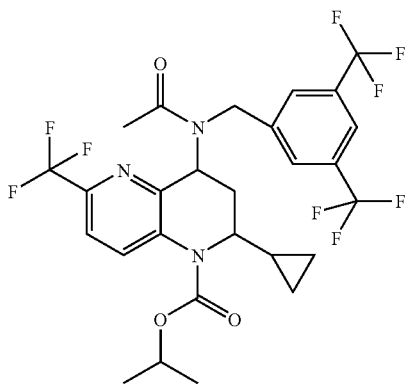

Step 1. Preparation of (+/−)-cis-N-(2-Cyclopropyl-6-trifluoromethyl-1,2,3,4-tetrahydro-[1,5]naphthyridin-4-yl)acetamide

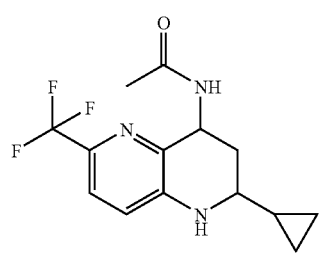

Prepare the title compound by essentially following the procedure described in Example 46, Step 1, using, 6-trifluoromethyl-pyridin-3-ylamine (1.0 g, 6.168 mmol), cyclopropanaldehyde (0.460 mL, 6.160 mmol) and N-vinyl acetamide (0.520 g, 6.12 inmol). Purification by silica gel column (gradient eluent, 0-5% MeOH in ethyl acetate) provides the title compound (0.62 g, 29%). MS (ES+): 300 (M+H).

Step 2. Preparation of (+/−)-cis-4-Acetylamino-2-cyclopropyl-6-trifluoromethyl-3,4-dihydro-2H-[1,5] naphthyridine-1-carboxylic acid isopropyl ester

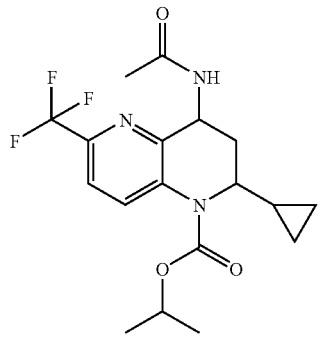

Prepare the title compound by essentially following the procedure described in Example 46, Step 2, by replacing (+/−)-cis-N-(6-methoxy-2-methyl-1,2,3,4-tetrahydro-[1,5]naphthyridin-4-yl)acetamide, with (+/−)-cis-N-(2-cyclopropyl-6-trifluoromethyl-1,2,3,4-tetrahydro-[1,5]naphthyridin-4-yl)acetamide (1.05 g, 3.512 mmol), and using isopropyl chloroformate, pyridine, and dimethylaminopyridine. Purify using silica gel column chromatography (gradient eluent, 0-5% MeOH in ethyl acetate) to provide the title compound (0.416 g, 31%). MS (ES+): 386 (M+H).

Step 3. Preparation of (+/−)-cis-4-[Acetyl-(3,5-bis-trifluoromethyl-benzyl)-amino]-2-cyclopropyl-6-trifluoromethyl-3,4-dihydro-2H-[1,5]naphthyridine-1-carboxylic acid isopropyl ester

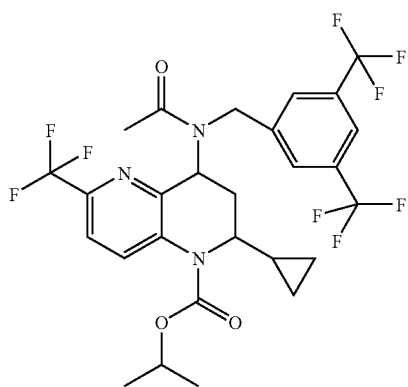

Prepare the title compound by essentially following the procedure described in Example 49, Step 2, by replacing (+/−)-N-(1-cyclopently-6-methoxy-2-methyl-1,2,3,4-tetrahydro-[1,5]napthyridin-4-yl)-acetamide, with (+/−)-cis-4-acetylamino-2-cyclopropyl-6-trifluoromethyl-3,4-dihydro-2H-[1,5]naphthyridine-1-carboxylic acid isopropyl ester (0.075 g, 0.019 mmol), and using 3,5-bis trifluoromethyl benzyl bromide and lithium hexamethyldisilazide. Purify by silica gel column chromatography (gradient eluent, neat ethyl acetate) to afford the title compound (0.042 g, 35%). MS (ES+): 612 (M+H).

Example 52

(+/−)-cis-4-[(3,5-Bis-trifluoromethyl-benzyl)-(2methyl-2H-tetrazole-5-yl)-amino]-2-cyclopropyl-6-trifluoromethyl-3,4-dihydro-2H-[1,5]naphthyridine-1-carboxylic acid isopropyl ester

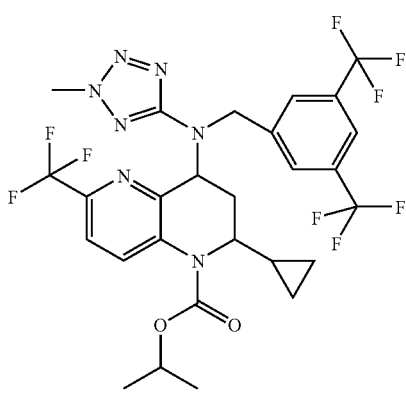

Step 1. Preparation of (+/−)-cis-4-Amino-2-cyclopropyl-6-trifluoromethyl-3,4-dihydro-2H-[1,5]naphthyridine-1-carboxylic acid isopropyl ester

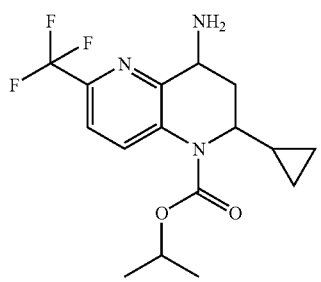

Heat at 80° C. a solution of (+/−)-cis-4-acetylamino-2-cyclopropyl-6-trifluoromethyl-3,4-dihydro-2H-[1,5]naphthyridine-1-carboxylic acid isopropyl ester (0.281 g, 0.727 mmol) in 5 N HCl (3 mL) for 3 h. Cool the reaction mixture to room temperature, pour the crude onto a saturated solution of sodium carbonate and extract with dichloromethane. Dry the organic layer over anhydrous sodium sulfate, filter, and remove the solvent under reduced pressure, to afford the title compound (0.251 g, 99%). MS (ES+): 344 (M+H).

Step 2. Preparation of (+/−)-cis-4-(3,5-Bis-trifluoromethyl-benzylamino)-2-cyclopropyl-6-trifluoromethyl-3,4-dihydro-2H-[1,5]naphthyridine-1-carboxylic acid isopropyl ester and cis-4-(3,5-Bis-trifluoromethyl-benzyl)-ethyl-amino)-2-cyclopropyl-6-trifluoromethyl-3,4-dihydro-2H-[1,5]naphthyridine-1-carboxylic acid isopropyl ester

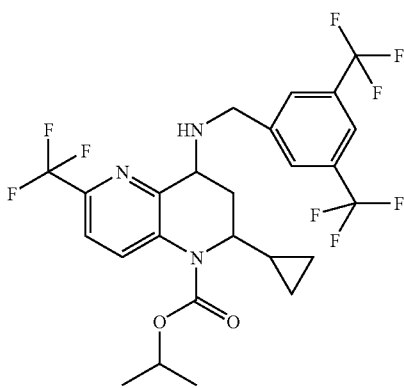

Prepare the title compound by essentially following the procedure described in Example 46, Step 4, by replacing (+/−)-cis-4-amino-6-methoxy-2-methyl-3,4-dihydro-2H-[1,5]naphthyridine-1-carboxylic acid isopropyl ester, with (+/−)-cis-4-amino-2-cyclopropyl-6-trifluoromethyl-3,4-dihydro-2H-[1,5]naphthyridine-1-carboxylic acid isopropyl ester (0.252 g, 0.732 mmol), and using bis-3,5-trifluoromethyl benzaldehyde (0.145 mL, 0.861 mmol) and sodium triacetoxyborohydride (0.8 g). Purify using silica gel column chromatography (gradient eluent, 0-50% ethyl acetate in hexane) to provide the title compound (0.182 g, 45%). MS (ES+): 570 (M+H) as major compound. Also isolate a minor compound, (+/−)-cis-4-(3,5-bis-trifluoromethyl-benzyl)-ethyl-amino)-2-cyclopropyl-6-trifluoromethyl-3,4-dihydro-2H-[1,5]naphthyridine-1-carboxylic acid isopropyl ester (0.14 g, 23%). MS (ES+): 598 (M+H).

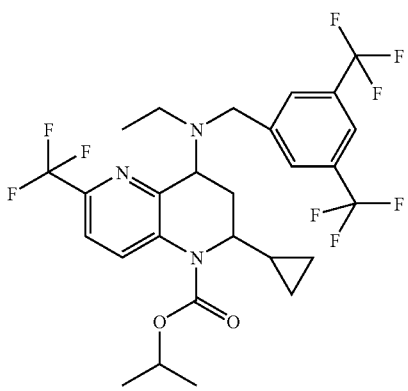

Step 3. Preparation of (+/−)-cis-4-(3,5-Bis-trifluoromethyl-benzyl)-cyano-amino)-2-cyclopropyl-6-trifluoromethyl-3,4-dihydro-2H-[1,5]naphthyridine-1-carboxylic acid isopropyl ester

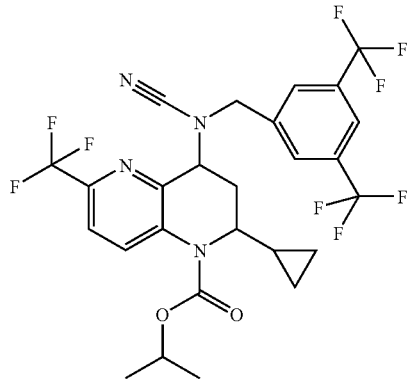

Add cyanogen bromide (0.041 g, 0.377 mmol) followed by N,N-diisopropylethylamine (0.083 mL, 0.492 mmol) to a solution of (+/−)-cis-4-(3,5-bis-trifluoromethyl-benzylamino)-2-cyclopropyl-6-trifluoromethyl-3,4-dihydro-2H-[1,5]naphthyridine-1-carboxylic acid isopropyl ester (0.071 g, 0.123 mmol) in THF (2 mL). After stirring at 65° C. for 12 h, remove the solvent under vacuum. Dilute with ether (20 mL), wash with water, brine, dry over sodium sulfate, filter, and concentrate under reduced pressure. Chromatograph the product over silica gel, eluting with ethyl acetate/hexane (gradient eluent, 0-50% ethyl acetate in hexane) to afford the title compound (0.031 g, 43%). MS (ES+): 595 (M+H).

Step 4. Preparation of (+/−)-cis-4-[(3,5-Bis-trifluoromethyl-benzyl)-(2H-tetrazole-5-yl)-amino]-2-cyclopropyl-6-trifluoromethyl-3,4-dihydro-2H-[1,5]naphthyridine carboxylic acid isopropyl ester

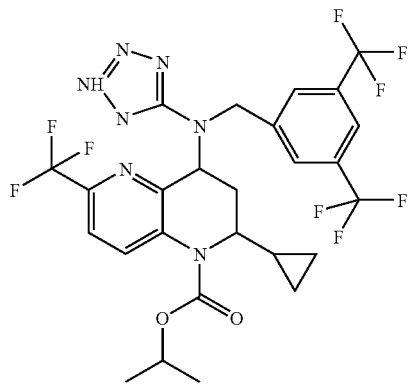

Combine cis-4-(3,5-bis-trifluoromethyl-benzyl)-cyano-amino)-2-cyclopropyl-6-trifluoromethyl-3,4-dihydro-2H-[1,5]naphthyridine-1-carboxylic acid isopropyl ester (0.022 g, 0.037 mmol) with sodium azide (1-5 eq) and triethylamine hydrochloride (0.015 g, 0.12 mmol) in anhydrous toluene (2 mL) and heat at 110° C. with stirring for 20 h. Dilute the cooled mixture with water and 0.1 N HCl and extract with EtOAc. Combine the organic layers and wash with water and brine, dry over sodium sulfate, filter, and concentrate under reduced pressure to give a residue. Purify using silica gel column chromatography (gradient eluent, 0-50% ethyl acetate in hexane) to provide the title compound (0.021 g, 81%). MS (ES+): 638 (M+H).

Step 5. Preparation of (+/−)-cis-4-[(3,5-Bis-trifluoromethyl-benzyl)-(2-methyl-2H-tetrazole-5-yl)-amino]-2-cyclopropyl-6-methoxy-3,4-dihydro-2H-[1,5]naphthyridine-1-carboxylic acid isopropyl ester

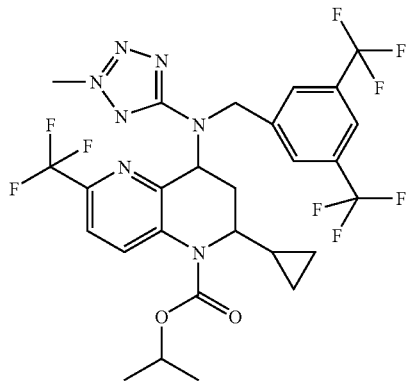

To a solution of (+/−)-cis-4-[(3,5-bis-trifluoromethyl-benzyl)-(2H-tetrazole-5-yl)-amino]-2-cyclopropyl-6-trifluoromethyl-3,4-dihydro-2H-[1,5]naphthyridine-1-carboxylic acid isopropyl ester (0.020 g, 0.032 mmol) and methanol (0.012 mL, 0.30 mmol) in dichloromethane (1 mL) at room temperature, under nitrogen atmosphere, add triphenyl phosphine (5.2 mg, 0.032 mmol) in one portion followed by addition of diethyl azodicarboxylate (DEAD) (0.010 mL, 0.032 mmol). Allow the reaction mixture to stir at room temperature overnight. Add more methanol (0.015 mL, 0.36 mmol), triphenyl phosphine (5.2 mg, 0.032 mmol) and DEAD (0.010 mL, 0.032 mmol). After stirring for 6 h, remove the solvents under reduced pressure. Purify the residue by flash chromatography, eluting with hexanes/ethyl acetate, to afford the title compound (11.2 mg, 57%): MS (ES+): 652 (M+H).

Example 53

4-[(3,5-Bis-trifluoromethyl-benzyl)-(5,6,7,8-tetrahydro-quinolin-3-yl)-amino]-2,3-dimethyl-3,4,6,7,8,9-hexahydro-2H-benzo[b][1,5]napthyridine-1-carboxylic acid isopropyl ester

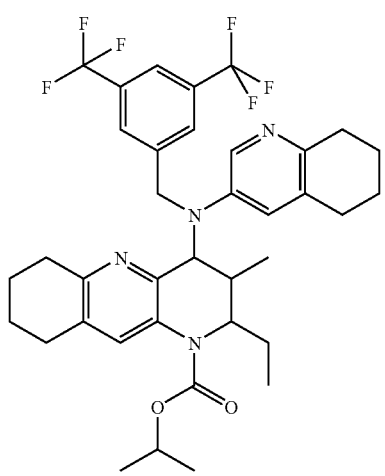

Step 1. Preparation of (2-Ethyl-3-methyl-1,2,3,4,6,7,8,9-octahydro-benzo[b][1,5] napthyridin-4yl)-(5,6,7,8-tetrahydro-quinolin-3-yl)-amine

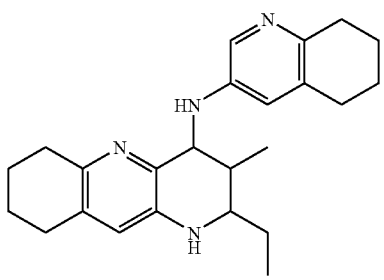

Prepare the title compound by essentially following the procedure described in Example 46, Step 1, using, 5,6,7,8-tetrahydro-quinolin-3-ylamine (4.0 g, 26.84 mmol), propionaldehyde (1.936 mL, 26.84 mmol) and N-vinyl acetamide (2.28 g, 26.84 mmol). Purify using silica gel column chromatography (gradient eluent, 0-5% MeOH in ethyl acetate) to provide the title compound (4.39 g, 59%). MS (ES+): 377 (M+H).

Step 2. Preparation of 2-Ethyl-3-methyl-4-(5,6,7,8-tetrahydro-quinolin-3-ylamino)-3,4,6,7,8,9-hexahydro-2H-benzo[b][1,5]napthyridine-1-carboxylic acid isopropyl ester.

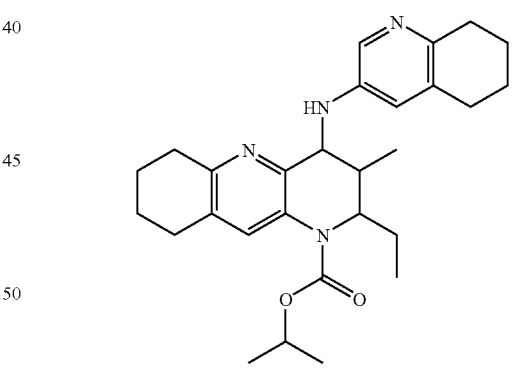

Prepare the title compound by essentially following the procedure described in Example 46, Step 2, by replacing (+/−)-cis-N-(6-methoxy-2-methyl-1,2,3,4-tetrahydro-[1,5]naphthyridin-4-yl)acetamide, with (2-ethyl-3-methyl-1,2,3,4,6,7,8,9-octahydro benzo [b][1,5]napthyridin-4yl)-(5,6,7,8-tetrahydro-quinolin-3-yl)-amine (0.575 g, 1.52 mmol), and using isopropyl chloroformate, pyridine, and dimethylaminopyridine. Purify using silica gel column chromatography (gradient eluent, neat ethyl acetate) to provide the title compound (0.218 g, 31%). MS (ES+): 463 (M+H).

Step 3. Preparation of 4-[(3,5-Bis-trifluoromethyl-benzyl)-(5,6,7,8-tetrahydro-quinolin-3-yl)-amino]-2,3-dimethyl-3,4,6,7,8,9-hexahydro-2H-benzo[b][1,5]napthyridine-1-carboxylic acid isopropyl ester

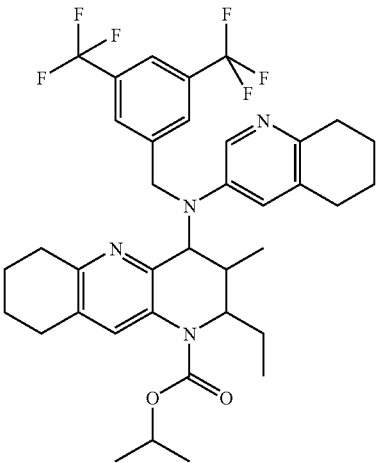

Prepare the title compound by essentially following the procedure described in Example 49, Step 2, by replacing (+/−)-N-(1-cyclopentyl-6-methoxy-2-methyl-1,2,3,4-tetrahydro-[1,5]napthyridin-4-yl)-acetamide, with 2-ethyl-3-methyl-4-(5,6,7,8-tetrahydro-quinolin-3-ylamino)-3,4,6,7,8,9-hexahydro-2H-benzo[b][1,5]napthyridine-1-carboxylic acid isopropyl ester (0.175 g, 0.378 mmol), and using 3,5-bis trifluoromethyl benzyl bromide and lithium hexamethyldisilazide. Purify using silica gel column chromatography (gradient eluent, 50:50 ethyl acetate in hexane) to afford the title compound (0.052 g, 20%). MS (ES+): 689 (M+H).

We claim:

1. A compound of a formula below:

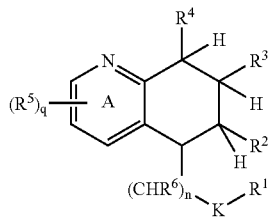

I wherein
q is 0, 1, or 2;
K is a bond or C=O;
n is 0; or 1
when n is 0, K is C=O and $R^1$ is selected from: —$OC_1$—$C_6$ alkyl, —$OC_1$—$C_6$ alkylheterocyclyl, —O-heterocyclyl, —$OC_1$ - $C_6$alkyl$CO_2$ $R^{11}$, —$OC_2$-$C_6$alkylalcohol, —$OC_1$-$C_6$ alkyl$NR^7R^8$, —$OC_2$-$C_6$ alkylcyano, wherein heterocyclic group is optionally substituted with $C_1$-$C_6$ alkyl,
when n is 1, K is a bond and $R^1$ is $C_3$-$C_8$ cycloalkyl,
$R^2$ is $C_1$-$C_6$ alkyl or $C_3$-$C_8$ cycloalkyl;
$R^3$ is hydrogen or $C_1$-$C_6$ alkyl;
$R^4$ is a group represented by the formula —$NR^9R^{10}$;

$R^5$ is selected from: hydrogen, halogen, $C_1$-$C_6$ alkyl, $C_1$-$C_6$alkoxy, $C_1$-$C_6$ haloalkyl, —$NR^7R^8$, or two adjacent $R^5$ groups may combine to form a fused 5 or 6 member carbocyclic ring;

$R^6$ is hydrogen, $R^7$ and $R^8$ are independently selected from hydrogen, C(O)$OC_1$-$C_4$ alkyl, $C_1$-$C_6$ alkyl, and aryl: wherein each aryl group is optionally substituted with halo $C_1$-$C_6$ haloalkyl, $R^9$ is the group tetrazolyl, pyrazolyl, oxazolyl, oxadiazolyl, quinolinyl, $COR^7$, and $CO_2R^7$, and wherein each tetrazole, pyrazolyl, oxazolyl, oxadiazolyl, each is optionally substituted with one to two groups independently selected from $C_1$-$C_6$ alkyl, $C_1$-$C_6$ alkylalcohol, $C_1$—$C_6$ alkylamine, and $C_1$-$C_6$ alkyl$NR^7R^8$;

$R^{10}$ is 3,5-bis-trifluoromethyl benzyl:

$R^{11}$ hydrogen or $C_1$-$C_6$ alkyl: or a pharmaceutically acceptable salt.

2. A compound according to claim 1, or a pharmaceutically acceptable salt thereof, wherein n is zero, K is C=O and $R^1$ is selected from a group consisting of —$OC_1$-$C_6$ alkyl, —O heterocyclyl —$OC_1$-$C_6$ alkyl$CO_2R^{11}$, —$OC_2$-$C_6$ alkylalcohol, —$OC_1C_6$ alkyl$NR^7R^8$, —$OC_2$-$C_6$ alkylcyano and —$OC_1$-$C_6$ alkylheterocyclyl.

3. A compound according to claim 1, or a pharmaceutically acceptable salt, thereof, wherein n is 1, K is a bond and $R^1$ is cycloalkyl.

4. A compound according to claim 1, or a pharmaceutically acceptable salt thereof, wherein $R^9$ is tetrazolyl optionally substituted with one to two groups independently selected from $C_1$-$C_6$ alkyl, $C_1$-$C_6$ alkylalcohol, and $C_1$-$C_6$ alkyalmine.

5. A compound according to claim 1, or a pharmaceutically acceptable salt thereof, wherein each $R^3$ is hydrogen and $R^9$ is selected from: tetrazolyl, pyrazolyl, oxazolyl, oxidiazolyl, quinolinyl, each optionally substituted with one to two groups independently selected from $C_1$-$C_6$ alkyl, $C_1$-$C_6$ alkylalcohol, $C_1$-$C_2$ alkylamine, and $C_1$-$C_2$ alkyl$NR^7R^8$.

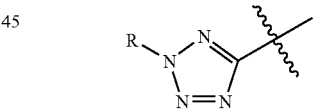 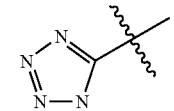

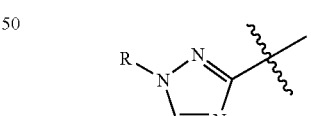 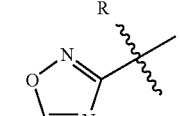

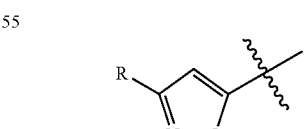 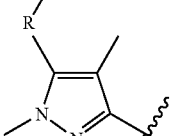

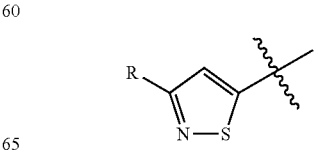 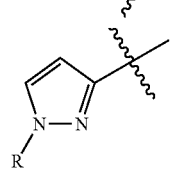

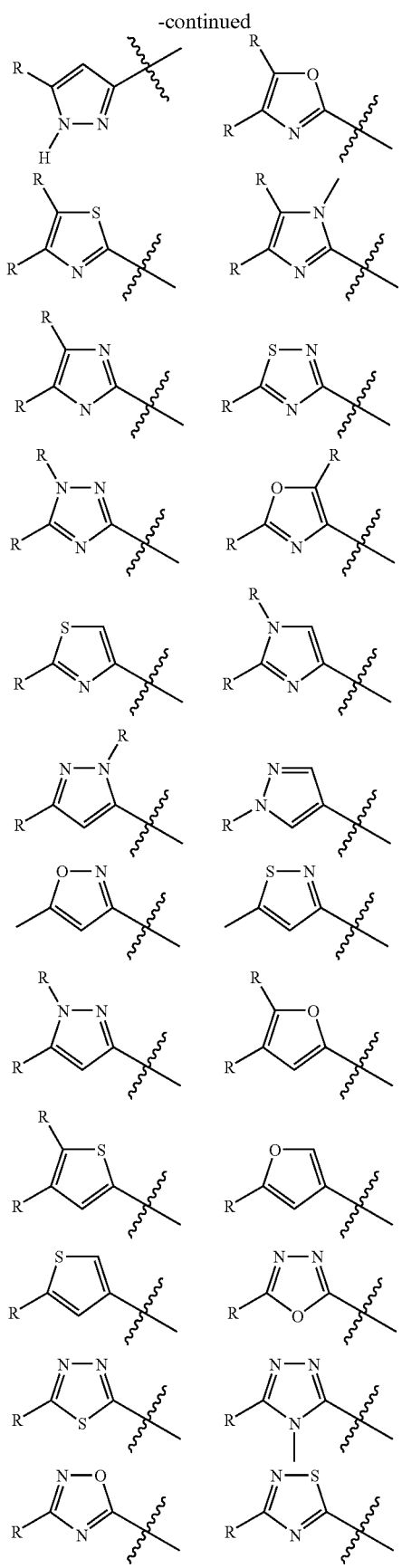
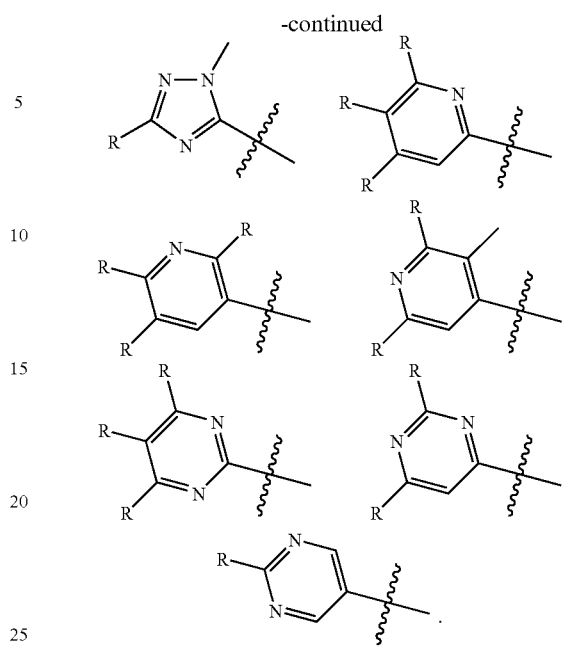
6. A compound according to claim 1, or a pharmaceutically acceptable salt thereof, wherein two $R^5$ groups combine to form a fused cyclopentane or cyclohexane ring with ring A.
7. A compound according to claim 1, or a pharmaceutically acceptable salt thereof, wherein $R^4$ is selected from the group consisting of:
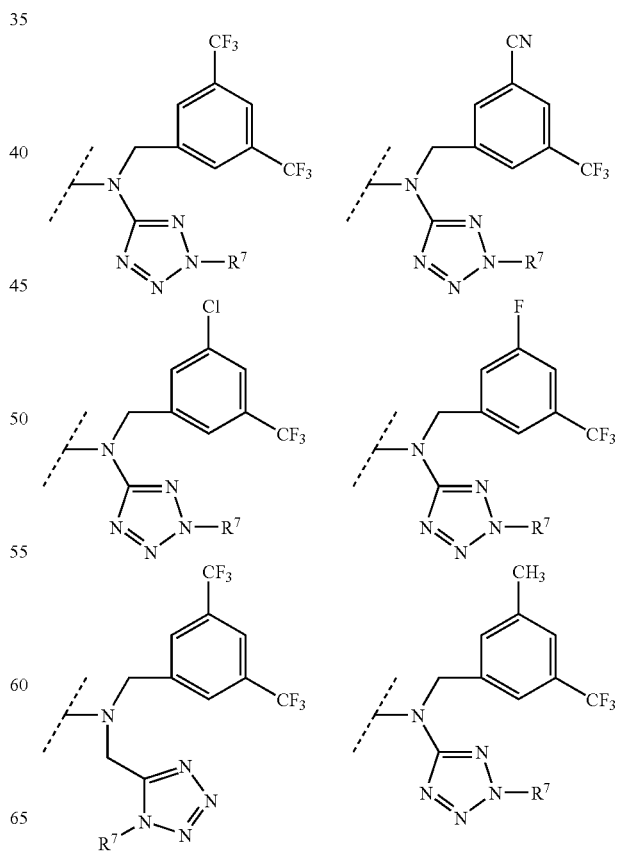

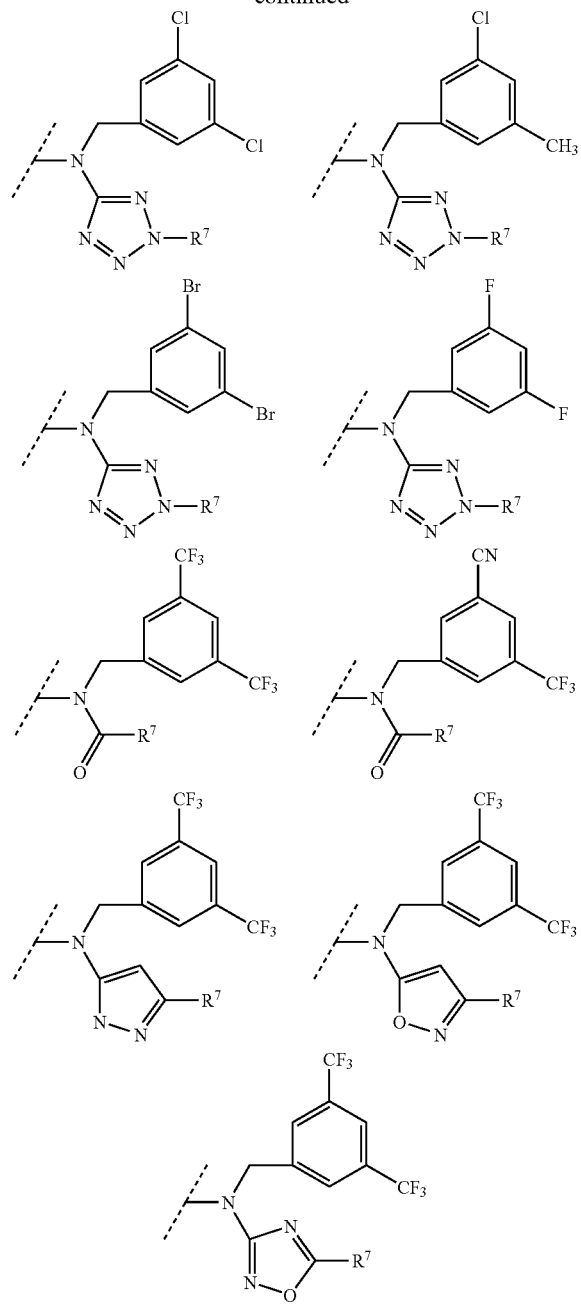

wherein R⁷ is $C_1$-$C_3$ alkyl.

8. A compound according to claim 1 selected from the group consisting of:

Cis-4-[acetyl-(3,5-bis-trifluoromethyl-benzyl)-amino]-2-ethyl-6-methoxy-3,4-dihydro-2H-[1,5]naphthyridine-1-carboxylic acid isopropyl ester, (+/−)-cis-4-[Acetyl-(3,5-bis-trifluoromethyl-benzyl)-amino]-2-ethyl-6-bromo-3,4- dimethylamino-3,4- dihydro-2H-[1,5]naphthyridine-1-carboxylic acid isopropyl ester, (+/−)-cis-4-[Acetyl-(3,5-bis-trifluoromethyl-benzyl)-amino]-2-ethyl-6-methyl-3,4-dihydro-2H -[1,5]naphthyridine-1-carboxylic acid isopropyl ester, (+/−)-cis-4-[(3,5-Bis-trifluoromethyl-benzyl)-(2,5-dimethyl-2H-pyrazole-3-carbonyl)-amino]-2-ethyl-6-trifluoromethyl-3,4-dihydro-2H-quinoline-1-carboxylic acid isopropyl ester, (+/−)-cis-4-(3,5-Bis-trifluoromethyl-benzyl)-1-(cyclopentylmethyl-2-ethyl-6-methoxy- 1,2,3,4-tetrahydro-[1,5]naphthyridine-4-yl)-acetamide, (+/−)-cis-4-[Acetyl-(3,5-bis-trifluoromethyl-benzyl)-amino]-6-methoxy-2-methyl-3,4-dihydro-2H -[1,5]naphthyridine-1-carboxylic acid isopropyl ester, (+/−)-cis-4- [(3,5-Bis-trifluoromethyl-benzyl)-ethoxycarbonyl-amino]-6-methoxy-2-methyl-3,4-dihydro-2H-[1,5]naphthyridine- 1-carboxylic acid isopropyl ester, (+/−)-cis-4- [(3,5-Bis-trifluoromethyl-benzyl)-(3-fluoro-5-trifluoromethyl-benzoyl)-amino]-6-methoxy-2-methyl-3,4-dihydro-2H-[1,5]naphthyridine-1-carboxylic acid isopropyl ester, (+/−)-cis-N-(3,5-Bis-trifluoromethyl-benzyl)-N-(1-cyclopentyl-6-methoxy-2-methyl- 1,2,3,4-tetrahydro-[1,5]napthyridin-4-yl)-acetamide, (+/−)-cis-4-[Acetyl-(3,5-bis-trifluoromethyl-benzyl)-amino]-2-methyl-6-trifluoromethyl-3,4-dihydro-2H-[1,5]naphthyridine- 1-carboxylic acid isopropyl ester, (+/−)-cis-4-[Acetyl-(3,5-bis-trifluoromethyl-benzyl)-amino]-2-cyclopropyl-6-trifluoromethyl-3,4-dihydro-2H-[1,5]naphthyridine-1-carboxylic acid isopropyl ester, 4- [(3,5-Bis-trifluoromethyl-benzyl)-(5,6,7,8-tetrahydroquinolin-3-yl)-amino]-2,3-dimethyl- 3,4,6,7,8,9-hexahydro-2H-benzo[b][1,5]napthyridine-1-carboxylic acid isopropyl ester, or a pharmaceutically acceptable salt, enantiomer or diastereomer or mixture thereof.

9. A method of treating dyslipidemia comprising administering a compound of formula I of claim 1, a pharmaceutically acceptable salt, enantiomer, racemate diastereomer, mixture of diastereomers thereof, to a patient in need thereof.

10. A method of treating atherosclerosis comprising administering a compound of formula I of claim 1, a pharmaceutically acceptable salt, enantiomer, racemate, diastereomer, or mixture of diastereomers thereof to a patient in need thereof.

11. A method of increasing plasma HDL-cholesterol in a mammal comprising administering a therapeutically effective amount of a compound of formula I of claim 1, a pharmaceutically acceptable salt, enantiomer, racemate, diastereomer, or mixture of diastereomers thereof to a patient in need thereof.

12. A pharmaceutical composition comprising a compound according to claim 1, or a pharmaceutically acceptable salt thereof, and a carrier, diluent and/or excipient.

13. A composition of claim 12 further comprising one or more cardio protective agents selected from the group consisting of: statins, leptin, and lipid regulating agents.

14. A method according to claim 10 further comprising administering one or more cardio protective agents selected from the group consisting of: statins, leptin, and lipid regulating agents.

15. A method according to claim 9 comprising increasing plasma HDL- cholesterol in said patient.

16. A method according to claim 9 comprising decreasing plasma LDL- cholesterol in said patient.

17. A method according to claim 10 comprising increasing plasma HDL- cholesterol in said patient.

18. A method according to claim 10 comprising decreasing plasma LDL- cholesterol in said patient.

* * * * *